(12) United States Patent
Takagi et al.

(10) Patent No.: US 8,933,043 B2
(45) Date of Patent: *Jan. 13, 2015

(54) METHODS FOR REGULATION OF P53 TRANSLATION AND FUNCTION

(75) Inventors: Masatoshi Takagi, Tokyo (JP); Michael B. Kastan, Cordova, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/063,463

(22) PCT Filed: Sep. 28, 2006

(86) PCT No.: PCT/US2006/037848
§ 371 (c)(1),
(2), (4) Date: Feb. 11, 2008

(87) PCT Pub. No.: WO2007/041213
PCT Pub. Date: Apr. 12, 2007

(65) Prior Publication Data
US 2009/0149377 A1    Jun. 11, 2009

Related U.S. Application Data

(60) Provisional application No. 60/722,889, filed on Sep. 30, 2005.

(51) Int. Cl.
*C12N 15/11* (2006.01)
*A61K 48/00* (2006.01)
*C12N 15/113* (2010.01)

(52) U.S. Cl.
CPC ........ *C12N 15/1135* (2013.01); *C12N 2310/11* (2013.01); *C12N 2310/14* (2013.01); *C12N 2310/12* (2013.01); *C12N 2310/15* (2013.01)
USPC ...................................... 514/44 R; 514/44 A

(58) Field of Classification Search
USPC ............................................. 514/44 A, 44 R
See application file for complete search history.

(56) References Cited

U.S. PATENT DOCUMENTS

| 8,722,641 B2* | 5/2014 | Kastan et al. .................. 435/375 |
| 2002/0151515 A1 | 10/2002 | Roberts |
| 2003/0175771 A1 | 9/2003 | Velculescu et al. |
| 2003/0175862 A1 | 9/2003 | Brachmann |
| 2003/0215803 A1 | 11/2003 | Garcia et al. |
| 2004/0048256 A1 | 3/2004 | Agee et al. |
| 2004/0259247 A1* | 12/2004 | Tuschl et al. .................. 435/375 |
| 2006/0199778 A1 | 9/2006 | Ellis-Behnke et al. |
| 2007/0003936 A1 | 1/2007 | Gite et al. |

FOREIGN PATENT DOCUMENTS

WO       03/050236       6/2003

OTHER PUBLICATIONS

Bae, Byoung-Il, et al., "p53 Mediates Cellular Dysfunction and Behavioral Abnormalities in Huntington's Disease," Neuron, vol. 47, Jul. 7, 2005, p. 29-41.
Bates, Paula J., et al., "Antiproliferative Activity of G-rich Oligonucleotides Correlates with Protein Binding," The Journal of Biological Chemistry, vol. 274, No. 37, Sep. 10, 1999, p. 26369-26377.
Botchkarev, Vladimir, et al., "p53 Is Essential for Chemotherapy-induced Hair Loss," Cancer Research, vol. 60, 2000, p. 5002-5006.
Bunz, Fred, et al., "Disruption of p53 in Human Cancer Cells Alters the Responses to Therapeutic Agents," The Journal of Clinical Investigation, vol. 104, No. 3, 1999, p. 263-269.
Chen, Zhenbang, et al., "Crucial Role of p53-Dependent Cellular Senescence in Suppression of Pten-deficient Tumorigenesis," Nature, vol. 436, Aug. 2005, p. 725-730.
Chu, E., et al., "Thymidylate Synthase Protein and p53 mRNA form an In Vivo Ribonucleoprotein Complex," Molecular and Cellular Biology, vol. 19, No. 2, 1999, p. 1582-1594.
Dai, Mu-Shui, et al., "Inhibition of MDM2-Mediated p53 Ubiquitination and Degradation by Ribosomal Protein L5," Journal of Biological Chemistry, vol. 279, No. 43, 2004, p. 44475-44482.
Dai, Mu-Shui, et al., "Ribosomal Protein L23 Activates p53 by Inhibiting MDM2 Function in Response to Ribosomal Perturbation but Not to Translation Inhibition," Molecular and Cellular Biology, vol. 24, No. 17, 2004, p. 7654-7668.
Dapic, Virna, et al., "Biophysical and Biological Properties of Quadruplex Oligodeoxyribonucleotides," Nucleic Acids Research, vol. 31, No. 8, 2003, p. 2097-2107.
Erratum to Takagi, Masatoshi, et al., Cell, vol. 123 (3), Oct. 2005, p. 536-7.
Ferber, Dan, "The New Way to Combat Therapy Side Effects," Science, vol. 285, 1999, p. 1651-1653.
Fu, Loning, et al., "A Translation Repressor Element Resides in the 3' Untranslated Region of Human p53 mRNA," Oncogene, vol. 18, 1999, p. 6419-6424.
Fu, Loning., et al., "Participation of the Human p53 3' UTR in Translational Repression and Activation Following Gamma-Irradiation," The EMBO Journal, vol. 16, No. 13, 1997, p. 4117-4125.
Fu, Loning, et al., "Translational Regulation of Human p53 Gene Expression," The EMBO Journal, vol. 15, No. 16, 1996, p. 4392-4401.
Gudkov, Andrei V., et al., "The Role of p53 in Determining Sensitivity to Radiotherapy," Nature Reviews/Cancer, vol. 3, 2003, p. 117-129.
Haass, Christian, "New Hope for Alzheimer Disease Vaccine," Nature Medicine, vol. 8, No. 11, 2002, p. 1195-1199.

(Continued)

*Primary Examiner* — Jon E Angell
(74) *Attorney, Agent, or Firm* — Troutman Sanders LLP

(57) ABSTRACT

The present invention relates to novel methods for modulating the activity of p53 tumor suppressor protein by affecting p53 translational regulation. More specifically, the invention relates to novel methods for modulating p53 mRNA translation in a cell by affecting a function of a p53 5'-untranslated region (5'UTR), including its interaction with proteins such as Ribosomal Protein L26 (RPL26), nucleolin, and p53. The invention also relates to the use of these methods for treating cancer, neurodegenerative disorders and minimizing the negative effects of cellular stresses.

13 Claims, 3 Drawing Sheets

(56) References Cited

OTHER PUBLICATIONS

Jin, Aiwen, et al., "Inhibition of HDM2 and Activation of p53 by Ribosomal Protein L23," Molecular & Cellular Biology, vol. 24, No. 17, 2004, p. 7669-7680.

Ju, J., et al., "Regulation of p53 Expression by Thymidylate Synthase," Proceedings of the National Academy of Science U.S.A, vol. 96, No. 7, 1999, p. 3769-3774.

Kastan, MB, et al., "A Mammalian Cell Cycle Checkpoint Pathway Utilizing p53 and GADD45 is Defective in Ataxia-Telangiectasia," Cell, vol. 71, 1992, p. 587-597.

Kastan, MB, et al., "Participation of p53 Protein in the Cellular Response to DNA Damage," Cancer Research, vol. 51, 1991, p. 6304-6311.

Komarova, Elena A., "Chemoprotection from p53-dependent Apoptosis: Potential Clinical Applications of the p53 Inhibitors," Biochemical Pharmacology, vol. 62, 2001, p. 657-667.

Lohrum, Marion E., et al., "Regulation of HDM2 Activity by the Ribosomal Protein L11," Cancer Cell, vol. 3, No. 6, 2003, p. 577-587.

Mazan-Mamczarz, K., et al., "RNA-Binding Protein HuR Enhances p53 Translation in Response to Ultraviolet Light Irradiation," Proceedings of the National Academy of Science U.S.A., vol. 100, No. 14, 2003, p. 8354-8359.

Mosner, J., et al., "Negative Feedback Regulation of Wild-Type p53 Biosynthesis," The EMBO Journal, vol. 14, No. 18, 1995, p. 4442-4449.

Takagi, Masatoshi, et al., "Regulation of p53 Translation and Induction after DNA Damage by Ribosomal Protein L26 and Nucleolin," Cell, vol. 123, Oct. 7, 2005, p. 49-63.

Xu, Xiaohua, et al., "Inhibition of DNA Replication and Induction of S Phase Cell Cycle Arrest by G-rich Oligonucleotides," The Journal of Biological Chemistry, vol. 276, No. 46, Nov. 16, 2001, p. 43221-43230.

Yang, Chonglin, et al., "Identification of Nucleolin and Nucleophosmin as Genotoxic Stress-Responsive RNA-Binding Proteins," Nucleic Acids Research, vol. 30, No. 10, 2002, p. 2251-2260.

Zhang, Yanping, et al., "Ribosomal Protein L11 Negatively Regulates Oncoprotein MDM2 and Mediated a p53-Dependent Ribosomal-Stress Checkpoint Pathway," Molecular & Cellular Biology, vol. 23, No. 23, 2003, p. 8902-8912.

Mokdad-Gagouri, et al. "Translational Control of Human p53 Expression in Yeast Mediated by 5'-UTR-ORF Structural Interactions." Nucleic Acids Research, Mar. 1, 2001, vol. 29, No. 5, pp. 1222-1227.

Daniely et al. "Stress-Dependent Nucleolin Mobilization Mediated by p53-Nucleolin Complex Formation." Molecular and Cellular Biology, vol. 22, No. 16, pp. 6014-6022.

Horton et al. "p53 Activation Results in Rapid Dephospohorlyation of the eIF4E-Binding Protein 4E-BP1, Inhibition of Ribosomal Protein S6 Kinase and Inhibition of Translation Initiation." Oncogene, vol. 21, No. 34, pp. 5325-5334.

Gudkov, "Cancer Drug Discovery: the Wisdom of Imprecision." Nature Medicine, Dec. 2004, vol. 10, No. 12, pp. 1298-1299.

Zhang, et al. "Identification and Analysis of Over 2000 Ribosomal Protein Pseudogenes in the Human Genome." Genome Research, Oct. 2002, vol. 12, No. 10, pp. 1466-1482.

Komarov, P.G., et al. "A chemical inhibitor of p53 that protects mice from the side effects of cancer therapy", Science (1999) vol. 285, p. 1733-1737.

Ofir-Rosenfeld, Y., et al. "Mdm2 Regulates p53 mRNA Translation through Inhibitory Interactions with Ribosomal Protein L26," Molecular Cell (2008) vol. 32, p. 180-189.

Schumacher, B., et al. "Translational repression of *C. elegans* p53 by GLD-1 regulates DNA damage-induced apoptosis," Cell (2005) vol. 120, p. 357-368.

Yang et al., "The identification of an internal ribosomal entry site in the 5'-untranslated region of p53 mRNA provides a novel mechanism for the regulation of its translation following DNA damage" Oncogene (2006) vol. 25, p. 4613-4619.

International Search Report and Written Opinion dated May 5, 2008, which issued during the prosecution of International Application No. PCT/US06/37848, which corresponds to the present application.

* cited by examiner

```
GTTTTCCCCTCCCATGTGCTCAAGACTGGCGCTAAAAGTTTTGAGCTTCTCAAAAGTCTAGAGCCACCGTCCAGGGAGCAGGTA
GTTTTCCCCTCCCATGTGCTCAAGACTGGCGCTAAAAGTTTTGAGCTTCTCAAAAGTCTAGAGCCACCGTCCAGGGAGCGGGTA
GTTTTCCCCTCCCATGTGCTCAAGACTGGCGCTAAAAGTTTTGAGCTTCTCAAAAGTCTAGAGCCACCGTCCAGGGAGCAGGTA
 TTTTCCCCTCCCATGTGCTCAAGACTGGCGCTAAAAGTTTTGAGCTTCTCAAAAGTCTAGAGCCACCGTCCAGGGAGCAGGTA
     CCCTCCCATGTGCTCAAGACTGGCGCTAAAAGTTTTGAGCTTCTCAAAAGTCTAGAGCCACCGTCCAGGGAGCAGGTA
          CATGTGCTCAAGACTGGCGCTAAAAGTTTTGAGCTTCTCAAAAGTCTAGAGCCANCGTCCAGGGAGCTGGTA
               AAGACTGGCGCTAAAAGTTTTGAGCTTCTCAAAAGTCTAGAGCCACCGTCCAGGGAGCAGGTA
               AAGACTGGCGCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      GCTAAAAGTTTTGAGCTTCTCAAAAGTCTAGAGCCACCGTCCAGGGAGCAGGTA
                      gCTAAAAGTTtTGAgcTTcTCAAAAGTCTAGAGCCACCGTCCAGGGAGCAGGTA
                      tAAAAGNTTTNNGNTTCTCAAAAGGNTAGAGCCACCNTCCAGGCAGCNGGTA
                       AGTTTTGAGCTTCTCAAAAGTCTAGAGCCACCGTCCAGGGAGCAGNTA
                         GTTTTGAGCTTCTCAAAAGTCTAGAGCCACCGTCCAGGGAGCGGGTA
                            GAGCTTCTCAAAAGTCTAGAGCCACCGTCCAGGGAGCAGGTA
                                TCTCAAAAGTCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                 CTCAAAAATCTAGAGCCACCGTCCAGGGAGCAGGTA
                                  TCAAAAGTCTAGAGCCACCGTCCAGGGAGCAGGTA
                                  TCAAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
                                    AAAAGTCTAGAGCCACCGTCCAGGGAGCAGGTA
```

METHODS FOR REGULATION OF P53 TRANSLATION AND FUNCTION

CROSS-REFERENCE TO RELATED APPLICATIONS

This application is a national phase of International Application No. PCT/US06/37848, filed Sep. 28, 2006, which claims the benefit of U.S. Provisional Application No. 60/722,889 filed Sep. 30, 2005, both of which are hereby incorporated by reference. International Application No. PCT/US06/37848 published in English on Apr. 12, 2007under Publication No. WO 2007/041213.

STATEMENT REGARDING FEDERALLY SPONSORED RESEARCH OR DEVELOPMENT

The research leading to the present invention was supported, in part, by NIH grants ES05777 and CA21765. Accordingly, the U.S. government has certain rights in the invention.

FIELD OF THE INVENTION

The present invention relates to modulating the activity of p53 tumor suppressor protein by affecting p53 translational regulation and its use for treating cancer, neurodegenerative disorders, and minimizing the negative effects of cellular stresses. More specifically, the invention relates to modulating p53 mRNA translation in a cell by affecting a function of a p53 5'-untranslated region (5'UTR), including its interaction with proteins such as Ribosomal Protein L26 (RPL26), nucleolin, and p53.

BACKGROUND OF THE INVENTION

The p53 gene is one of the most studied and well-known genes. p53 plays a key role in cellular stress response mechanisms by converting a variety of different stimuli, for example, DNA damage, deregulation of transcription or replication, and oncogene transformation, into cell growth arrest or apoptosis (Kastan et al., Cancer Res 1991; 51:6304-6311; Vogelstein et al., Nature 2000; 408:307-310; Vousden et al., Nat Rev Cancer 2002; 2:594-604; Giaccia et al., Genes & Development 1998; 12:2973-2983; T. M. Gottlieb et al., Biochem. Biophys. Acta, 1287, p. 77 (1996)).

The p53 protein is active as a homo-tetramer and exerts its tumor suppressor function mainly as a transcription factor that affects G1 and G2 cell cycle arrest and/or apoptosis (see, e.g., Donehower and Bradley, Biochim Biophys Acta., 1993, 1155(2):181-205; Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31). The p53-mediated G1 arrest is its best characterized activity and involves transcriptional activation of the downstream gene p21 WAF1/CIP1/SDI1 (Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31). Other downstream effector genes for p53-mediated G1 arrest may exist, since p21−/− mouse embryonic fibroblasts do not show complete abrogation of G1 arrest after DNA damage (Brugarolas et al., Nature, 1995, 377(6549): 552-7; Deng et al., Cell, 1995, 82(4):675-84). The G2/M effects of p53 involve, at least in part, induction of 14-3-3σ (Hermeking et al., Mol. Cell, 1997, 1(1):3-11).

The mechanisms for apoptosis induction and their relative importance remain less clear at present. In certain settings p53 clearly induces pro-apoptotic genes. These include BAX and Fas/APO1 (Miyashita and Reed, Cell, 1995, 80(2):293-9; Owen-Schaub et al., Mol. Cell. Biol., 1995, 15(6):3032-40) neither of which, however, is an absolute requirement for p53-induced apoptosis (Fuchs et al., Cancer Res., 1997, 57(13):2550-4). Recently, many more genes have been identified that are induced directly or indirectly during p53-mediated apoptosis (Polyak et al., Nature, 1997, 389(6648):300-5), but the essential genes for p53-induced apoptosis still have to be determined. Transcriptional repression of anti-apoptotic genes, such as bcl-2, may play a role (Haldar et al., Cancer Res., 1994, 54(8):2095-7; Miyashita et al., Oncogene, 1994, 9(6):1799-805) and other non-transcriptional mechanisms may be important as well (Caelles et al., Nature, 1994, 370 (6486):220-3; Haupt et al., Nature 1997; 387:296-299).

Several upstream signals activate p53. These include DNA damage, hypoxia and critically low ribonucleoside triphosphate pools (Kastan et al., Cancer Res. 1991; 51:6304-6311; Graeber et al., Nature, 1996, 379(6560):88-91; Linke et al., Genes Dev., 1996, 10(8):934-47). Once activated, p53 induces either cell cycle arrest or apoptosis, depending on several factors such as the amount of DNA damage, cell type and cellular milieu, e.g., presence or absence of growth factors (Donehower and Bradley, Biochim Biophys Acta., 1993, 1155(2):181-205; Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31).

Cancer cells show decreased fidelity in replicating their DNA, often resulting in DNA damage, and tumor masses have inadequate neovascularization leading to ribonucleoside triphosphate or oxygen deprivation, all upstream signals that activate p53. In view of p53's capability to induce cell cycle arrest or apoptosis under these conditions it is not surprising that absent or significantly reduced activity of the tumor suppressor protein p53 is a characteristic of more than half of all human cancers (Harris and Hollstein, N. Engl J. Med., 1993, 329(18):1318-27; Greenblatt et al., Cancer Res., 1994, 54(18):4855-78). In the majority of cancers, p53 inactivation is caused by missense mutations in one p53 allele, often with concomitant loss-of-heterozygosity (Michalovitz et al., J. Cell. Biochem., 1991, 45(1):22-9; Vogelstein and Kinzler, Cell, 1992, 70(4):523-6; Donehower and Bradley, Biochim. Biophys. Acta., 1993, 1155(2):181-205; Levine, Cell, 1997, 88(3):323-31). These mutations affect almost exclusively the core DNA-binding domain of p53 that is responsible for making contacts with p53 DNA-binding sites, while mutations in the N-terminal transactivation domain or the C-terminal tetramerization domain are extremely rare (Beroud and Soussi, Nucleic Acids Res., 1998, 26(1):200-4; Cariello et al., Nucleic Acids Res., 1998, 26(1):198-9; Hainaut et al., P., Nucleic Acids Res. 1998; 26:205-213).

Contrary to wild-type p53, p53 cancer mutants have a long half-life and accumulate to high levels in cancer cells (Donehower and Bradley, Biochim Biophys Acta., 1993, 1155(2): 181-205; Lowe, Curr. Opin. Oncol., 1995, 7(6):547-53). This may be explained by their inability to activate the mdm-2 gene (Lane and Hall, Trends Biochem. Sci., 1997, 22(10): 372-4.), since mdm-2 induces degradation of p53 via the ubiquitin pathway as part of a negative feedback loop (Haupt et al., Nature 1997; 387:296-299; Kubbutat et al., Nature 1997; 387:299-303). The unusually high frequency of p53 missense mutations in human cancers (as opposed to mutations resulting in truncated proteins) is explained by their dominant-negative effect that depends on the intact C-terminal tetramerization domain. The C-terminus allows p53 cancer mutants to form hetero-tetramers with wild-type p53 (Milner and Medcalf, Cell, 1991, 65(5):765-74), thus reducing, or even abrogating, the activity of wild-type p53 protein (Michalovitz et al., J. Cell. Biochem., 1991, 45(1):22-9; Vogelstein and Kinzler, Cell, 1992, 70(4):523-6; Ko and Prives, Genes Dev., 1996, 10(9):1054-72). In addition, there is evidence that at least some of the same missense mutations may confer a gain-of-function (Gottlieb and Oren, Biochim. Biophys. Acta., 1996, 1287(2-3):77-102; Ko and Prives, Genes Dev., 1996, 10(9):1054-72; Levine, Cell, 1997, 88(3): 323-31).

p53 has a short half-life, and, accordingly, is continuously synthesized and degraded in the cell. However, when a cell is subjected to stress, p53 is stabilized. Examples of cell stress that induce p53 stabilization are: a) DNA damage, such as damage caused by UV (ultraviolet) radiation, cell mutations, chemotherapy, and radiation therapy; b) hyperthermia; and c) deregulation of microtubules caused by some chemotherapeutic drugs, e.g., treatment using taxol or Vinca alkaloids.

When activated, p53 causes cell growth arrest or a programmed, suicidal cell death, which in turn acts as an important control mechanism for genomic stability. In particular, p53 controls genomic stability by eliminating genetically damaged cells from the cell population, and one of its major functions is to prevent tumor formation.

The p53 gene is commonly mutated in human cancers (Levine et al., Br. J. Cancer 1994; 69:409 and Thompson et al., Br. J. Surg. 1998; 85:1460; Hainaut et al., P., Nucleic Acids Res. 1998; 26:205-213) and inherited mutations in the gene lead to the profound cancer predisposition Li-Fraumeni syndrome (Malkin et al., Science 1990; 250:1233-1238). Loss of the p53 gene in combination with loss of one or more additional tumor suppressor genes is associated with malignant tumor progression. For example, loss of both the p53 gene and the tumor suppressor PTEN are associated with advanced stages of prostate cancer (Di Cristofano et al, Cell 2000; 100:387-390; Vogelstein et al., Nature 2000; 408:307-310). As shown by Chen et al (Nature 2005; 436:725-730), the loss of PTEN alone leads to increased p53 levels and induction of a cellular senescence program for tumor suppression in the PTEN-deficient, neoplastic tissue, while subsequent loss of p53 following PTEN loss removes the senescent signal and leads to aggressive tumor growth. Thus, treatment of early stages of PTEN-deficient prostate neoplasia may benefit from p53 activation in favor of programmed cellular senescence to suppress tumor progression.

The reason that inherited or sporadic mutations in the p53 gene contribute to the development of malignancies is presumably related to its cellular stress response functions. Failure to induce appropriate growth arrest or apoptosis after DNA damage is thought to promote genetic instability or inappropriate survival of damaged cells. Thus, an inability to activate p53 function after DNA damage or other cellular stresses can contribute to the generation of viable, genetically altered cells that can lead to malignancy. A loss or inactivation of p53, therefore, is associated with a high rate of tumor progression and a resistance to cancer therapy. Therefore, conventional theories dictate that suppression of p53 would lead to disease progression and protection of the tumor from a cancer therapy.

Importantly, however, p53 also imparts a high sensitivity to several types of normal tissue subjected to genotoxic stress. Specifically, radiation therapy and chemotherapy exhibit severe side effects, such as severe damage to the lymphoid and hematopoietic system and intestinal epithelia, which limit the effectiveness of these therapies. Other side effects, like hair loss, also are p53 mediated and further detract from cancer therapies. These side effects are caused by p53-mediated apoptosis, which maps tissues suffering from side effects of cancer therapies. Therefore, to eliminate or reduce adverse side effects associated with cancer treatment, it would be beneficial to inhibit p53 activity in normal tissue during treatment of p53-deficient tumors, and thereby protect normal tissue (Komarova et al., Seminars in Cancer Biology 1998; 8(5):389-400).

In summary, p53 has a dual role in cancer therapy. On one hand, p53 acts as a tumor suppressor by mediating apoptosis and growth arrest in response to a variety of stresses and controlling cellular senescence. On the other hand, p53 is responsible for severe damage to normal tissues during cancer therapies. The damage caused by p53 to normal tissue made p53 a potential target for therapeutic suppression. In addition, because more than 50% of human tumors lack functional p53, suppression of p53 would not affect the efficacy of a treatment for such tumors, and would protect normal p53-containing tissues. It has been recognized, however, that therapeutic p53 inhibition should be reversible as long-term p53 inactivation can significantly increase the risk of cancer. For further details on suppression of p53 see, e.g., U.S. Pat. Nos. 6,593,353 and 6,420,136.

The adverse effects of p53 activity on an organism are not limited to cancer or cancer therapies. p53 is activated as a consequence of a variety of stresses associated with injuries (e.g., burns), naturally occurring diseases (e.g., hyperthermia associated with fever, and conditions of local hypoxia associated with a blocked blood supply, stroke, and ischemia) and cell aging (e.g., senescence of fibroblasts). p53 inhibition, therefore, also can be therapeutically effective, for example, in reducing or eliminating p53-dependent neuronal death in the central nervous system (e.g., after brain and spinal cord injury), reducing or eliminating neuronal damage during seizures, suppressing tissue aging, or preservation of tissues and organs prior to transplantation.

p53 regulation has also been shown to affect the pathogenesis of neurodegenerative diseases. For example, as shown by Bae et al. (Neuron 2005; 47:29-41), (i) p53 levels are increased in the brains of mutant huntingtin protein (mHtt) transgenic mice (mHtt-Tg) and Huntington's Disease (HD) patients and (ii) upregulation of p53 transcriptional activity and nuclear p53 levels by mHtt leads to mitochondrial depolarization and cytotoxicity in neuronal cell cultures, revealing a role for p53 regulation in the development of HD. Reduction or elimination of p53 suppresses this neurodegenerative effect. Thus, p53 regulation can be beneficial for amelioration of HD and other neurodegenerative diseases.

Optimal induction of growth arrest or apoptosis after DNA damage requires an increase in the intracellular levels of functional p53 protein (Canman et al., Oncogene 1998; 16:957-966; Canman et al., Genes & Dev. 1995; 9:600-611; Kuerbitz et al, Proc Natl Acad Sci 1992; 89:7491-7495). The increases in p53 protein levels are dependent on the ATM protein kinase after ionizing irradiation (IR) (Kastan et al., Cell 1992; 71:587-597) and on the ATR protein kinase after UV irradiation and many other types of cellular stress (Tibbetts et al., Genes & Development 1999; 13:152-157; Hammond et al., Mol Cell Biol. 2002; 22:1834-1843; Wright et al., Pro Natl Acad Sci U.S.A. 1998; 95:7445-7450). There is a measurable increase in the half-life of p53 protein after DNA damage (Maltzman et al., Molec and Cell Biol 1984; 4(9): 1689-1694; Price et al., Oncogene 1993; 8:3055-3062; Maki et al, Mol. Cell. Biol. 1997; 17:355-363) and the increases in cellular p53 protein levels have largely been attributed to this change in half-life. p53 protein is normally a very short-lived cellular protein with rapid proteosomal degradation in unperturbed cells. The HDM2 protein (MDM2 in mice) directly binds to p53 protein (Momand et al., Cell 1992; 69:1237-1245; Oliner et al., Nature 1993; 362:857-860) and functions as an E3 ubiquitin ligase to facilitate the degradation of p53 (Fang et al., S., J Biol Chem 2000; 275:8945-8951; Honda et al., FEBS Letters 1997; 420:25-27; Haupt et al., Nature 1997; 387:296-299; Kubbutat et al., Nature 1997; 387:299-303). Post-translational modifications of HDM2 and p53 after DNA damage appear to inhibit the ability of HDM2 to bind to p53 (Mayo et al., Cancer Research 1997; 57:5013-5016; Khosravi et al., PNAS 1999; 96:14973-14977; Maya et al., Genes & Development 2001; 15:1067-1077; Shieh et al., Cell 1997; 91:325-334; Ashcroft et al., Molecular & Cellular Biology 1999; 19:1751-1758), thus decreasing the proteasomal degradation of p53 protein and increasing cellular levels of the protein. Similarly, induction of the ARF tumor suppressor by oncogenes and other cellular signals leads to increases in p53 protein levels by ARF protein binding to HDM2 and inhibiting HDM2-mediated degradation of p53 (Palmero et al., Nature 1999; 395:127; Kamijo et al., Proc. Natl. Acad. Sci. U.S.A 1998; 95:8292-8297; Sherr et al., Curr. Opin. Genet. Dev. 2000; 10:94-99; Pomerantz et al., Cell 1998; 92:713-723; Stott et al., EMBO J. 1998; 17:5001-5014). Thus, cells with overexpressed HDM2 or inactive ARF are similar to cells containing mutated p53 genes in that normal p53 regulation is lacking.

Several reports have suggested that translational regulation may also contribute to p53 induction after DNA damage. In the initial reports of p53 induction after ionizing irradiation, the protein synthesis inhibitor cycloheximide was shown to block p53 induction and marked increases in labeling of p53 protein with [$^{35}$S]-methionine were noted early after treatment (Kastan et al., Cancer Res 1991; 51:6304-6311; Kastan et al., Cell 1992; 71:587-597). Subsequently, a translation suppressor element was reported in the 3'UTR of the p53 mRNA (Fu et al., Embo J 1997; 16:4117-4125; Fu et al., Oncogene 1999; 18:6419-6424; Fu et al., EMBO J. 1996; 15:4392-4401) and a stem loop structure was predicted in the 5'UTR of the murine p53 gene (Mosner et al., EMBO J. 1995; 14:4442-4449). Interestingly, p53 was suggested to negatively regulate its own translation by direct binding of p53 protein to this 5'UTR stem loop structure (Mosner et al., EMBO J. 1995; 14:4442-4449). Two other proteins have also been reported to modulate p53 translation: thymidylate synthase suppresses p53 translation by binding to the coding sequence of p53 mRNA (Chu et al., Mol. Cell. Biol. 1999; 19:1582-1594; Ju et al., Proc. Natl. Acad. Sci. U.S.A 1999; 96:3769-3774) and HuR (Hu antigen R) enhances the translation efficiency of p53 after ultraviolet irradiation by binding to an AU-rich sequence at the 3'UTR of p53 mRNA (Mazan-Mamczarz et al., Proc. Natl. Acad. Sci. U.S.A 2003; 100: 8354-8359).

Despite suggestions that translational control of p53 might be important, the extent, importance and mechanism of p53 translational regulation after DNA damage has remained unclear.

BRIEF SUMMARY OF THE INVENTION

As specified in the Background Section, there is a great need in the art to identify additional methods for modulating the activity of p53 to provide novel more efficient treatments for cancer, neurodegenerative diseases and various types of cell damage. The present invention addresses these and other needs by identifying novel methods for modulating the activity of p53 by affecting p53 translational regulation.

The first object of the invention is to provide a method for modulating the level and/or induction of the p53 tumor suppressor protein in a cell, which method comprises modulating p53 mRNA translation in the cell by affecting a function of a p53 5'-untranslated region (5'UTR). In one embodiment, modulation of p53 mRNA translation results in decreased levels and/or decreased induction of p53. In another embodiment, modulation of p53 mRNA translation results in increased levels and/or increased induction of p53. Within the meaning of the present invention, the term "a function of a p53 5'UTR" encompasses all possible structural and functional interactions of a p53 5'UTR, including changes in its secondary and/or tertiary structure as well as interactions with various molecules (e.g., proteins, nucleic acids, ions, etc.).

In a specific embodiment, the p53 5'UTR comprises nucleotides (nt) −139 to 1 of the p53 transcript, which, in the case of human p53, corresponds to AAAAGTCTAGAGCCAC-CGTCCAGGGAGCAGGTAGCT-GCTGGGCTCCGGGGACACTT TGCGTTCGGGCTGG-GAGCGTGCTTTCCACGACGGTGACACGCTTCCCTG GATTGGC AGCCAGACTGCCTTCCGGGTCACTGCC (SEQ ID NO: 1). In another specific embodiment, the p53 5'UTR comprises nucleotides (nt) −75 to 1 of the p53 transcript, which, in the case of human p53, corresponds to GGCTGGGAGCGTGCTTTCCACGACGGT-GACACGCTTCCCTGGATTGGCAGCCAGAC TGCCT-TCCGGGTCACTGCC (SEQ ID NO: 2). In yet another specific embodiment, the p53 5'UTR comprises nucleotides (nt) −190 to 1 of the p53 transcript, which, in the case of human p53, corresponds to GTTTTCCCCTCCCATGTGCTCAA-GACTGGCGCTAAAAGTTTTGAGCTTCTCAAAAGT CTAGAGCCACCGTCCAGGGAGCAGG-TAGCTGCTGGGCTCCGGGGACACTTTGCGTT CGGGCTGGGAGCGTGCTTTCCACGACG-GTGACACGCTTCCCTGGATTGGCAGCCAG ACTGC-CTTCCGGGTCACTGCC (SEQ ID NO: 3).

In one embodiment, the p53 5'UTR comprises a stem loop structure, which, in the case of human p53, comprises at least a part of the sequence GTTTTCCCCTCCCATGTGCTCAA-GACTGGCGCTAAAAGTTTTGAGCTTCTCAAAAGT CTAGAGCCACCGTCCAGGGAGCAGG-TAGCTGCTGGGCTCCGGGGACACTTTGCGTT CGGGCTGGGAGCGTGCTTTCCACGACG-GTGACACGCTTCCCTGGATTGGCAGCCAG ACTGC-CTTCCGGGTCACTGCC (SEQ ID NO: 4).

In a specific embodiment, the function of a p53 5'UTR is affected by modulating protein interaction with the p53 5'UTR. In a preferred embodiment, the protein interacting with the p53 5'UTR is selected from the group consisting of Ribosomal Protein L26 (RPL26) (e.g., human RPL26 protein having GenBank Accession No. NP_000978; SEQ ID NO: 16), nucleolin (e.g., human nucleolin protein having GenBank Accession No. NP_005372; SEQ ID NO: 24), and p53 (e.g., human p53 protein having GenBank Accession No. NP_000537; SEQ ID NO: 25).

In conjunction with this embodiment, the invention also provides a method for modulating the level of the p53 tumor suppressor protein in a cell, which method comprises modulating in the cell the level or activity (including interaction with p53 5'UTR) of at least one protein selected from the group consisting of RPL26, nucleolin, and p53. In one preferred embodiment, the invention provides a method, wherein the level of the p53 tumor suppressor protein in the cell is increased by increasing the level or activity of RPL26 in the cell, including increasing the level or activity of an RPL26 fragment which possesses the p53 translation-augmenting activity of the full-length RPL26 (e.g., human RPL26 fragment comprising amino acids 63-90 KGQQIGKV-VQVYRKKYVIYIERVQREKA (SEQ ID NO: 11). In another preferred embodiment, the invention provides a method, wherein the level of the p53 tumor suppressor protein in the cell is increased by decreasing the level or activity of nucleolin in the cell. In another preferred embodiment, the invention provides a method, wherein the level of the p53 tumor suppressor protein in the cell is decreased by decreasing the level or activity of RPL26 in the cell. In yet another preferred embodiment, the invention provides a method, wherein the level of the p53 tumor suppressor protein in the cell is decreased by increasing the level or activity of nucleolin in the cell.

According to the present invention, protein interaction (e.g., interaction of RPL26 or nucleolin or p53) with a p53 5'UTR and/or the level or activity of RPL26 or nucleolin may be modulated using a molecule selected from the group consisting of fragments of p53 5'UTR which can compete with RPL26 or nucleolin or p53 for interaction with p53 5'UTR, antisense oligonucleotides, ribozymes, triple helix-forming oligonucleotides, interfering RNA molecules (e.g., short interfering RNA (siRNA) molecules or short hairpin RNA (shRNA) molecules), peptides, proteins, synthetic molecules (including various small molecules), naturally occurring molecules, and the like. In a specific embodiment, the invention provides a fragment of p53 5'UTR comprising nucleotides (nt) −22 to −1 of human p53 transcript GACTGCCTTCCGGGTCACTGCC (SEQ ID NO: 6) which can compete with RPL26 for interaction with p53 5'UTR. In another specific embodiment, the invention provides an siRNA molecule having the sequence CCGAAAGGAUGAUGAAGUUUU (SEQ ID NO: 8) which can modulate the level or activity of RPL26. In yet another specific embodiment, the invention provides a shRNA having the sequence AGAGCGAGATGCGAGAACA (SEQ ID NO: 9) which can modulate the level or activity of nucleolin.

As specified above, the method of the invention can be used either for increasing/inducing translation of p53 or for decreasing/blocking translation of p53. Increasing/inducing translation of p53 can lead to selectively enhancing/inducing a cell cycle arrest and apoptosis in a cell. In this way, the methods of the invention can be used for treating various cancers characterized by the existing wild-type p53 gene expression, such as neuroblastomas, lymphomas, leukemias, brain tumors, breast cancers, sarcomas, germ cell tumors, prostate cancers, eye tumors, melanomas and other skin cancers, lung cancers, cervical cancers, ovarian cancers, etc. The present invention therefore provides a method for treating a cancer in a mammal, which method comprises increasing the level of the p53 tumor suppressor protein in the cancer cells of the mammal by inducing and/or increasing p53 mRNA translation in said cells, wherein p53 mRNA translation is induced and/or increased by modulating a function of a p53 5'UTR. In a specific embodiment, the invention provides a method for treating a cancer in a mammal, which method comprises increasing the level of the p53 tumor suppressor protein in the cancer cells of the mammal by increasing the level or activity of RPL26 in said cells. In another embodiment, the invention provides a method for treating a cancer in a mammal, which method comprises increasing the level of the p53 tumor suppressor protein in the cancer cells of the mammal by decreasing the level or activity of nucleolin in said cells.

Decreasing/blocking translation of a wild-type p53 tumor suppressor protein can lead to enhanced survival of a cell. Decreasing translation of p53 or blocking its induction is useful, for example, for protection from cell killing which results from cellular stresses such as ionizing radiation, presence of a DNA damaging agent, hypoxia, hyperthermia, oxidation damage, chemical carcinogens, chemotherapeutic agents, UV light, etc.

Also, as specified in the Background Section above, decreasing translation of p53 or blocking its induction can suppress neuronal mitochondrial membrane depolarization and cytotoxicity associated with neurodegenerative disorders such as Huntington's Disease.

Accordingly, the methods of the invention can be used, for example, for (i) protection from toxicities of chemotherapy and radiation therapy (in particular, in the treatment of tumors containing mutant p53 (about 50% of all human tumors), where the decreasing/blocking p53 translation could protect the normal tissue but not affect the response of the tumor), or unplanned radiation exposure (e.g., terrorist act), (ii) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., hyperthermia associated with fever) or in hyperthermia, (iii) inhibiting/decreasing tissue/cell aging, (iv) reducing or eliminating p53-dependent neuronal death or damage (e.g., after brain or spinal cord injury or seizure), (v) preservation of tissues and organs prior to transplanting, or (vi) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like).

The present invention therefore provides a method for preventing negative effects of a cellular stress in a mammal, which method comprises decreasing the level of the p53 tumor suppressor protein in the cells of the mammal, which cells have been subjected to stress, by decreasing the stress-induced p53 mRNA translation in said cells, wherein p53 mRNA translation is decreased by modulating a function of a p53 5'UTR. The present invention also provides a method for protecting cells of the central nervous system from cytotoxicity associated with neurodegenerative disorders in a mammal, which method comprises decreasing the level of the p53 tumor suppressor protein in the cells of the central nervous system of the mammal by decreasing the stress-induced p53 mRNA translation in said cells, wherein p53 mRNA translation is decreased by modulating a function of a p53 5'UTR. In one embodiment, the invention provides a method for preventing negative effects of a cellular stress or protecting cells of the central nervous system from cytotoxicity associated with neurodegenerative disorders in a mammal, which method comprises decreasing the level of the p53 tumor suppressor protein in the cells of the mammal by decreasing the level or activity of RPL26 in said cells. In a specific embodiment, the level or activity of RPL26 is decreased using a short interfering RNA (siRNA) molecule. In a further specific embodiment, the level or activity of RPL26 is decreased using an siRNA molecule having the sequence CCGAAAGGAUGAUGAAGUUUU (SEQ ID NO: 8). In another embodiment, the invention provides a method for preventing negative effects of a cellular stress or protecting cells of the central nervous system from cytotoxicity associated with neurodegenerative disorders in a mammal, which method comprises decreasing the level of the p53 tumor suppressor protein in the cells of the mammal by increasing the level or activity of nucleolin in said cells.

The second object of the present invention is to provide a method of screening for a compound capable of modulating the level of the p53 tumor suppressor protein in a cell, which method comprises identifying a compound capable of modulating p53 mRNA translation in the cell by affecting a function of a p53 5'UTR. Thus, in a specific embodiment, the invention provides a method of screening for a compound capable of modulating the level of the p53 tumor suppressor protein in a cell, which method comprises identifying a compound capable of modulating p53 mRNA translation in the cell by affecting a protein interaction with a p53 5'UTR. Preferably, the protein is selected from the group consisting of RPL26, nucleolin and p53.

Thus, in a separate embodiment, the invention provides a method for identifying a candidate compound useful for modulating the level of the p53 tumor suppressor protein in a cell, which method comprises: (a) contacting a first cell with a test compound under conditions sufficient to allow the cell to respond to said contact with the test compound; (b) determining in the cell prepared in step (a) a function of a p53 5'UTR; and (c) comparing the function of a p53 5'UTR determined in step (b) to the function of the p53 5'UTR in a second (control) cell that has not been contacted with the test compound; wherein a detectable change in the function of the p53 5'UTR in the first cell in response to contact with the test compound compared to the function of the p53 5'UTR in the second cell that has not been contacted with the test compound, indicates that the test compound may modulate the level of the p53 tumor suppressor protein and is a candidate compound.

In a specific embodiment, the invention provides a method for identifying a candidate compound useful for modulating the level of the p53 tumor suppressor protein in a cell, which method comprises: (a) contacting a first cell with a test compound under conditions sufficient to allow the cell to respond to said contact with the test compound; (b) determining in the cell prepared in step (a) a protein interaction with a p53 5'UTR; and (c) comparing the protein interaction with the p53 5'UTR determined in step (b) to the protein interaction with the p53 5'UTR in a second (control) cell that has not been contacted with the test compound; wherein a detectable change in the protein interaction with the p53 5'UTR in the first cell in response to contact with the test compound compared to the protein interaction with the p53 5'UTR in the second cell that has not been contacted with the test compound, indicates that the test compound may modulate the level of the p53 tumor suppressor protein and is a candidate compound. In a preferred embodiment, this screening assay of the invention is used to identify compounds that affect interaction between a p53 5'UTR and RPL26 or nucleolin or p53 and in this way are likely to be useful for modulating the level of the p53 tumor suppressor protein in a cell. Examples of screening assays that would be useful to assess interaction of RPL26 and/or nucleolin and/or p53 with the p53 5'UTR include immunoprecipitation-based PCR, in vitro RNA pull down assays, and yeast three-hybrid assays.

In conjunction with the screening methods, the present invention also provides compositions for modulating the level of the p53 tumor suppressor protein in a cell comprising a molecule capable of modulating an interaction of RPL26 or nucleolin or p53 with a p53 5'UTR. As disclosed herein, non-limiting examples of the molecules capable of modulating an interaction of RPL26 or nucleolin or p53 with the p53 5'UTR include antisense oligonucleotides, ribozymes, triple helix-forming oligonucleotides, interfering RNA molecules (e.g., short interfering RNA (siRNA) molecules or short hairpin RNA (shRNA) molecules), peptides, proteins, synthetic molecules (including various small molecules), naturally occurring molecules, and the like.

BRIEF DESCRIPTION OF THE DRAWINGS

FIGS. 2A-B. The 5'UTR of p53 mRNA in cells. A. Nucleotide sequences obtained using RLM-5'RACE from 51 clones from 100 independent clones are shown, displaying nucleotides from the 5' end of the p53 5'UTR to nucleotide 107 of 5'UTR (Nucleotide number indicates the distance from first Adenine of initiation codon). B. Schematic figure of p53 5'UTR secondary structure analyzed by the mfold computer prediction program (Zuker, et al., Nucleic Acids Research 2003, 31:3406-3415).

DETAILED DESCRIPTION OF THE INVENTION

Figure 1A:
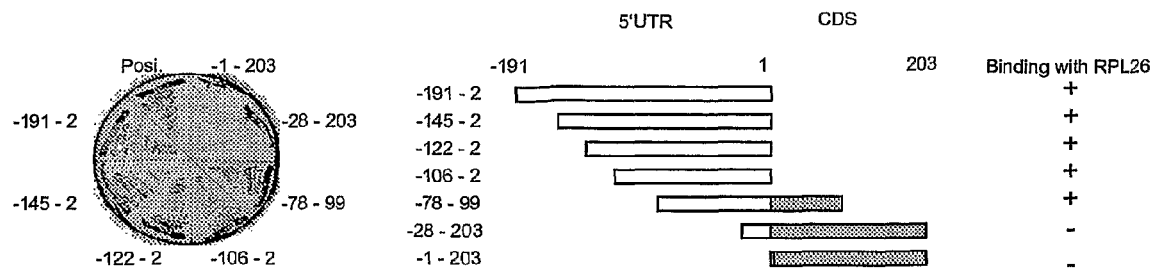
FIGS. 1A-D. Mapping RPL26 and p53 5'UTR interaction domains. A. Yeast were cotransformed with a p53 5'UTR deletion mutant (bait) and RPL26-expressing vector (prey). Posi; positive control, iron response element (IRE)/MS2 hybrid with iron regulatory protein 1(IRP). A schematic view of the deletion mutants is shown on the right. CDS: coding sequence. The first adenine of the p53 coding sequence is labeled 1. B. Capped p53 mRNA that represented several 5'UTR-deletion mutants (1, 22, 75, 146, or 192 nucleotides) was cotransfected with firefly luciferase mRNA and a GFP-RPL26 expression vector or a GFP-mock expression vector into H1299 cells and protein levels were assessed by immunoblot. Equivalence of transfection efficiency, mRNA content, and expression is indicated by the similarity of the firefly luciferase levels. C. Effects of RPL26 on p53 translation was assessed in rabbit reticulocyte lysate containing p53 cDNA's encoding several 5'UTR-deletion mutants (1, 22, 75, 146, or 192 nucleotides), firefly luciferase cDNA, and His-RPL26 or His-control cDNA. Expression of in vitro transcribed/translated p53, firefly luciferase, and His-RPL26 was assessed by immunoblotting. D. Various RPL26 deletion mutants (shown schematically on the right) were transfected into MCF7 cells and endogenous p53 levels assessed by immunoblot. The position of the KOW motif is shown.

The present invention is based on the identification of novel mechanisms involved in p53 translational regulation. As disclosed herein, translational control mechanisms are critically important in modulating cellular levels of the p53 tumor suppressor protein after DNA damage. Measurable increases in the translation of p53 mRNA after DNA damage (ionizing radiation (IR)) were documented for both wild-type and mutant p53 proteins, although increased translation rates do not result in detectably increased levels of mutant p53 protein because of its already long half-life. As further demonstrated herein, the 5'-untranslated region (5'UTR) of p53 mRNA plays an important role in regulating translation of p53 both in vitro and in vivo. Unbiased screens for proteins that specifically bind to a 5'UTR of p53 mRNA conducted by the present inventors have identified three proteins, Ribosomal Protein L26 (RPL26) (e.g., human RPL26 protein having GenBank Accession No. NP_000978; SEQ ID NO: 16), nucleolin (e.g., human nucleolin protein having GenBank Accession No. NP_005372; SEQ ID NO: 24), and p53 protein itself (e.g., human p53 protein having GenBank Accession No. NP_000537; SEQ ID NO: 25), that bind to the 5'UTR of p53 both in vitro and in cells. Manipulations of RPL26 and nucleolin demonstrated that they modulate p53 protein levels and affect p53 induction after DNA damage.

As disclosed in detail in the Examples Section, increased levels of RPL26 enhance both basal and DNA damage-induced translation of p53 mRNA in vitro and in cells and enhance cellular functions dependent on p53, such as cell cycle arrest and apoptosis. The effects of RPL26 on p53 translation require the presence of the 5'UTR. Reduction of RPL26 levels by siRNA blunt these p53-dependent responses, thus demonstrating a role for endogenous RPL26 in DNA damage responses. Nucleolin has the opposite effects on p53, with overexpression reducing basal and DNA damage-induced translation and inhibition of nucleolin enhancing translation. Taken together, the disclosed studies reveal a critical role for translational regulation of p53 protein after DNA damage and demonstrate that two novel protein regulators, RPL26 and nucleolin, can compete with each other to regulate p53 synthesis through binding to a 5'UTR of p53 mRNA.

More generally, the present invention encompasses novel methods for increasing translation of p53 as well as novel methods for decreasing translation of p53 or blocking its induction. Increasing translation of p53 using the methods of the present invention (e.g., by targeting RPL26 and nucleolin) is useful to treat various cancers characterized by existing wild-type p53 expression (e.g., neuroblastomas, lymphomas, leukemias, brain tumors, breast cancers, sarcomas, germ cell tumors, prostate cancers, eye tumors, melanomas and other skin cancers, lung cancers, cervical cancers, ovarian cancers, etc.). Decreasing translation of p53 or blocking its induction (e.g., by targeting RPL26 and nucleolin) is useful, e.g., for (i) protection from toxicities of chemotherapy, radiation therapy, unplanned radiation exposure (e.g., terrorist act), (ii) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., hyperthermia associated with fever), or in hyperthermia, (iii) inhibiting/decreasing tissue/cell aging, (iv) reducing or eliminating p53-dependent neuronal death or damage (e.g., after brain or spinal cord injury or seizure), (v) preservation of tissues and organs prior to transplanting, or (vi) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like).

For example, the present invention provides that the inhibition of nucleolin expression or activity (e.g., by shRNA having the sequence AGAGCGAGATGCGAGAACA (SEQ ID NO: 9)) increases p53 translation leading to increase in the p53-mediated apoptosis or growth arrest of cells after DNA damage. This can be useful in the treatment of tumors expressing the wild-type p53 protein, since the enhancement of p53 translation would be predicted to enhance the ability of irradiation or chemotherapy to kill these tumors. Similarly, enhancing RPL26 expression or activity (e.g., by overexpression of RPL26 or a fragment thereof, which possesses the p53 translation-augmenting activity of the full-length RPL26 (e.g., human RPL26 fragment comprising amino acids 63-90 KGQQIGKVVQVYRKKYVIYIERVQREKA (SEQ ID NO: 11)), or by overexpression of an inducer of RPL26) enhances p53 induction and p53-mediated growth arrest or cell death allowing to enhance the ability of irradiation or chemotherapy to kill tumors expressing the wild-type p53 protein.

On the other hand, the present invention provides that enhancing the expression or activity of nucleolin suppresses p53 function. Similarly, the present invention provides that inhibition of expression or activity of RPL26 (e.g., by siRNA having the sequence CCGAAAGGAUGAUGAAGUUUU (SEQ ID NO: 8)) reduces the p53-mediated apoptosis of cells after DNA damage. This would be particularly important in cells such as bone marrow progenitor cells and lymphoid cells. Thus, the toxicity of irradiation or other DNA damaging agents to bone marrow or the GI tract or the nervous system can be blunted by stimulating nucleolin or inhibiting RPL26. It also can reduce cell death in settings of tissue hypoxia where p53 is the major mediator of cell death or can reduce cytotoxicity associated with neurodegenerative disorders. Thus, a stimulator of nucleolin or an inhibitor of RPL26 could help spare tissues after hypoxic injuries (such as those that occur in heart attack and stroke) or could be used to treat neurodegenerative disorders (e.g., Huntington's Disease, Parkinson's Disease, ataxia-telangiectasia, amyotrophic lateral sclerosis (ALS) and the like).

According to the present invention, the ability of RPL26 or nucleolin or p53 to increase or decrease p53 translation can be also modulated by using fragments of p53 5'UTR which can compete with RPL26 or nucleolin or p53 for interaction with p53 5'UTR (e.g., a fragment of p53 5'UTR comprising nucleotides (nt) −22 to −1 of human p53 transcript GACTGCCTTCCGGGTCACTGCC (SEQ ID NO: 6) which can compete with RPL26 for interaction with p53 5'UTR). Such competing fragments of p53 5'UTR can be used in vivo to treat various diseases mentioned above.

Definitions

The following definitions are provided for clarity and illustrative purposes only, and are not intended to limit the scope of the invention.

Within the meaning of the present invention, the term "a function of a p53 5'UTR" encompasses all possible structural and functional interactions of a p53 5'UTR (including changes in its secondary and/or tertiary structure).

In the context of the present invention, the term "augment" means enhancing or extending the duration of a function, or both. Within the meaning of the present invention, the term "inhibit" is used to refer to any level of reduction in a function or amount of a molecule.

The terms "vector", "cloning vector" and "expression vector" mean the vehicle by which a DNA or RNA sequence can be introduced into a host cell, so as to transform the host and clone the vector or promote expression of the introduced sequence. Vectors include plasmids, cosmids, phages, viruses, etc. Vectors may further comprise selectable markers.

In the context of the present invention insofar as it relates to any of the disease conditions recited herein, the terms "treat", "treatment", and the like mean to relieve or alleviate at least one symptom associated with such condition, or to slow or reverse the progression of such condition. For example, in relation to cancer, the term "treat" may mean to relieve or alleviate at least one symptom selected from the group consisting of tumor growth, metastasis, sensitivity of tumor cells to treatments such as chemotherapy, radiation therapy, thermotherapy, etc. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject. Within the meaning of the present invention, disease conditions include without limitation various cancers which are characterized by expression of the wild-type p53 (e.g., neuroblastomas, lymphomas, leukemias, brain tumors, breast cancers, sarcomas, germ cell tumors, prostate cancers, eye tumors, melanomas and other skin cancers, lung cancers, cervical cancers, ovarian cancers), neurodegenerative disorders (e.g., Huntington's Disease, Parkinson's Disease, ataxia-telangiectasia, amyotrophic lateral sclerosis (ALS)) as well as various negative effects associated with cellular stress (e.g., (i) toxicities of chemotherapy, radiation therapy, unplanned radiation exposure, (ii) tissue/cell damage in hypoxia-reperfusion injury, oxidative stress, stresses associated with injuries, naturally occurring diseases, hyperthermia, (iii) tissue/cell aging, (iv) p53-dependent neuronal death or damage, (v) damage of tissues and organs prior to transplanting, etc.).

As used herein the term "therapeutically effective" applied to dose or amount refers to that quantity of a compound or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a disease specified above. Note that when a combination of active ingredients is administered the effective amount of the combination may or may not include amounts of each ingredient that would have been effective if administered individually. Therapeutically effective dosages according to the present invention can be determined stepwise by combinations of approaches such as (i) characterization of effective doses of the compound in in vitro assays using protein binding as a readout followed by (ii) characterization in cell cultures using p53 translation induction and/or p53 levels and/or p53-mediated apoptosis as a readout followed by (iii) characterization in animal studies using protection of tissues or enhanced tumor cell killing as a readout (depending on which direction the p53 modulation is being done), followed by (iv) characterization in human trials using tissue protection or enhanced tumor cell killing as a readout (depending on which direction the p53 modulation is being done).

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

An "antisense" nucleic acid molecule or oligonucleotide is a single stranded nucleic acid molecule, which may be DNA, RNA, a DNA-RNA chimera, or a derivative thereof, which, upon hybridizing under physiological conditions with complementary bases in an RNA or DNA molecule of interest, inhibits the expression of the corresponding gene or mRNA splice variant by inhibiting, e.g., mRNA transcription, mRNA splicing, mRNA transport, or mRNA translation or by decreasing mRNA stability. As presently used, "antisense" broadly includes RNA-RNA interactions, RNA-DNA interactions, and RNaseH mediated arrest. Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607).

Specific examples of synthetic antisense oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science, 1991, 254:1497). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; C1 to C10 lower alkyl, substituted lower alkyl, alkaryl or aralkyl; Cl; Br; CN; $CF_3$; $OCF_3$; O—; S—, or N-allyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

The term "ribozyme" is used to refer to a catalytic RNA molecule capable of cleaving RNA substrates. Ribozyme specificity is dependent on complementary RNA-RNA interactions (for a review, see Cech and Bass, Annu. Rev. Biochem. 1986; 55: 599-629). Two types of ribozymes, hammerhead and hairpin, have been described. Each has a structurally distinct catalytic center. In a specific embodiment, the present invention contemplates the use of ribozymes designed on the basis of the RPL26 or nucleolin to induce catalytic cleavage of the corresponding mRNA, thereby inhibiting expression of the RPL26 or nucleolin. Ribozyme technology is described further in Intracellular Ribozyme Applications: Principals and Protocols, Rossi and Couture ed., Horizon Scientific Press, 1999.

The term "RNA interference" or "RNAi" refers to the ability of double stranded RNA (dsRNA) to suppress the expression of a specific gene or mRNA isoform of interest in a homology-dependent manner. It is currently believed that RNA interference acts post-transcriptionally by targeting mRNA molecules for degradation. RNA interference commonly involves the use of dsRNAs that are greater than 500 bp; however, it can also be mediated through small interfering RNAs (siRNAs) or small hairpin RNAs (shRNAs), which can be 10 or more nucleotides in length and are typically 18 or more nucleotides in length. For reviews, see Bosner and Labouesse, Nature Cell Biol. 2000; 2: E31-E36 and Sharp and Zamore, Science 2000; 287: 2431-2433.

The present invention provides specific examples of RNAi molecules useful in the methods of the inventions, i.e., an RPL26-directed siRNA molecule having the sequence CCGAAAGGAUGAUGAAGUUUU (SEQ ID NO: 8) and nucleolin-directed shRNA having the sequence AGAGC-GAGATGCGAGAACA (SEQ ID NO: 9).

As used herein, the term "triplex-forming oligonucleotide" or "triple helix forming oligonucleotide" or "TFO" refers to molecules that bind in the major groove of duplex DNA and by so doing produce triplex structures. TFOs bind to the purine-rich strand of the duplex through Hoogsteen or reverse Hoogsteen hydrogen bonding. They exist in two sequence motifs, either pyrimidine or purine. According to the present invention, TFOs can be employed as an alternative to antisense oligonucleotides and can be both inhibitory and stimulatory. TFOs have also been shown to produce mutagenic events, even in the absence of tethered mutagens. TFOs can increase rates of recombination between homologous sequences in close proximity. TFOs of the present invention may be conjugated to active molecules. For review see Casey and Glazer, Prog. Nucleic Acid. Res. Mol. Biol. 2001; 67:163-92.

The above-defined antisense oligonucleotides, ribozymes, RNAi molecules and TFOs of the present invention encompass molecules that are synthetically produced and delivered to cells directly as well as molecules which are expressed within cells, e.g., using various vectors.

As used herein, the term "isolated" means that the material being referred to has been removed from the environment in which it is naturally found, and is characterized to a sufficient degree to establish that it is present in a particular sample. Such characterization can be achieved by any standard technique, such as, e.g., sequencing, hybridization, immunoassay, functional assay, expression, size determination, or the like. Thus, a biological material can be "isolated" if it is free of cellular components, i.e., components of the cells in which the material is found or produced in nature. For nucleic acid molecules, an isolated nucleic acid molecule (or isolated polynucleotide molecule), or an isolated oligonucleotide, can be a PCR product, an mRNA transcript, a cDNA molecule, or a restriction fragment. A nucleic acid molecule excised from the chromosome that it is naturally a part of is considered to be isolated. Such a nucleic acid molecule may or may not remain joined to regulatory, or non-regulatory, or non-coding regions, or to other regions located upstream or downstream of the gene when found in the chromosome. Nucleic acid molecules that have been spliced into vectors such as plasmids, cosmids, artificial chromosomes, phages and the like are considered isolated.

Isolated nucleic acid molecules of the present invention do not encompass uncharacterized clones in man-made genomic or cDNA libraries.

A protein that is associated with other proteins and/or nucleic acids with which it is associated in an intact cell, or with cellular membranes if it is a membrane-associated protein, is considered isolated if it has otherwise been removed from the environment in which it is naturally found and is characterized to a sufficient degree to establish that it is present in a particular sample. A protein expressed from a recombinant vector in a host cell, particularly in a cell in which the protein is not naturally expressed, is also regarded as isolated.

An isolated organelle, cell, or tissue is one that has been removed from the anatomical site (cell, tissue or organism) in which it is found in the source organism.

An isolated material may or may not be "purified". The term "purified" as used herein refers to a material (e.g., a nucleic acid molecule or a protein) that has been isolated under conditions that detectably reduce or eliminate the presence of other contaminating materials. Contaminants may or may not include native materials from which the purified material has been obtained. A purified material preferably contains less than about 90%, less than about 75%, less than about 50%, less than about 25%, less than about 10%, less than about 5%, or less than about 2% by weight of other components with which it was originally associated.

Methods for purification are well-known in the art. For example, nucleic acid molecules can be purified by precipitation, chromatography (including preparative solid phase chromatography, oligonucleotide hybridization, and triple helix chromatography), ultracentrifugation, and other means. Polypeptides can be purified by various methods including, without limitation, preparative disc-gel electrophoresis, isoelectric focusing, HPLC, reverse-phase HPLC, gel filtration, affinity chromatography, ion exchange and partition chromatography, precipitation and salting-out chromatography, extraction, and counter-current distribution. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. The term "substantially pure" indicates the highest degree of purity that can be achieved using conventional purification techniques currently known in the art. In the context of analytical testing of the material, "substantially free" means that contaminants, if present, are below the limits of detection using current techniques, or are detected at levels that are low enough to be acceptable for use in the relevant art, for example, no more than about 2-5% (w/w). Accordingly, with respect to the purified material, the term "substantially pure" or "substantially free" means that the purified material being referred to is present in a composition where it represents 95% (w/w) or more of the weight of that composition. Purity can be evaluated by chromatography, gel electrophoresis, immunoassay, composition analysis, biological assay, or any other appropriate method known in the art.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "modulator" refers to a compound that differentially affects the expression or activity of a gene or gene product (e.g., nucleic acid molecule or protein), for example, in response to a stimulus that normally activates or represses the expression or activity of that gene or gene product when compared to the expression or activity of the gene or gene product not contacted with the stimulus. In one embodiment, the gene or gene product the expression or activity of which is being modulated includes p53 or RPL26 or nucleolin. Examples of modulators of p53 or RPL26 or nucleolin of the present invention include without limitation a antisense oligonucleotides, ribozymes, triple helix-forming oligonucleotides, interfering RNA molecules (e.g., short interfering RNA or short hairpin RNA (shRNA) molecules), peptides, proteins, synthetic molecules (including various small molecules), naturally occurring molecules, and the like. In a specific embodiment, the invention provides a fragment of p53 5'UTR comprising nucleotides (nt) −22 to −1 of human p53 transcript GACTGCCTTCCGGGTCACTGCC (SEQ ID NO: 6) which can compete with RPL26 for interaction with p53 5'UTR. In another specific embodiment, the invention provides an siRNA molecule having the sequence CCGAAAGGAUGAUGAAGUUUU (SEQ ID NO: 8) which can modulate the level or activity of RPL26. In yet another specific embodiment, the invention provides a shRNA having the sequence AGAGCGAGATGCGAGAACA (SEQ ID NO: 9) which can modulate the level or activity of nucleolin.

Chemical agents, referred to in the art as "small molecule" compounds are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified utilizing the screening methods described below. Alternative appropriate modulators of this class are natural products, particularly secondary metabolites from organisms such as plants or fungi, which can also be identified by screening compound libraries for p53/RPL26/nucleolin-modulating activity. Methods for generating and obtaining small molecules are well known in the art (Schreiber, Science 2000; 151:1964-1969; Radmann et al., Science 2000; 151:1947-1948).

A "test compound" is a molecule that can be tested for its ability to act as a modulator of a gene or gene product. Test compounds can be selected without limitation from small inorganic and organic molecules, polypeptides (including native ligands, antibodies, antibody fragments, and other immunospecific molecules), oligonucleotides, nucleic acid molecules, and derivatives thereof. In various embodiments of the present invention, a test compound is tested for its ability to modulate the expression or activity of RPL26 or nucleolin or p53. A compound that modulates a nucleic acid or protein of interest is designated herein as a "candidate compound" or "lead compound" suitable for further testing and development. Candidate compounds include, but are not necessarily limited to, the functional categories of agonist and antagonist.

An "agonist" is defined herein as a compound that interacts with (e.g., binds to) a nucleic acid molecule or protein, and promotes, enhances, stimulates or potentiates the biological expression or function of the nucleic acid molecule or protein. The term "partial agonist" is used to refer to an agonist which interacts with a nucleic acid molecule or protein, but promotes only partial function of the nucleic acid molecule or protein. A partial agonist may also inhibit certain functions of the nucleic acid molecule or protein with which it interacts. An "antagonist" interacts with (e.g., binds to) and inhibits or reduces the biological expression or function of the nucleic acid molecule or protein.

The terms "vector", "cloning vector" and "expression vector" refer to recombinant constructs including, e.g., plasmids, cosmids, phages, viruses, and the like, with which a nucleic acid molecule can be introduced into a host cell so as to, e.g., clone the vector or express the introduced nucleic acid molecule. Vectors may further comprise selectable markers.

The terms "mutant", "mutated", "mutation", and the like, refer to any detectable change in genetic material, (e.g., DNA), or any process, mechanism, or result of such a change. Mutations include gene mutations in which the structure (e.g., DNA sequence) of the gene is altered; any DNA or other nucleic acid molecule derived from such a mutation process; and any expression product (e.g., the encoded protein) exhibiting a non-silent modification as a result of the mutation.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Therapeutic Methods of the Invention

The present invention provides novel methods for modulating the level and/or induction of the p53 tumor suppressor protein in a cell, which methods comprise modulating p53 mRNA translation in the cell by affecting a function of a p53 5'-untranslated region (5'UTR). Within the meaning of the present invention, the term "a function of a p53 5'UTR" encompasses all possible structural and functional interactions of a p53 5'UTR, including changes in its secondary and/or tertiary structure as well as interactions with various molecules (e.g., proteins, nucleic acids, ions, etc.).

In a specific embodiment, the function of a p53 5'UTR is affected by modulating protein interaction with the p53 5'UTR. In a preferred embodiment, the protein interacting with the p53 5'UTR is selected from the group consisting of Ribosomal Protein L26 (RPL26) (e.g., human RPL26 protein having GenBank Accession No. NP_000978; SEQ ID NO: 16), nucleolin (e.g., human nucleolin protein having GenBank Accession No. NP_005372; SEQ ID NO: 24), and p53 (e.g., human p53 protein having GenBank Accession No. NP_000537; SEQ ID NO: 25).

In conjunction with this embodiment, the invention also provides a method for modulating the level of the p53 tumor suppressor protein in a cell, which method comprises modulating in the cell the level or activity (including interaction with p53 5'UTR) of at least one protein selected from the group consisting of RPL26, nucleolin, and p53. In one preferred embodiment, the invention provides a method, wherein the level of the p53 tumor suppressor protein in the cell is increased by increasing the level or activity of RPL26 in the cell, including increasing the level or activity of an RPL26 fragment which possesses the p53 translation-augmenting activity of the full-length RPL26 (e.g., human RPL26 fragment comprising amino acids 63-90 KGQQIGIV-VQVYRKKYVIYIERVQREKA (SEQ ID NO: 11)). In another preferred embodiment, the invention provides a method, wherein the level of the p53 tumor suppressor protein in the cell is increased by decreasing the level or activity of nucleolin in the cell. In another preferred embodiment, the invention provides a method, wherein the level of the p53 tumor suppressor protein in the cell is decreased by decreasing the level or activity of RPL26 in the cell. In yet another preferred embodiment, the invention provides a method, wherein the level of the p53 tumor suppressor protein in the cell is decreased by increasing the level or activity of nucleolin in the cell.

According to the present invention, protein interaction (e.g., interaction of RPL26 or nucleolin or p53) with a p53 5'UTR and/or the level or activity of RPL26 or nucleolin may be modulated using a molecule selected from the group consisting of fragments of p53' 5'UTR which can compete with RPL26 or nucleolin or p53 for interaction with p53 5'UTR, antisense oligonucleotides, ribozymes, triple helix-forming oligonucleotides, interfering RNA molecules (e.g., short interfering RNA (siRNA) molecules or short hairpin RNA (shRNA) molecules), peptides, proteins, synthetic molecules (including various small molecules), naturally occurring molecules, and the like. In a specific embodiment, the invention provides a fragment of p53 5'UTR comprising nucleotides (nt) −22 to −1 of human p53 transcript GACTGCCTTCCGGGTCACTGCC (SEQ ID NO: 6) which can compete with RPL26 for interaction with p53 5'UTR. In another specific embodiment, the invention provides an siRNA molecule having the sequence CCGAAAGGAUGAUGAAGUUUU (SEQ ID NO: 8) which can modulate the level or activity of RPL26. In yet another specific embodiment, the invention provides a shRNA having the sequence AGAGCGAGATGCGAGAACA (SEQ ID NO: 9) which can modulate the level or activity of nucleolin.

As specified above, the method of the invention can be used either for increasing/inducing translation of p53 or for decreasing/blocking translation of p53. Increasing/inducing translation of p53 can lead to selectively enhancing/inducing a cell cycle arrest and apoptosis in a cell. In this way, the methods of the invention can be used for treating various cancers characterized by the existing wild-type p53 gene expression, such as neuroblastomas, lymphomas, leukemias, brain tumors, breast cancers, sarcomas, germ cell tumors, prostate cancers, eye tumors, melanomas and other skin cancers, lung cancers, cervical cancers, ovarian cancers, etc. The present invention therefore provides a method for treating a cancer in a mammal, which method comprises increasing the level of the p53 tumor suppressor protein in the cancer cells of the mammal by inducing and/or increasing p53 mRNA translation in said cells, wherein p53 mRNA translation is induced and/or increased by modulating a function of a p53 5'UTR. In a specific embodiment, the invention provides a method for treating a cancer in a mammal, which method comprises increasing the level of the p53 tumor suppressor protein in the cancer cells of the mammal by increasing the level or activity of RPL26 in said cells. In another embodiment, the invention provides a method for treating a cancer in a mammal, which method comprises increasing the level of the p53 tumor suppressor protein in the cancer cells of the mammal by decreasing the level or activity of nucleolin in said cells.

The above methods can be used in combination with various known methods for treating cancer such as therapeutic ionizing radiation, chemotherapy, etc.

Decreasing/blocking translation of p53 tumor suppressor protein can lead to selectively enhancing/inducing proliferation or preventing death of a cell. Decreasing translation of p53 or blocking its induction is useful, for example, for protection from cell killing which results from cellular stresses such as ionizing radiation, presence of a DNA damaging agent, hypoxia, hyperthermia, oxidation damage, chemical carcinogenesis, chemotherapeutic agents, UV light, etc. Accordingly, the methods of the invention can be used, for example, for (i) protection from toxicities of chemotherapy and radiation therapy (in particular, in the treatment of tumors containing mutant p53 (about 50% of all human tumors), where the decreasing/blocking p53 translation could protect the normal tissue but not affect the response of the tumor), or unplanned radiation exposure (e.g., terrorist act), (ii) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., hyperthermia associated with fever) or in hyperthermia, (iii) inhibiting/decreasing tissue/cell aging, (iv) reducing or eliminating p53-dependent neuronal death or damage (e.g., after brain or spinal cord injury or seizure), (v) preservation of tissues and organs prior to transplanting, or (vi) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like).

The present invention therefore provides a method for preventing negative effects of a cellular stress in a mammal, which method comprises decreasing the level of the p53 tumor suppressor protein in the cells of the mammal which are affected by the cellular stress by decreasing p53 mRNA translation in said cells, wherein p53 mRNA translation is decreased by modulating a function of a p53 5'UTR. In a specific embodiment, the invention provides a method for preventing negative effects of a cellular stress in a mammal, which method comprises decreasing the level of the p53 tumor suppressor protein in the cells of the mammal by decreasing the level or activity of RPL26 in said cells. In another embodiment, the invention provides a method for preventing negative effects of a cellular stress in a mammal, which method comprises decreasing the level of the p53 tumor suppressor protein in the cells of the mammal by increasing the level or activity of nucleolin in said cells.

Screening Methods of the Invention

The present invention also provides methods of screening for a compound capable of modulating the level of the p53 tumor suppressor protein in a cell, which methods comprise identifying a compound capable of modulating p53 mRNA translation in the cell by affecting a function of a p53 5'UTR. Thus, in a specific embodiment, the invention provides a method of screening for a compound capable of modulating the level of the p53 tumor suppressor protein in a cell, which method comprises identifying a compound capable of modulating p53 mRNA translation in the cell by affecting a protein interaction with a p53 5'UTR. Preferably, the protein is selected from the group consisting of RPL26, nucleolin and p53.

Thus, in a separate embodiment, the invention provides a method for identifying a candidate compound useful for modulating the level of the p53 tumor suppressor protein in a cell, which method comprises: (a) contacting a first cell with a test compound under conditions sufficient to allow the cell to respond to said contact with the test compound; (b) determining in the cell prepared in step (a) a function of a p53 5'UTR; and (c) comparing the function of a p53 5'UTR determined in step (b) to the function of the p53 5'UTR in a second (control) cell that has not been contacted with the test compound; wherein a detectable change in the function of the p53 5'UTR in the first cell in response to contact with the test compound compared to the function of the p53 5'UTR in the second cell that has not been contacted with the test compound, indicates that the test compound may modulate the level of the p53 tumor suppressor protein and is a candidate compound.

In a specific embodiment, the invention provides a method for identifying a candidate compound useful for modulating the level of the p53 tumor suppressor protein in a cell, which method comprises: (a) contacting a first cell with a test compound under conditions sufficient to allow the cell to respond to said contact with the test compound; (b) determining in the cell prepared in step (a) a protein interaction with a p53 5'UTR; and (c) comparing the protein interaction with the p53 5'UTR determined in step (b) to the protein interaction with the p53 5'UTR in a second (control) cell that has not been contacted with the test compound; wherein a detectable change in the protein interaction with the p53 5'UTR in the first cell in response to contact with the test compound compared to the protein interaction with the p53 5'UTR in the second cell that has not been contacted with the test compound, indicates that the test compound may modulate the level of the p53 tumor suppressor protein and is a candidate compound. In a preferred embodiment, this screening assay of the invention is used to identify compounds that affect interaction between a p53 5'UTR and RPL26 and/or nucleolin and/or p53 and in this way are likely to be useful for modulating the level of the p53 tumor suppressor protein in a cell.

The test compound useful in the screening assays can be, without limitation, a small organic or inorganic molecule, a polypeptide (including an antibody, antibody fragment, or other immunospecific molecule), an oligonucleotide molecule, a polynucleotide molecule, or a chimera or derivative thereof.

The screening methods of the present invention can be used to identify a candidate compounds useful to treat a condition that can be treated by modulating the translation of p53 (e.g., via modulating the interaction of p53 5'UTR with RPL26 and/or nucleolin and/or p53).

Screening assays of the invention can follow general effects on p53 translation (e.g., by following [$^{35}$S]methionine pulse-labeling of p53 protein or by measuring distribution of p53 mRNA on ribosomes by sucrose gradient centrifugation).

Methods useful for determining (and measuring changes in) interactions between RPL26, nucleolin, p53 and p53 5'UTR are well known in the art. For example, gel-shift assays can be used to measure protein-5'UTR interactions (e.g., between recombinant tagged protein with the labeled p53 5'UTR). Simple gel-shift assays may be followed by super-shift assays using protein-specific antibodies. Interaction between p53 5'UTR and proteins can be also detected and quantitated by RNA pull-down (co-immunoprecipitation) assays with biotinylated p53 5'UTR (e.g., followed by western blotting using protein-specific antibodies). Alternatively, immunoprecipitation assays can be used, where transfected tagged proteins are immunoprecipitated, or where endogenous RPL26 or nucleolin is immunoprecipitated followed by detecting the presence of p53 mRNA by RT-PCR using a p53 5'UTR-specific primer.

More generally, to identify RPL26- or nucleolin-interacting molecules (e.g., ligands, agonists or antagonists), RPL26 or nucleolin protein or biologically active fragments thereof (e.g., human RPL26 fragment comprising amino acids 63-90 KGQQIGKVVQVYRKKYVIYIERVQREKA (SEQ ID NO: 11) as disclosed in the Examples Section, below) can be labeled with $^{125}$I Bolton-Hunter reagent (Bolton et al, Biochem. J. 1973; 133:529-539). Candidate molecules previously arrayed in the wells of a multi-well plate can be incubated with the labeled RPL26 or nucleolin or a fragment thereof, washed, and any wells with labeled complex can be assayed. Data obtained using different concentrations of RPL26 or nucleolin can be used to calculate values for the number, affinity, and association of RPL26 or nucleolin with the candidate molecules.

Molecules that interact with RPL26 or nucleolin in vivo can be also identified by co-immunoprecipitation (e.g., using antibodies against RPL26 and nucleolin or tag-specific antibodies or interacting compounds) or affinity chromatography (e.g., using immobilized RPL26 or nucleolin or its fragment) from cultured cells or tissue lysate. To detect transient interactions, co-immunoprecipitation can be performed after in vivo crosslinking (e.g., using formaldehyde). Co-immunoprecipitated or affinity-purified molecules can be further identified using SDS-PAGE and mass spectrometry as described in recent reviews (Wu et al., Nature Biotech. 2003; 21:262-267; Graves et al., Microbiol. Mol. Biol. Rev. 2002; 66:39-63)

The present invention also provides a method of identifying peptide ligands that bind to RPL26 or nucleolin by phage display method. In phage display, the fusion proteins are incorporated into phage particles such that the particles display the candidate RPL26- or nucleolin-binding peptide on the surface of the phage particle. For example, The Ph.D.-7 Phage Display Peptide Library (Cat#E8100S, New England BioLab, Inc, Beverly, Mass.) is based on a combinatorial library of random heptapeptides fused to a minor coat protein (pIII) of M13 phage. A library of fusion proteins created and displayed on phage particles can be "panned" against a RPL26 or nucleolin target (which can be a fragment of RPL26 or nucleolin protein) to identify the candidate peptides that bind to specific RPL26 or nucleolin domains. Phages displaying RPL26 or nucleolin-binding peptides are then isolated, and the sequence of the displayed peptide is determined, for example, by sequencing the fusion gene. The sequence of one or more binding peptides can then be compared to the carboxyl-terminal sequences of known proteins to determine which known intracellular proteins have a carboxyl-terminal sequence identical to or similar to the RPL26 or nucleolin-binding peptide(s) to identify cognate protein ligands for the RPL26 or nucleolin.

RPL26- or nucleolin- or p53 5'UTR-interacting molecules can be identified and binding interactions between candidate compounds, RPL26 and/or nucleolin and p53 5'UTR can be evaluated using yeast three-hybrid screens (e.g., as described in the Examples Section, below; see also Bernstein et al., Methods 2002; 26:123-141 and SenGupta et al., Proc. Natl. Acad. Sci. U.S.A 1996; 93:8496-8501). Alternatively, interaction with RPL26 or nucleolin can be evaluated in the absence of p53 5'UTR using the yeast two-hybrid system described in Fields et al., Nature 1989; 340:245-246 and Fields et al., Trends in Genetics 1994; 10:286-292 (see also Vidal et al, Nucleic Acids Res. 1999; 27:919-29), or by using commercially available kits based on the two-hybrid system, such as the MATCHMAKER system (Clontech). Expression of the reporter gene can be monitored as different test agents are added to the system. The presence of an inhibitory agent, for example, will result in lack of or reduction in a reporter signal. In a high-throughput format, yeast three-hybrid and two-hybrid screens can be performed using large libraries of genes (U.S. Pat. No. 6,057,101).

As disclosed in the Examples Section, below, the in vitro translation system (e.g., rabbit reticulocyte lysate system) can be used to study the regulation of p53 translation by adding RPL26 or nucleolin or a biologically active fragment thereof. This system can be modified to be used as a screen for compounds that affect p53 translation through the 5'UTR. A reporter assay using the 5'UTR linked to a reporter gene in cells could be used in this type of modified screen to identify compounds that affect p53 translation.

Modulator screens can be designed to identify stimulatory and/or inhibitory agents. The sources for potential agents to be screened include natural sources, such as a cell extract (e.g., animal, bacterial, fungal, algal, insect, or plant) and synthetic sources, such as chemical compound libraries. Binding assays can be used to detect RPL26 and nucleolin binding activity to peptide or non-peptide ligands. Both functional and binding assays of RPL26 and nucleolin activity are readily adapted to screens for modulators such as agonists or antagonists.

Screening assays of the invention can be performed in high-throughput and array formats. High-throughput screening (HTS) assays useful in the screening methods of the present invention include cell-based and cell-free assays, directed against individual protein targets. Several methods of automated assays that have been developed in recent years enable the screening of tens of thousands of compounds in a short period of time (see, e.g., U.S. Pat. Nos. 5,585,277, 5,679,582, and 6,020,141). Such HTS methods are particularly preferred.

Candidate compounds to be tested as modulators can be selected from chemical compounds, including libraries of chemical compounds. There are a number of different libraries that can be used for the identification of small molecule modulators, including: (1) chemical libraries, (2) natural product libraries, and (3) combinatorial libraries comprised of random peptides, oligonucleotides or organic molecules. For reviews, see Science 1998; 282:63-68 and Myers, Curr. Opin. Biotechnol. 1997; 8:701-707.

Aptamers are short oligonucleotide sequences that can be used to recognize and specifically bind almost any molecule. The systematic evolution of ligands by exponential enrichment (SELEX) process (Ellington et al., Nature 1990; 346: 818-22; Tuerk et al., Science 1990; 249:505-10) can be used to find such aptamers.

Many general methods are known and can be used to identify the binding affinities of RPL26 or nucleolin binding ligands (e.g., peptides, proteins, small molecules, etc.). For example, binding affinities can be determined as $IC_{50}$ values using competition ELISAs (using avidin-biotin based systems or ligands chemically-linked to a substrate or ligands absorbed to a substrate).

It is now becoming increasingly recognized, that the agonist-bound proteins can form ternary complexes with other ligands or "accessory" proteins and display altered binding and/or signaling properties in relation to the binary agonist-receptor complex. Accordingly, allosteric sites on the RPL26 or nucleolin protein represent novel modulator targets and potential drug targets since allosteric modulators possess a number of theoretical advantages over classic orthosteric ligands. Because of the noncompetitive nature of allosteric phenomena, the detection and quantification of such effects often relies on a combination of equilibrium binding, non-equilibrium kinetic, and functional signaling assays. For review see, e.g., Christopoulos et al., Pharmacological Reviews 2002; 54:323-74.

Small molecules that can act as RPL26 or nucleolin ligands can be further optimized using classical ligand-based design approaches (such as, e.g., virtual screening, pharmacophore modeling, quantitative structure-activity relationship (QSAR), etc.) as well as by synthesizing combinatorial libraries (for review see, e.g., Klabunde et al., Chembiochem. 2002; 3:928-44).

Cell-based arrays combine the technique of cell culture in conjunction with the use of fluidic devices for measurement of cell response to test compounds in a sample of interest, screening of samples for identifying molecules that induce a desired effect in cultured cells, and selection and identification of cell populations with novel and desired characteristics. High-throughput screens (HTS) can be performed on fixed cells using fluorescent-labeled antibodies, biological ligands and/or nucleic acid hybridization probes, or on live cells using multicolor fluorescent indicators and biosensors. The choice of fixed or live cell screens depends on the specific cell-based assay required.

There are numerous single- and multi-cell-based array techniques known in the art. Recently developed techniques such as micro-patterned arrays (described, e.g., in International PCT Publications WO 97/45730 and WO 98/38490) and microfluidic arrays provide valuable tools for comparative cell-based analysis. Transfected cell microarrays are a complementary technique in which array features comprise clusters of cells overexpressing defined cDNAs. Complementary DNAs cloned in expression vectors are printed on microscope slides, which become living arrays after the addition of a lipid transfection reagent and adherent mammalian cells (Bailey et al., Drug Discov. Today 2002; 7(18 Suppl): S113-8). Cell-based arrays are described in detail in, e.g., Beske, Drug Discov. Today 2002; 7(18 Suppl):S131-5; Sundberg et al., Curr. Opin. Biotechnol. 2000; 11:47-53; Johnston et al., Drug Discov. Today 2002; 7:353-63; U.S. Pat. Nos. 6,406,840 and 6,103,479, and U.S. published patent application No. 2002/0197656. For cell-based assays specifically used to screen for modulators of ligand-gated ion channels, see Mattheakis et al, Curr. Opin. Drug Discov. Devel. 2001; 1:124-34; and Baxter et al., *J. Biomol. Screen.* 2002; 7:79-85.

Protein arrays are solid-phase, ligand binding assay systems using immobilized proteins on surfaces that are selected from glass, membranes, microtiter wells, mass spectrometer plates, and beads or other particles. The ligand binding assays using these arrays are highly parallel and often miniaturized. Their advantages are that they are rapid, can be automated, are capable of high sensitivity, are economical in their use of reagents, and provide an abundance of data from a single experiment.

Automated multi-well formats are the best-developed HTS systems. Automated 96-well plate-based screening systems are the most widely used. The current trend in plate based screening systems is to reduce the volume of the reaction wells further, thereby increasing the density of the wells per plate (96 wells to 384 wells, and 1,536 wells per plate). The reduction in reaction volumes results in increased throughput, dramatically decreased bioreagent costs, and a decrease in the number of plates that need to be managed by automation. For a description of protein arrays that can be used for HTS, see, e.g., U.S. Pat. Nos. 6,475,809; 6,406,921; and 6,197,599; and International Publications No. WO 00/04389 and WO 00/07024.

For construction of arrays, sources of proteins include cell-based expression systems for recombinant proteins, purification from natural sources, production in vitro by cell-free translation systems, and synthetic methods for peptides. For capture arrays and protein function analysis, it is important that proteins are correctly folded and functional. This is not always the case, e.g., where recombinant proteins are extracted from bacteria under denaturing conditions, whereas other methods (isolation of natural proteins, cell free synthesis) generally retain functionality. However, arrays of denatured proteins can still be useful in screening antibodies for cross-reactivity, identifying auto-antibodies, and selecting ligand binding proteins.

The immobilization method used should be reproducible, applicable to proteins of different properties (size, hydrophilic, hydrophobic), amenable to high throughput and automation, and compatible with retention of fully functional protein activity. Both covalent and non-covalent methods of protein immobilization can be used. Substrates for covalent attachment include, e.g., glass slides coated with amino- or aldehyde-containing silane reagents (Telechem). In the Versalinx™ system (Prolinx), reversible covalent coupling is achieved by interaction between the protein derivatized with phenyldiboronic acid, and salicylhydroxamic acid immobilized on the support surface. Covalent coupling methods providing a stable linkage can be applied to a range of proteins. Non-covalent binding of unmodified protein occurs within porous structures such as HydroGel™ (PerkinElmer), based on a 3-dimensional polyacrylamide gel.

For detection of molecules using screening assays, a molecule (e.g., an antibody or polynucleotide probe) can be detectably labeled with an atom (e.g., radionuclide), detectable molecule (e.g., fluorescein), or complex that, due to its physical or chemical property, serves to indicate the presence of the molecule. A molecule can also be detectably labeled when it is covalently bound to a "reporter" molecule (e.g., a biomolecule such as an enzyme) that acts on a substrate to produce a detectable product. Detectable labels suitable for use in the present invention include any composition detectable by spectroscopic, photochemical, biochemical, immunochemical, electrical, optical or chemical means. Labels useful in the present invention include, but are not limited to, biotin for staining with labeled avidin or streptavidin conjugate, magnetic beads (e.g., Dynabeads™), fluorescent dyes (e.g., fluorescein, fluorescein-isothiocyanate (FITC), Texas red, rhodamine, green fluorescent protein, enhanced green fluorescent protein, lissamine, phycoerytllrin, Cy2, Cy3, Cy3.5, Cy5, Cy5.5, Cy7, FluorX [Amersham], SyBR™ Green I & II [Molecular Probes], and the like), radiolabels (e.g., $^3H$, $^{125}I$, $^{35}S$, $^{14}C$, or $^{32}P$), enzymes (e.g., hydrolases, particularly phosphatases such as alkaline phosphatase, esterases and glycosidases, or oxidoreductases, particularly peroxidases such as horse radish peroxidase, and the like), substrates, cofactors, inhibitors, chemiluminescent groups, chromogenic agents, and colorimetric labels such as colloidal gold or colored glass or plastic (e.g., polystyrene, polypropylene, latex, etc.) beads. Examples of patents describing the use of such labels include U.S. Pat. Nos. 3,817,837; 3,850,752; 3,939,350; 3,996,345; 4,277,437; 4,275,149; and 4,366,241.

Means of detecting such labels are known to those of skill in the art. For example, radiolabels and chemiluminescent labels can be detected using photographic film or scintillation counters; fluorescent markers can be detected using a photodetector to detect emitted light (e.g., as in fluorescence-activated cell sorting); and enzymatic labels can be detected by providing the enzyme with a substrate and detecting, e.g., a colored reaction product produced by the action of the enzyme on the substrate.

Proteins of the Invention

In conjunction with the therapeutic and screening methods, the present invention provides proteins useful in these methods. Specifically, the invention provides Ribosomal Protein L26 (RPL26) and nucleolin, which are useful to modulate the translation of p53 tumor suppressor protein. In a preferred embodiment, the human proteins are used, e.g., human RPL26 protein having GenBank Accession No. NP_000978 (SEQ ID NO: 16) and human nucleolin protein having GenBank Accession No. NP_005372 (SEQ ID NO: 24). However, any other orthologs of these proteins can be also used. These orthologs can be known proteins or novel orthologs determined, e.g., by sequence comparison algorithms such as BLAST (e.g., BLAST program from the National Center for Biotechnology Information (NCBI—Version 2.2), available on the WorldWideWeb at ncbi.nlm.nih.gov/BLAST/), FASTA, DNA Strider, and GCG.

In addition to the use of whole-length RPL26 and nucleolin, their fragments, mutants and/or tagged versions can be also used. These fragments, mutants and tagged versions can either have the same or similar activity as whole-length protein (which makes them useful as detectable alternatives), can have lower or no activity (which makes them useful as negative controls), or can have a dominant-negative activity (which makes them useful as competitors). As demonstrated in the Examples Section, below, a central domain of RPL26 corresponding to amino acids 63-90 KGQQIGKV-VQVYRKKYVIYIERVQREKA (SEQ ID NO: 11) (overlapping with the Kyrpides-Ouzounis-Woese (KOW) motif RKDDEVQVVRGHYKGQQIGKVVQVYRK (SEQ ID NO: 10) [see also Kyrpides et al., Trends Biochem. Sci. 1996; 21:425-426]) is particularly important in RPL26 regulatory effect on p53 translation. Accordingly, RPL26 fragments comprising this central domain (e.g., RPL26 fragments corresponding to amino acids 2-89, 46-145, 63-145, and 45-116 disclosed in the Examples Section, below) can be used to investigate the effect of RPL26 on the p53 translation, or to analyze interactions with p53 5'UTR and/or with other proteins affecting p53 translation (e.g., nucleolin or p53).

The invention further provides that fragments of RPL26 that have stimulatory effect on p53 translation can be used to increase p53 activity in vivo for treating cancers. The invention further provides that fragments of RPL26 that have dominant-negative effect on p53 translation (e.g., mutant fragments) can be used to decrease p53 activity in vivo for (i) protection from toxicities of chemotherapy, radiation therapy, unplanned radiation exposure (e.g., terrorist act), (ii) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., hyperthermia associated with fever) or in hyperthermia, (iii) inhibiting/decreasing tissue/cell aging, (iv) reducing or eliminating p53-dependent neuronal death or damage (e.g., after brain or spinal cord injury or seizure), (v) preservation of tissues and organs prior to transplanting, or (vi) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like).

As disclosed in detail in the Screening Methods Section, above, additional proteins which modulate p53 translation by interacting with p53 5'UTR and/or with RPL26 and/or with nucleolin can be identified using various methods well known in the art.

For example, additional proteins which interact with p53 5'UTR can be identified using yeast two-hybrid and three-hybrid screens, e.g., as described in the Examples Section, below (see also Fields et al, Nature 1989; 340:245-246; Fields et al., Trends in Genetics 1994; 10:286-292; Vidal et al., Nucleic Acids Res. 1999; 27: 919-29; Bernstein et al., Methods 2002; 26:123-141 and SenGupta et al., Proc. Natl. Acad. Sci. U.S.A 1996; 93:8496-8501). Alternatively, such additional proteins interacting with p53 5'UTR can be identified using gel-shift assays with labeled p53 5'UTR or RNA pull-down (co-immunoprecipitation) assays or immunoprecipitation assays followed by detecting the presence of p53 mRNA by RT-PCR using a p53 5'UTR primer. In immunoprecipitation-based assays, unknown immunoprecipitated proteins can be identified, e.g., using mass spectrometry.

To further identify whether the candidate proteins interact directly with the '5 UTR of the p53 transcript or indirectly as part of the nucleoprotein complex, in vitro specific binding can be monitored by electrophoretic mobility gel shift assays (EMSA) (see, e.g., Sarge et al., Mol. Cell. Biol. 1993; 13:1392-1407).

For additional assays for identification of proteins interacting with p53 5'UTR as well as proteins interacting with RPL26 and/or with nucleolin see the Screening Assay Section, above.

To identify whether the candidate protein interacting with p53 5'UTR and/or with RPL26 and/or with nucleolin affects p53 translation, [$^{35}$S]methionine pulse-labeling can be used. If addition (in vitro) or transfection (in vivo) of a candidate molecule directly increases p53 translation in a dose-dependent manner and does not have the same effect on overall cellular translation levels, the effect of the candidate on p53 translation can be concluded. Activation of p53 translation (as compared to other cellular proteins) can be also assessed by measuring distribution of p53 mRNA on ribosomes by sucrose gradient centrifugation. Assays using luciferase reporters containing p53 5'UTR and 3'UTR can be used for measuring p53 translation levels.

For use in the methods of the present invention, proteins of the invention or their fragments can be produced as fusion molecules carrying purification or detection tags such as, e.g., EGFP, GFP, His$_n$, FLAG, etc.

To determine domains and residues in proteins of the invention which are critical for interactions with p53 5'UTR and/or with RPL26 and/or with nucleolin, mutagenesis analysis can be performed. For example, alanine scanning can be performed. In this method, residues are substituted with a single amino acid, typically an alanine residue, and the effect on protein function and/or interactions is assessed. See U.S. Pat. Nos. 5,580,723; 5,834,250. Another useful method is construction of series of truncations (deletions). A series of truncations may be prepared by truncating the amino terminal amino acids sequentially; in another series, the truncations may begin at the carboxy terminus. As in the case for alanine scanning, the peptides may be synthesized in vitro or prepared by recombinant methods. Creating a series of truncations allows not only to elucidate residues critical for protein function and/or interactions, but also to determine the minimal length of peptide to achieve proper protein function and/or interactions. In some cases, truncation will reveal a peptide that binds more tightly than the native protein such a peptide may be useful to inhibit protein function and/or interactions iii vivo.

Based on the information obtained from alanine scanning and truncation analysis, the skilled artisan can design and synthesize small molecules, or select small molecule libraries that are enriched in molecules that affect function and/or interactions of the proteins of the invention.

Nucleic Acids of the Invention

In conjunction with the methods and proteins of the invention, the invention provides various nucleic acid molecules. These nucleic acid molecules can be classified into the following groups: (i) nucleic acids corresponding to p53 transcripts, including nucleic acids corresponding to p53 5'UTR or complements or fragments thereof; (ii) nucleic acids encoding the proteins of the invention and fragments thereof, and (iii) nucleic acids affecting expression and/or function of the proteins of the invention.

Among the nucleic acids corresponding to p53 5'UTR, the present invention provides, for example, nucleic acids comprising (i) nucleotides (nt) −139 to 1 of the p53 transcript, which, in the case of human p53, corresponds to AAAAGTCTAGAGCCACCGTCCAGGGAG-CAGGTAGCTGCTGGGCTCCGGGGACACTT TGCGT-TCGGGCTGGGAGCGTGCTTTCCACGACG-GTGACACGCTTCCCTGGATTGGC AGCCAGACTGCCTTCCGGGTCACTGCC (SEQ ID NO: 1); (ii) nucleotides (nt) −75 to 1 of the p53 transcript, which, in the case of human p53, corresponds to GGCTGG-GAGCGTGCTTTCCACGACGGTGA-CACGCTTCCCTGGATTGGCAGCCAGAC TGCCTTC-CGGGTCACTGCC (SEQ ID NO: 2); (iii) nucleotides (nt) −190 to 1 of the p53 transcript, which, in the case of human p53, corresponds to GTTTTCCCCTCCCATGTGCT-CAAGACTGGCGCTAAAAGTTTTGAGCT-TCTCAAAAGT CTAGAGCCACCGTCCAGGGAGCAG-GTAGCTGCTGGGCTCCGGGGACACTTTGCGTT CGGGCTGGGAGCGTGCTTTCCACGACG-GTGACACGCTTCCCTGGATTGGCAGCCAG ACTGC-CTTCCGGGTCACTGCC (SEQ ID NO: 3). In another embodiment, the invention provides nucleic acids comprising a stem loop structure of p53 5'UTR, which, in the case of human p53, comprises at least a part of the sequence GTTTTCCCCTCCCATGTGCTCAAGACTG-GCGCTAAAAGTTTTGAGCTTCTCAAAAGT CTA-GAGCCACCGTCCAGGGAGCAGGTAGCT-GCTGGGCTCCGGGGACACTTTGCGTT CGGGCTGGGAGCGTGCTTTCCACGACG-GTGACACGCTTCCCTGGATTGGCAGCCAG ACTGC-CTTCCGGGTCACTGCC (SEQ ID NO: 4).

The invention contemplates additional p53 5'UTR sequences, including sequences up to 251 nucleotides in length (as identified by the National Center of Biotechnology Information (NCBI) online data base available on the WorldWideWeb at ncbi.nlm.nih.gov/; see, e.g., GenBank Accession No. NM_000546; corresponding to the sequence ACTTGT-CATGGCGACTGTCCAGCTTTGTGCCAG-GAGCCTCGCAGGGGTTGATGGGA TTGGGGTTTTC-CCCTCCCATGTGCTCAAGACTGGCGCTAAAAGTTTT GAGCTTCTCA AAAGTCTAGAGCCACCGTCCAGG-GAGCAGGTAGCTGCTGGGCTCCGGGGACACTTT GCGTTCGGGCTGGGAGCGTGCTTTCCAC-GACGGTGACACGCTTCCCTGGATTGGCA GCCA-GACTGCCTTCCGGGTCACTGCC (SEQ ID NO: 12) as well as various shorter fragments of p53 5'UTR disclosed in the Examples Section and FIG. 2A (see also Tuck et al., Mol. Cell. Biol. 1989; 9:2163-2172). As specified in the Examples Section, below, useful fragments of p53 5'UTR which are capable of supporting p53 translation (or competing for p53 translational regulators) comprise nucleotides (nt) −22 to −1 of human p53 transcript GACTGCCTTCCGGGTCACT-GCC (SEQ ID NO: 6).

According to the present invention, fragments of the p53 5'UTR that can compete with native p53 mRNA for interaction with the regulators of p53 translation, can be used in vivo to modulate p53 translation and to treat various diseases treatable by affecting p53 translation.

When used in the screening methods of the present invention, various lengths of the 5'UTR can be attached to the full-length p53 coding sequence with a full-length 3'UTR and poly (A) sequence or to a reporter transcript such as a GFP or luciferase.

Using the yeast three-hybrid system or in vitro transcription/translation system (e.g., rabbit reticulocyte lysate) or functional co-transfection assays of candidate proteins with constructs containing various lengths of p53 5'UTR (e.g., as disclosed in the Examples Section, below), specific p53 5

Figure 1B:
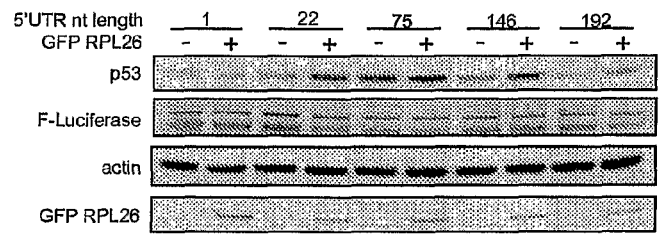
Figure 1C:
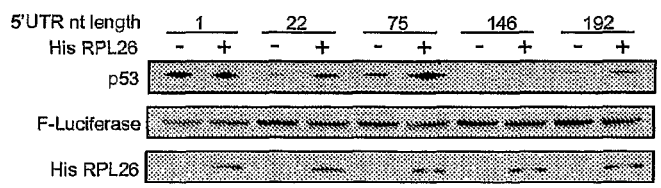

'UTR regions responsible for interaction with candidate proteins can be mapped. For example, as specified in the Examples Section, below, using the yeast three-hybrid system, it was determined that RPL26 binds to a region including p53 5'UTR nucleotides −78 to −1 TCGGGCTGGGAGCGTGCTTTCCACGACGGTGACACGCTTCCCTGGATTGGCAGCCA GACTGCCTTCCGGGTCACTGCC (SEQ ID NO: 5) (FIG. 1A), and using functional co-transfection assay it was determined that at least nucleotides −22 to −1 GACTGCCTTCCGGGTCACTGCC (SEQ ID NO: 6) are required for RPL26-mediated p53 translational increase (FIG. 1B).

The invention further provides nucleic acids encoding Ribosomal Protein L26 (RPL26) and nucleolin (e.g., human RPL26 mRNA having GenBank Accession No. NM_000987 and human nucleolin mRNA having GenBank Accession No. NM_005381). In a preferred embodiment, the invention provides nucleic acids encoding the human RPL26 and nucleolin proteins. In addition to nucleic acids encoding the whole-length RPL26 and nucleolin proteins, the invention further provides nucleic acids encoding their fragments, mutants and/or tagged versions thereof. As disclosed above, these fragments, mutants and tagged versions can either have the same or similar activity as whole-length protein (which makes them useful as detectable alternatives), can have lower or no activity (which makes them useful as negative controls), or can have a dominant-negative activity (which makes them useful as competitors).

The invention additionally provides nucleic acids affecting expression and/or function of the proteins of the invention. Among nucleic acids affecting expression and/or function-of the proteins of the invention, the present invention provides various antisense oligonucleotides, ribozymes, triple helix-forming oligonucleotides, interfering RNA molecules (e.g., short interfering RNA (siRNA) molecules or short hairpin RNA (shRNA) molecules), and the like. For example, as disclosed in the Examples Section, below, interaction of human RPL26 with a human p53 5'UTR and the level of human RPL26 may be modulated using siRNA having sequence CCGAAAGGAUGAUGAAGUUUU (SEQ ID NO: 8), and interaction of human nucleolin with a human p53 5'UTR and the level of nucleolin may be modulated using shRNA having sequence AGAGCGAGATGCGAGAACA (SEQ ID NO: 9).

Compositions of the Invention

In conjunction with the therapeutic and screening methods, proteins and nucleic acids, the present invention also provides pharmaceutical and therapeutic compositions for modulating the level of the p53 tumor suppressor protein in a cell comprising a molecule capable of modulating an interaction of RPL26 or nucleolin or p53 with a p53 5'UTR.

Such molecules capable of modulating an interaction of RPL26 or nucleolin or p53 with a p53 5'UTR can be advantageously formulated in a pharmaceutical composition with a pharmaceutically acceptable carrier. The candidate compound may be designated as an active ingredient or therapeutic agent for the treatment of cancer, cell/tissue stress, or other indication.

The concentration of the active ingredient depends on the desired dosage and administration regimen. Suitable dose ranges of the active ingredient are from about 0.01 mg/kg to about 1500 mg/kg of body weight per day.

Therapeutically effective compounds can be provided to the patient in standard formulations, and may include any pharmaceutically acceptable additives, such as excipients, lubricants, diluents, flavorants, colorants, buffers, and disintegrants. The formulation may be produced in useful dosage units for administration by oral, parenteral, transmucosal, intranasal, rectal, vaginal, or transdermal routes. Parental routes include intravenous, intra-arteriole, intramuscular, intradermal, subcutaneous, intraperitoneal, intraventricular, intrathecal, and intracranial administration.

For the treatment of cancers and other hyperproliferative disorders, the pharmaceutical composition may also include other biologically active substances in combination with the candidate compound. Such substances include but are not limited to anticancer agents, for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins.

For the treatment of diseases and conditions resulting from cellular stress, the pharmaceutical composition comprising the candidate compound may be combined with other biologically active substances or treatment regimes. Such substances or treatments include but are not limited to measures including changes in diet, for example, increased intake of fruit and vegetables, and supplementation of the diet with phytochemicals or antioxidants, such as vitamin B12. It may be desirable to combine the compositions of the invention with other agents effective in the treatment of diseases and conditions resulting from cellular stress (secondary therapy). For example, the treatment of stroke (antistroke treatment) typically involves an antiplatelet (aspirin, clopidogrel, dipyridamole, ticlopidine), an anticoagulant (heparin, warfarin), or a thrombolytic (tissue plasminogen activator). Such secondary therapy measures may also include administration of drugs with antioxidant activity such as methylprednisolone, 21-aminosteroids, 2-methylaminochromans, pyrrolopyrimidines and thiazolidinones.

The pharmaceutical compositions of the invention may comprise any treatment in combination with the candidate compound that treats diseases and conditions resulting from cellular stress. Cellular stresses include ionizing radiation, presence of a DNA damaging agent, hypoxia, hyperthermia, oxidation damage, chemical carcinogenesis, chemotherapeutic agents, UV light, etc. Accordingly, the pharmaceutical compositions of the invention may additionally comprise any treatment useful, for example, for (i) protection from toxicities of chemotherapy, radiation therapy, unplanned radiation exposure (e.g., terrorist act), (ii) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., hyperthermia associated with fever) or in hyperthermia, (iii) inhibiting/decreasing tissue/cell aging, (iv) reducing or eliminating p53-dependent neuronal death or damage (e.g., after brain or spinal cord injury or seizure), (v) preservation of tissues and organs prior to transplanting, or (vi) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like).

In one embodiment, the active ingredient can be delivered in a vesicle, particularly a liposome or a viral vector (e.g., retrovirus, lentivirus, adenovirus, or adeno-associated virus-based vectors). In another embodiment, the therapeutic agent can be delivered in a controlled release manner. For example, a therapeutic agent can be administered using intravenous infusion with a continuous pump, in a polymer matrix such as poly-lactic/glutamic acid (PLGA), in a pellet containing a mixture of cholesterol and the active ingredient (SilasticR™; Dow Corning, Midland, Mich.; see U.S. Pat. No. 5,554,601), by subcutaneous implantation, or by transdermal patch.

To produce specific effect on the cells under stress or neurodegenerated tissues or on cancer cells, compositions of the present invention can be delivered systemically. If targeted delivery to cancer cells is desirable, conjugates or vesicles or viral vectors containing antibodies to tumor-specific antigens can be used. Alternately, viral vectors can be injected directly into cancerous tissues. In case of cells of the central nervous system, compositions of the invention can be also delivered directly to the area through injections or into the cerebrospinal fluid.

Antibodies of the Invention

As used herein, the term "antibody" refers to a human, nonhuman, or chimeric (e.g., humanized) immunoglobulin, or binding fragment thereof, that specifically binds to an antigen, e.g., RPL26 or nucleolin protein. Suitable antibodies may be polyclonal (e.g., sera or affinity purified preparations), monoclonal, or recombinant. Examples of useful fragments include separate heavy chains, light chains, Fab, F(ab')$_2$, Fabc, and Fv fragments. Fragments can be produced by enzymatic or chemical separation of intact immunoglobulins or by recombinant DNA techniques. Fragments may be expressed in the form of phage-coat fusion proteins (see, e.g., International PCT Publication Nos. WO 91/17271, WO 92/01047, and WO 92/06204). Typically, the antibodies, fragments, or similar binding agents bind a specific antigen with an affinity of at least $10^7$, $10^8$, $10^9$, or $10^{10}$ M$^{-1}$.

The present invention provides isolated antibodies directed against polypeptides of the invention. In a specific embodiment, antibodies can be raised against a RPL26 or nucleolin protein of the invention using known methods in the art. The Examples Section below describes two specific rabbit polyclonal antibodies generated against human RPL26: antibody generated against KLH-conjugated RPL26 peptide SKNRKRHFNAPSHIRRKI (corresponding to RPL26 N-terminal amino acids 12-29; SEQ ID NO: 26) and antibody generated against KLH-conjugated RPL26 peptide RQVGKEKGKYKEETIEK (corresponding to RPL26 C-terminal amino acids 126-142; SEQ ID NO: 27).

For antibody generation, various host animals selected, e.g., from pigs, cows, horses, rabbits, goats, sheep, rats, or mice, can be immunized with a partially or substantially purified target protein, or with a peptide homolog, fusion protein, peptide fragment, analog or derivative thereof. An adjuvant can be used to enhance antibody production.

Polyclonal antibodies can be obtained and isolated from the serum of an immunized animal and tested for specificity against the antigen using standard techniques. Alternatively, monoclonal antibodies can be prepared and isolated using any technique that provides for the production of antibody molecules by continuous cell lines in culture. These include but are not limited to the hybridoma technique originally described by Kohler and Milstein, *Nature* 1975; 256: 495-497; the human B-cell hybridoma technique (Kosbor et al., Immunology Today 1983; 4:72; Cote et al., Proc. Natl. Acad. Sci. USA 1983; 80:2026-2030); and the EBV-hybridoma technique (Cole et al., Monoclonal Antibodies and Cancer Therapy, Alan R. Liss, Inc., 1985, pp. 77-96). Alternatively, techniques described for the production of single chain antibodies (see, e.g., U.S. Pat. No. 4,946,778) can be adapted.

Antibody fragments that contain specific binding sites for a polypeptide of the present invention are also encompassed within the present invention, and can be generated by known techniques. Such fragments include but are not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab expression libraries can be constructed (Huse et al, Science 1989; 246:1275-1281) to allow rapid identification of Fab fragments having the desired specificity to the particular protein.

Techniques for the production and isolation of monoclonal antibodies and antibody fragments are known in the art, and are generally described, among other places, in Harlow and Lane, *Antibodies: A Laboratory Manual*, Cold Spring Harbor Laboratory, 1988, and in Goding, *Monoclonal Antibodies: Principles and Practice*, Academic Press, London, 1986.

Antibodies or antibody fragments of the invention can be used in methods known in the art relating to the localization and activity of proteins of the invention, e.g., in Western blotting, immunoprecipitation, gel-supershift, in situ imaging, etc. Immunoassay techniques using antibodies include radioimmunoassay, ELISA (enzyme-linked immunosorbant assay), "sandwich" immunoassays, immunoradiometric assays, gel diffusion precipitation reactions, immunodiffusion assays, in situ immunoassays (using, e.g., colloidal gold, enzyme or radioisotope labels), precipitation reactions, agglutination assays (e.g., gel agglutination assays, hemagglutination assays), complement fixation assays, immunofluorescence assays, protein A assays, and immunoelectrophoresis assays, etc. Antibodies can also be used in microarrays (see, e.g., International PCT Publication No. WO 00/04389). Furthermore, antibodies can be used as therapeutics to inhibit the activity of the proteins of the invention.

The present invention is further described by way of the following particular examples. However, the use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

EXAMPLE 1

Regulation of p53 Translation and Induction of p53 after DNA Damage by Ribosomal Protein L26 and Nucleolin Methods Plasmids. PCR-amplified RPL26 cDNA was subcloned into an EGFP expression vector, pEGFP-C3 (Clontech; BD Biosciences, Franklin Lakes, N.J.), and into a His tag-carrying vector, pET-15b (Novagen; EMD Biosciences, San Diego, Calif.) to obtain the RPL26-expressing plasmids pEGFP-C3-RPL26 and pET-15b-His-RPL26. PCR-amplified GFP and RPL26 cDNA were subcloned into pMSCV puro vector (Clontech), a murine stem cell virus vector carrying the puromycin-resistance gene. This cDNA was also subcloned by PCR amplification using a FLAG-tagged forward primer, into pIRES2-EGFP (Clontech) to generate FLAG tagged RPL26 driven by a CMV promoter.

RPL26 fragments d1-d7 were generated by PCR using pEGFP-RPL26 as a template and were subcloned into XhoI/EcoRI site (except for d4 which was produced by self-ligation of the PCR product) of EGFP expression vector pEGFP-C3 (Clontech).

| Fragm. | AA Boundaries | Sequence | PCR Primers |
|---|---|---|---|
| d1 | 2-89 | KFNPFVTSDRSKNRKR HFNAPSHIRRKIMSSP LSKELRQKYNVRSMPI RKDDEVQVVRGHYKGQ QIGKVVQVYRKKYVIY IERVQREK (SEQ ID NO: 17) | TCAGATCTCGAGAAG TTTAATCCCTTTGTG AC (SEQ ID NO: 28) AGCAGAATTCTTACT TTTCCCGCTGCACCC GTTCAA (SEQ ID NO: 29) |
| d2 | 2-62 | KFNPFVTSDRSKNRKR HFNAPSHIRRKIMSSP LSKELRQKYNVRSMPI RKDDEVQVVRGHY (SEQ ID NO: 18) | TCAGATCTCGAGAAG TTTAATCCCTTTGTG AC (SEQ ID NO: 30) AGCAGAATTCTTAAT AGTGTCCACGTACAA C (SEQ ID NO: 31) |
| d3 | 2-45 | KFNPFVTSDRSKNRKR HFNAPSHIRRKIMSSP LSKELRQKYNVR (SEQ ID NO: 19) | TCAGATCTCGAGAAG TTTAATCCCTTTGTG AC (SEQ ID NO: 32) AGCAGAATTGTTAtc gcACGTTGTACTTCT GTCTCAG (SEQ ID NO: 33) |
| d4 | 46-145 | SMPIRKDDEVQVVRGH YKGQQIGKVVQVYRKK YVIYIERVQREKANGT TVHVGIHPSKVVITRL KLDKDRKKILERKAKS RQVGKEKGKYKEETIE KMQE (SEQ ID NO: 20) | GTGCGATCCATGCCC ATCCCGAAAG (SEQ ID NO: 34) TCCCGCTTCGTCGAG ATCTGAGTAC (SEQ ID NO: 35) |
| d5 | 63-145 | KGQQIGKVVQVYRKKY VIYIERVQREKANGTT VHVGIHPSKVVITRLK LDKRKKILERKAKSRQ VGKEKGKYKEETIEKM QE SEQ ID NO: 21) | TCAGATCTCGAGAAA GGTCAGCAAATTGGC (SEQ ID NO: 36) AGCAGAATTCTTATT CCTGCATCTTCTC (SEQ ID NO: 37) |
| d6 | 90-145 | ANGTTVHVGIHPSKVV ITRLKLDKDRKKILER KAKSRQVGKEKGKYKE ETIEKMQE (SEQ ID NO: 22) | TCAGATCTCGAGGCT AATGGCACAACTGTC (SEQ ID NO: 38) AGCAGAATTCTTATT CCTGCATCTTCTC (SEQ ID NO: 39) |
| d7 | 45-116 | RSMPIRKDDEVQVVRG HYKGQQIGKVVQVYRK KYVIYIERVQREKANG TTVHVGIHPSKVVITR LKLDKDRK (SEQ ID NO: 23) | TCAGATCTCGAGCGA TCCATGCCCATCCGA AAG (SEQ ID NO: 40) AGCAGAATTCTTATT TGCGGTCTTTGTCCA G (SEQ ID NO: 41) |

A vector expressing the 5'UTR of p53 mRNA (pIIIA/MS2-2-p53 5'UTR) or 3'UTR of p53 mRNA (pIIIA/MS2-2-p53 3'UTR) was generated by subcloning PCR-amplified product of p53 5'UTR nucleotides −191 to 2 (the first adenine of the p53 coding sequence is defined as 1) having the sequence GGTTTTCCCCTCCCATGTGCTCAA-GACTGGCGCTAAAAGTTTTGAGCTTCTCAAAAG TCTAGAGCCACCGTCCAGGGAGCAGG-TAGCTGCTGGGCTCCGGGGACACTTTGCGT TCGGGCTGGGAGCGTGCTTTCCACGACG-GTGACACGCTTCCCTGGATTGGCAGCCA GACTGC-CTTCCGGGTCACTGCCAT (SEQ ID NO: 13) or 3'UTR nucleotides 2338 to 2486 having the sequence TTCATGC-CACCATGGCCAGCCAACTTTTGCAT-GTTTTGTAGAGATGGGGTCTCACAG TGTTGCCCAG-GCTGGTCTCAAACTCCTGGGCTCAGGCGATCCACC TGTCTCAGCCTC CCAGAGTGCTGGGATTACAAT-TGTGAGCCACCAC (SEQ ID NO: 14) into pIIIA/MS2-2 vector (Bernstein et al., Methods 2002; 26:123-141). pAS2-1 and pACT2 plasmids were obtained from Clontech. pcDNA3 was obtained from Invitrogen (Carlsbad, Calif.). A vector expressing human papilloma virus protein E6 (pCMV-E6) was described previously (Kessis et al., Proc. Natl. Acad. Sci. USA, 1993, 90(9):3988-92). A plasmid containing the dominant negative (DN) allele (L22Q, W23S, and D281G) of p53 (pCMV-p53-DN) was obtained from Dr. Gerard Zambetti (Lin et al., Genes Dev. 1994; 8:1235-46). The PG13-luciferase reporter plasmid, a luciferase reporter containing 13 copies of a p53 binding site, was obtained from Dr. Bert Vogelstein, (The Sidney Kimmel Comprehensive Cancer Center at the Johns Hopkins University Medical Institute, Baltimore, Md.)(Kern et al., Science 1992; 256:827-830; El-Deiry et al., Cell 1993; 75:817-825). The p21 luciferase reporter plasmids were obtained from Dr. Masayuki Nagasawa (Tokyo Medical and Dental University). pCMV3-nucleolin was obtained from Dr. France Carrier (University of Maryland).

pEGFP-C3-nucleolin was constructed by subcloning nucleolin cDNA from pCMV3-nucleolin into pEGFP-C3 vector. pQCGFPIP and pQCGFP-nucleolinIP was obtained by subcloning EGFP cDNA or EGFP-nucleolin cDNA into pQCXIP vector (Clontech). pBABE puro and pBABE puro Ha-Ras G12V were obtained from Dr. Scott Lowe and Martine Roussel (Cold Spring Harbor Laboratory and St. Jude Children's Research Hospital; Serrano, et al., Cell 1997, 88:593-602). pMSCV puro p53 R175H was obtained from Dr. Hiroshi Nakagawa (University of Pennsylvania; Takaoka, et al., Oncogene 2004; 23:6760-8). pSuper.Retro.GFP.neo (OligoEngine) was used for shRNA expression.

Cells, transfection of plasmid, production and infection of retrovirus. Human epithelial cell lines MCF7 (ATCC Accession No. HTB-22, ATCC, Manassas, Va.), U2OS (ATCC Accession No. HTB-96; ATCC, Manassas, Va.), RKO (ATCC Accession No. CRL-2577; ATCC, Manassas, Va.), and SW480 (ATCC Accession No. CCL-228; ATCC, Manassas, Va.), carrying the wild-type p53 (MCF7, U2OS, and RKO) or mutated p53 (SW480) or in which the p53 gene was deleted (H1299) were maintained in Dulbecco's modified Eagle medium (DMEM; Gibco Invitrogen, Carlsbad, Calif.) containing 10% fetal calf serum (FCS; Gibco Invitrogen). The human epithelial cell line HCT 116 (ATCC Accession No. CCL-247; ATCC, Manassas, Va.) and p53−/− HCT 116 cells (obtained from Dr. Bert Vogelstein, The Sidney Kimmel Comprehensive Cancer Center at the Johns Hopkins University Medical Institute, Baltimore, Md.; Bunz, et al., Science 1998; 282:1497-1501) were maintained in McCoy's 5A medium (Gibco Invitrogen) containing 10% FCS. The murine immature hematopoietic cell line BaF3 (Palacios and Steinmetz, 1985) was maintained in RPMI medium (Gibco Invitrogen) containing 10% FCS and 10% culture supernatant from WEHI-3B cells (DSMZ Accession No. ACC 26 [the German Collection of Microorganisms and Cell Cultures], Braunschweig, Germany). ARF−/− and ARF−/−p53−/− mouse embryo fibroblasts (MEF) and rat embryo fibroblast (obtained from Dr. Charles Sherr, and Dr. Gerard Zambetti, St. Jude Children's Research Hospital; Kamijo, et al., Cancer Res. 1999, 59:2464-9) were maintained in DMEM containing 10% FCS, 2 mM L-glutamine, 0.1 mM MEM nonessential amino acids, and 55 µM β-mercaptoethanol (Gibco Invitrogen). Transient transfection was achieved by using the transfection reagent Effectene™ (Qiagen, Valencia, Calif.) or Lipofectamine 2000 (Invitrogen). BaF3 cells were electroporated by using the T20 program of the Nucleofector™ device and the cell line Nucleofector Kit V (Amaxa Biosystems, Gaithersburg, Mass.). EGFP-mock and EGFP-nucleolin stably overexpressed MCF7 cells were obtained by G418 (Invitrogen) selection at 2 mg/ml concentration after transfection. Retrovirus production and infection was performed as previously reported using 293T cells (Sugimoto et al., Mol. Cell. 2003; 11:415-424).

RNA ligase mediated oligo-capping rapid amplification of 5' cDNA end (RLM-5'RACE). RLM-5'RACE was performed using Gene Racer™ kit (Invitrogen, Carlsbad, Calif.) according to the manufacturer's protocol. Amplified PCR product was TA cloned into pCR II TOPO vector (Invitrogen) using TOPO TA cloning kit (Invitrogen) and 100 independent clones were sequenced.

Yeast three-hybrid screen. The yeast three-hybrid system described in Bernstein et al., Methods 2002; 26:123-141 and SenGupta et al., Proc. Natl. Acad. Sci. U.S.A 1996; 93:8496-8501 was performed to identify proteins which interact with 5'UTR of p53 mRNA. pIIIA/MS2-2-p53 5'UTR was used as a bait plasmid. For the screen, a cDNA library from human HeLa cells fused to GAL4 activation domain (obtained from Dr. Shuki Mizuatni, Tokyo Medical and Dental University) was used to cotransform the L40 coat yeast strain [MATa, ura3-52, leu2-3,112, his3-200, trp101, ade2.LYS2::lexA op-His3, LexA-MS2 coat (TRP1)] (obtained from Dr. Marvin Wickens, University of Wisconsin; Bernstein, et al., Methods 2002, 26:123-141) with pIIIA/MS2-2-p53 5'UTR. Transformants were allowed to grow at 30° C. on histidine-lacking plates supplemented with 15 mM 3-amino-1,2,4-triazole (3AT; Sigma-Aldrich, St. Louis, Mo.). To select cells that have lost the pIIIA/MS2-2-p53 5'UTR plasmid, cells were plated on medium containing 5-fluoroorotic acid (5-FOA) (Sigma-Aldrich, St. Louis, Mo.), which causes rejection of clones that have incorporated this URA3-containing bait plasmid. Then pACT2 plasmid containing candidate cDNAs were recovered from yeast grown on replicate plates, using the 5-FOA-sensitive clones as indicator. Only clones that exhibited RNA-dependent and RNA-specific growth were further characterized. To confirm that these clones expressed proteins that bind specifically to the 5'UTR of p53 mRNA, a 3-AT-resistance assay was performed using the 5'UTR and 3'UTR (nucleotides 2338 to 2486) of p53 mRNA as a control bait.

Antibodies and immunoblotting. Polyclonal rabbit anti-RPL26 antibodies were obtained by immunizing rabbits with KLH-conjugated RPL26 peptides SKNRKRHFNAPSHIR-RKI (corresponding to RPL26 N-terminal amino acids 12-29; SEQ ID NO: 26) and RQVGKEKGKYKEETIEK (corresponding to RPL26 C-terminal amino acids 126-142; SEQ ID NO: 27). Antibodies were purified by affinity chromatography on an N-hydroxysuccinimide (NHS)-activated Sepharose™ 4 Fast Flow column (Amersham Biosciences). For Western blotting, N-terminal antibody was employed; for immunofluorescence (IF), C-terminal antibody was employed; and for immunoprecipitation (IP), both antibodies were employed.

Cell lysates were prepared by washing the cells with phosphate-buffered saline (PBS) then incubating in RIPA buffer for 30 min on ice and cell lysates were subjected to Western blot analysis after removing the insoluble fraction by centrifugation at 13,000 g for 20 min. When indicated, nuclei were obtained after centrifugation of cell lysate using hypotonic buffer (10 mM HEPES, pH7.5, 10 mM KCl, 1.5 mM MgCl2) from MCF7 cells. Nucleoli were prepared from nuclei using a method as previously described (Busch et al., Cancer Res. 1965; 25:225-233). Cell lysates were prepared by washing the cells with phosphate-buffered saline (PBS) then incubating in RIPA buffer (150 mM NaCl, 1.0% NP40, 0.1% sodium dodecyl sulfate [SDS], 0.1% sodium deoxycholate, 5 mM EDTA, 10 mM Tris-HCl, pH 7.4, containing protease inhibitors [complete mini cocktail; Roche Diagnostics, Indianapolis, Ind.] and 0.5 mM PMSF) for 30 min on ice. Cell lysates were subjected to Western blot analysis after removing the insoluble fraction by centrifugation at 13,000 g for 20 min. Protein concentration was measured by using the DC protein assay (Bio-Rad, Richmond, Calif.); 30 µg protein samples were denatured in boiling SDS sample buffer, separated by SDS polyacrylamide gel electrophoresis, and transferred to nitrocellulose membrane (Schleicher & Schuell, Keene, N.H.). After blocking nonspecific binding of antibody with 5% nonfat milk, blots were probed with primary antibody against p53 (Ab-6 clone DO-1; EMD Biosciences, La Jolla, Calif.), HDM2 (SMP14; Santa Cruz Biotechnology, Santa Cruz, Calif.), phospho-p53 (Ser15) (Cell Signaling Technology, Beverly, Mass.), p21 (C-19; Santa Cruz Biotechnology), actin (1-19; Santa Cruz Biotechnology), ATM (MAT3; obtained from Dr. Yosef Shiloh, Tel Aviv University, Israel; Bakkenist et al., Nature 2003; 421:499-506), phospho-ATM (Ser$^{1981}$) (Bakkenist et al., Nature 2003; 421:499-506), nucleolin (MS-3; Santa Cruz Biotechnology), nucleophosmin/B23 (C-19; Santa Cruz Biotechnology), heterogeneous nuclear ribonucleoprotein U (hnRNPU) (C-15; Santa Cruz Biotechnology), green fluorescent protein (GFP) (FL; Santa-Cruz Biotechnology), penta-His (Qiagen), or luciferase (Promega, Madison, Wis.). Primary antibodies were detected by binding horseradish peroxidase (HRP)-conjugated anti-rabbit, anti-mouse, or anti-goat second antibody (Pierce Biotechnology, Rockford, Ill.) and using an enhanced chemiluminescent visualization (ECL) system (Amersham Biosciences, Buckinghamshire, UK).

Metabolic labeling of cells and measurement of rate of p53 synthesis by immunoprecipitation. Before labeling, MCF7 cells were preincubated in DMEM without methionine and cysteine with 5% dialyzed FCS for 1 h. When indicated, preincubated cells were treated with proteosome inhibitor, 50 µM MG132 (EMD Biosciences) for 1 h, irradiated with 5 Gy, and 30 min after irradiation labeled with 100 µCi/ml of [$^{35}$S] methionine (Amersham) for 5 min. Cells were washed with PBS and lysed in RIPA buffer. The insoluble fraction was removed from the cell lysate by centrifugation at 13,000 g for 20 min, and lysates were further cleared by incubation with protein A/G-PLUS agarose(Santa Cruz Biotechnology) and rabbit IgG (Sigma-Aldrich). Precleared lysates were incubated with anti-p53 antibody (FL-393; Santa Cruz Biotechnology) for 1 h. The p53-antibody complex was recovered by binding to protein A/G-PLUS agarose, and the beads were washed extensively with RIPA lysis buffer. Immunoprecipitated p53 was boiled in SDS sample buffer and resolved by gel electrophoresis, then transferred to nitrocellulose membrane. The amount of labeled p53 on the membrane was estimated by exposure to X-ray film, and the total amount of immunoprecipitated p53 on the membrane was detected by Western analysis with anti-p53 antibody (Ab-6).

In vitro transcription of p53 mRNA and mRNA transfection. In vitro transcription of capped p53 mRNA was performed using the mMESSAGE mMACHINE kit (Ambion, Austin, Tex.) and poly A sequence added by using the poly(A) tailing kit (Ambion) using a T7 promoter sequenced tagged p53 PCR product as template. Synthesized mRNA was transfected into H1299 cells by using DMRIE-C transfection reagent (Invitrogen). In vitro transcription and translation was achieved by using the TNT quick coupled transcription/translation system (Promega) according to the manufacturer's protocol.

RNA electrophoretic mobility gel shift assay (RNA-EMSA). p53 5'UTR RNA (–191 to 2) was generated by in vitro transcription with T7 polymerase (Ambion) and 5' labeled with [$^{32}$P]γ-ATP (Amersham) by using T4 polynucleotide kinase (Promega). Radiolabeled RNA (150,000 c.p.m.) was incubated with His-tagged RPL26 or a His-tagged control protein that was in vitro transcribed and translated in rabbit reticulocyte lysate (Promega) in binding buffer (10 mM HEPES/KOH pH 7.5, 90 mM potassium acetate, 1.5 mM magnesium acetate, 2.5 mM DTT, and 40 U ribonuclease inhibitor [SUPERase•In; Ambion]) for 30 min at 30° C. RNA-protein complexes were resolved on a 4.5% acrylamide (60:1 acrylamide to bisacrylamide), 5% glycerol, and 0.5× Tris-borate-EDTA (TBE) gel and detected by autoradiography.

Immunoprecipitation and reverse transcription (IP-RT-PCR). IP-RT-PCR was performed as previously described (Tenenbaum et al., 2002). Briefly, MCF7 cells were lysed in polysome lysis buffer (100 mM KCl, 5 mM MgCl2, 10 mM HEPES, pH 7.0, 0.5% NP40, 1 mM DTT, 100 U/ml SUPERase•In, protease inhibitor cocktail, 0.5 mM PMSF). After preclearing lysates with mouse IgG (Sigma-Aldrich) and protein A/G-PLUS agarose, primary antibody and protein A/G PLUS agarose was incubated with 100 µl precleared cell lysate, 900 µl NT2 buffer (50 mM Tris-HCl, pH 7.4, 150 mM, NaCl, 1 mM MgCl2, 0.05% NP40), 100 U/ml SUPERase•In, 1 mM DTT, and 15 mM EDTA for 1 h at 4° C. RNA was extracted using Trizol™ (Invitrogen) after extensive washing with NT2 buffer, reverse transcribed by using Superscript™ II (Invitrogen) with random primer and amplified by PCR.

Luciferase reporter gene assay. MCF7 cells were transiently transfected with the pG13 and p21 firefly luciferase reporter vector with pRL-SV40 *Renilla* luciferase internal control vector. Firefly and *Renilla* luciferase activities were measured by using the Dual-Luciferase™ reporter assay system (Promega) and a MicroLumat Plus 96V luminometer (Berthold Technologies, Bad Wildbad, Germany).

Analysis of mRNA distribution in polysomes. mRNA distribution in polysomes was analyzed by a method modified from that described by Whitfield et al. (Whitfield et al, Mol. Cell. Biol. 2000; 20:4188-4198). Just before harvesting, the cells were treated with cycloheximide (0.1 mM) to fix the mRNA on the polysomes, then washed in PBS and lysed by gentle shaking in 0.5% NP40, 0.1 M NaCl, 10 mM MgCl2, 2 mM DTT, 50 nm Tris-HCl (pH 7.5) containing 200 U/ml SUPERase•In, 100 µg/ml cycloheximide, 200 µg/ml heparin, protease inhibitor cocktail (Roche Diagnostics), and 0.1 mM PMSF. Nuclei and membranes were removed from each lysate by centrifugation at 10,000 g for 15 min, and each supernatant was layered on a 15% to 40% (wt/vol) sucrose gradient (9 ml) in 0.15 M NaCl, 5 mM MgCl2, 25 mM Tris-HCl (pH 7.5) and centrifuged for 140 min at 35,000 r.p.m. in an SW41 rotor (Beckman Coulter, Fullerton, Calif.). Fractions were collected using a model 2110 fraction collector (Bio-Rad), and RNA from each fraction was extracted using phenol/chloroform followed by ethanol precipitation. RNA from each fraction was treated with formamide, resolved by agarose gel electrophoresis, transferred to nitrocellulose membrane, and analyzed for p53 and actin mRNA by Northern blotting.

siRNA. siRNA specific for human RPL26 (CCGAAAG-GAUGAUGAAGUUUU (SEQ ID NO: 8)) and mixtures of functional siRNA specific for human and mouse RPL26 made by SMART pool technology were obtained from Dharmacon (Lafayette, Colo.). A control siRNA was obtained from Ambion. Cells were transfected with a final concentration of 20 nM siRNA by using siPORT transfection agent (Ambion) according to the manufacturer's instructions. Sequence of shRNA specific for nucleolin and control was AGAGC-GAGATGCGAGAACA (SEQ ID NO: 9) and AATCA-GACGTGGACCAGAAGA (SEQ ID NO: 15), respectively.

RNA pull-down assay followed by protein identification. Cytoplasmic extracts were prepared from 1×1010 MCF7 cells by using hypotonic buffer (10 mM HEPES, pH7.5, 10 mM potassium acetate, 1.5 mM magnesium acetate, 2.5 mM DTT, 0.05% NP40, protease inhibitor cocktail, 0.5 mM PMSF) and a Dounce homogenizer. Cytoplasmic extract was precleared by centrifugation and the potassium acetate concentration adjusted to 90 mM. After addition of SUPERase•In (0.025 U/ml) and yeast tRNA (15 µg/ml) (Ambion), cytoplasmic extracts were applied to an equilibrated heparin-agarose column (Bio-Rad). Eluates were further cleared with 100 µl streptavidin Sepharose™ (Sigma-Aldrich) for 1 h at 4° C. with rotation. After centrifugation, 10 µg of in-vitro transcribed biotinylated RNA was added to the supernatant and the mixture incubated for 1 h at 4° C. The protein and biotinylated RNA complexes were recovered by addition of 30 µl streptavidin Sepharose™ (2 h incubation at 4° C. with rotation), and the protein, biotinylated RNA, and streptavidin Sepharose™ complexes were washed 5 times with binding buffer (10 mM HEPES, pH 7.5, 90 mM potassium acetate, 1.5 mM magnesium acetate, 2.5 mM DTT, 0.05% NP40, protease inhibitor cocktail, 0.5 mM PMSF) then boiled in SDS sample buffer, resolved by gel electrophoresis.

For western blotting, 5×10$^9$ MCF7 cells were subjected for assay, and the precipitant were transferred to nitrocellulose membrane after gel electrophoresis. The protein in a gel piece, was reduced and alkylated with iodoacetamide, and tryptic digest was prepared. Tryptic peptide were extracted and subjected to combined capillary liquid chromatography/tandem mass spectrometry. Mass spectrometry was performed using a Finnigan LCQ Deca mass spectrometer (Thermo Electron Corporation, San Jose, Calif.) with nano electrospray ion source. Fragment ion (MS2) spectra were subjected to database search using the SEQUEST™ program of Eng and Yates marked by ThermoQuest. NCBInr database, rev. May 13, 2003, human subset was used (available on the WorldWideWeb at ncbi.nlm.nih.gov/).

REF colony formation assay. REFs (passage 3) were infected with mock (pBABE puro empty vector) or oncogenic mutant Ras (pBABE puro H-Ras G12V), followed by GFP-mock (pQCGFPIP) or GFP-nucleolin (pQCGFP-nucleolinIP), or mutant p53 (pMSCV puro p53 R175H). 24 hr after infection, cell were trypsinized and 5000 cells were resuspended 1 ml 1× Iscove's modified Dulbecco's medium (IMDM) 0.3% agar and plated on 2-ml 1×IMDM 0.6% bottom agar on 6 well plate. The agar plates were incubated 37° C. in an atmosphere of 5% CO2 for soft agar colony formation assay. 50% confluent retrovirus infected REFs were further cultured for morphorogical assessment after infection.

Cell cycle and apoptosis analysis. Cell cycle distribution was analyzed bromodeoxyuridine (BrdU) pulse labeled method using APC BrdU flow kit (BD Biosciences, San Jose, Calif.). GFP-positive cells were gated, and BrdU-positive cells in the GFP-positive population were identified by the presence of APC fluorescence. For apoptosis cell determination, cells were stained with APC-conjugated annexin V and 7-amino-actinomycin (7-AAD) (BD Biosciences) according to the manufacturer's protocol, 3 h after irradiation. GFP-positive cells were gated, and apoptotic cells in the GFP-positive population were identified by the presence of APC fluorescence.

Clonogenic assay. ARF−/− MEF and ARF−/−p53−/− MEF were retrovirally infected with MSCV-GFP-mock vector or MSCV-GFP-RPL26 vector. GFP-positive cells were sorted 24 h after infection and plated at a density of 10,000 cells per 10 cm plate. Cells were stained with crystal violet (Sigma-Aldrich) 1 week after infection.

Results

Effects of DNA Damage and the 5'UTR on p53 Translation

As previously demonstrated in ML-1 cells (Kastan et al., Cancer Res 1991; 51:6304-6311), brief exposure of MCF7 cells to the protein synthesis inhibitor, cycloheximide, reduces induction of p53 protein after ionizing radiation (IR). p53 and actin protein levels in MCF7 cells treated with and without 10 mM cycloheximide (CHX) 10 min before 5 Gy irradiation (IR) were assessed by immunoblot. Cells were unirradiated (−) or harvested 10 or 20 min after IR. The amount of newly synthesized p53 protein was evaluated by brief labeling pulses with [$^{35}$S]methionine at very early time points after IR under conditions where additional effects of protein turnover were avoided by treating the cells with a proteasome inhibitor. Though total levels of p53 protein were indistinguishable in unirradiated versus irradiated cells, the amount of newly synthesized p53 was significantly greater in the irradiated cells, thus demonstrating increased translation. p53 protein was immunoprecipitated from MCF7 cells that had been labeled for 5 minutes with [$^{35}$S]methionine 30 minutes after exposure to 0 or 10 Gy IR and was assessed by autoradiography. Cells pre-treated with 50 µM MG132 and immunoblotting (WB) showed equivalent amounts of p53 in the immunoprecipitate. Analysis of whole cell extracts (WCE) showed equal amounts of [$^{35}$S]methionine incorporated into the irradiated and unirradiated cells. Similar results were obtained even in the absence of the proteasome inhibitor or when [$^{35}$S]-labeled p53 was measured after IR in tumor cells with mutant p53, which do not increase p53 levels after IR.

Figure 2B:
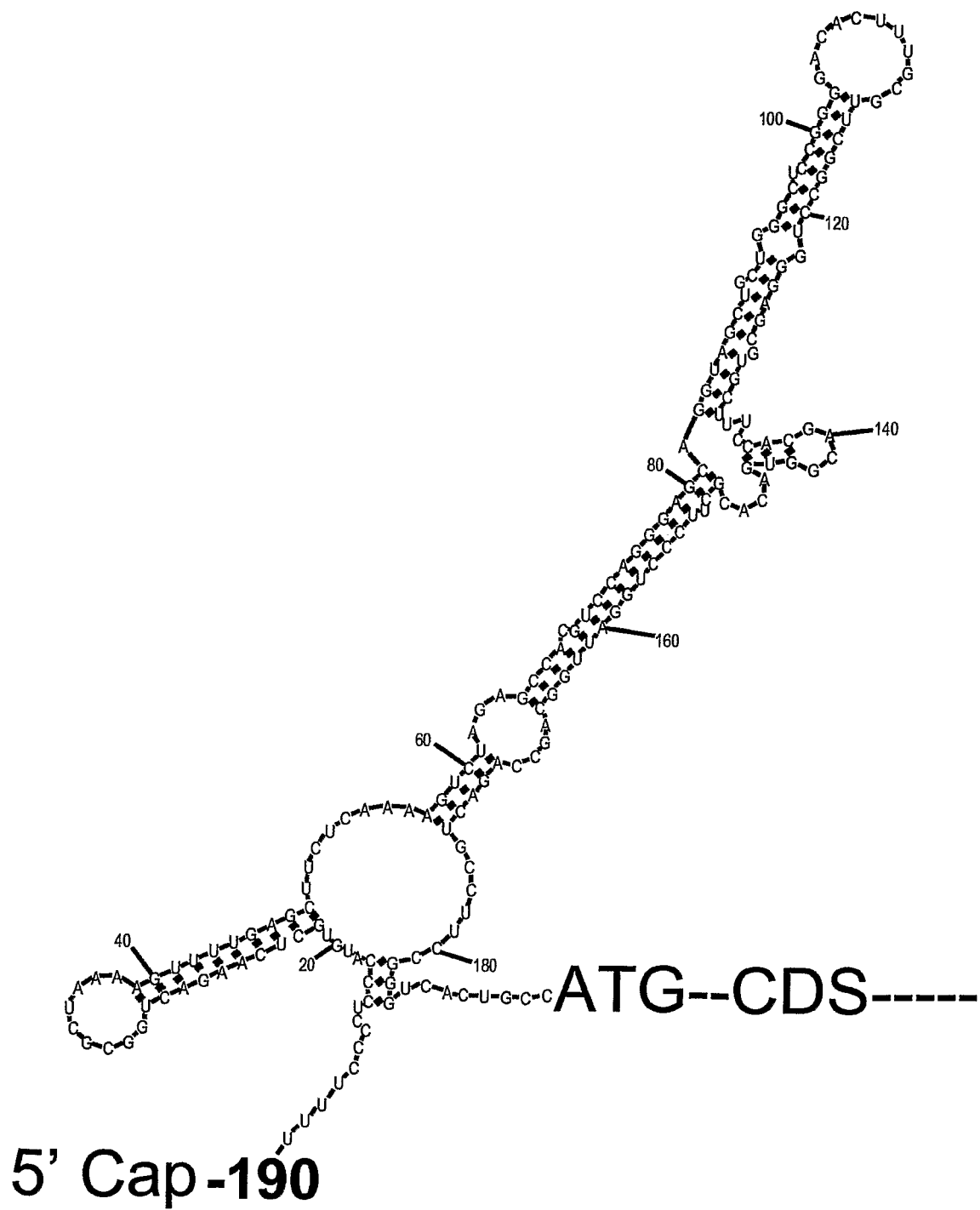

To begin to explore whether the 5'UTR of p53 mRNA affects its translation in cells, the amount of human p53 protein generated by mRNA containing various lengths of the 5'UTR was examined. The National Center of Biotechnology Information (NCBI) data base (available on the World-WideWeb at ncbi.nlm.nih.gov/) lists several human p53 mRNA molecules that contain various lengths of the 5'UTR, the longest being 251 nucleotides (SEQ ID NO: 12; see GenBank Accession No. NM_000546). A previous study suggested that the majority of cellular p53 mRNA has a 5'UTR of 140-145 nucleotide with a minor population containing 176 nucleotides (Tuck et al, Mol. Cell. Biol. 1989; 9:2163-2172). RNA ligase-mediated rapid amplification of 5'cDNA ends (RLM-5'RACE) was employed to evaluate the predominant p53 mRNA species in several human cell lines. The major species contained a 5'UTR of 139-143 nucleotides (62%) and a minor population contained 161-190 nucleotides (FIG. 2A). Similar to the prediction for the mouse p53 mRNA 5'UTR, the mfold program (Zuker, et al., Nucleic Acids Research 2003; 31:3406-3415) predicted that this human 5'UTR contains a highly ordered secondary structure that could suppress translation (free energy of folding ΔG=−66 kcal/mol; FIG. 2B). To evaluate a potential impact of the 5'UTR on p53 protein expression, several p53 mRNAs were generated with various lengths of the 5'UTR attached to the full-length coding sequence with a full-length 3'UTR and poly (A) sequence. Transfection of these RNA species into p53-null H1299 cells demonstrated that the length of the 5'UTR had a significant impact on the amount of p53 protein that was generated. H1299 cells were transfected with deletion mutants of p53 mRNA having 5'UTRs of various lengths (1, 22, 75, 146, 192, and 251 nucleotides), a full-length coding sequence, a complete 3'UTR and poly A. The construct contained a firefly luciferase mRNA as an internal control. Immunoblotting was used to compare the amounts of p53 and firefly luciferase present 24 h after transfection. Maximal p53 expression occurred when the 5'UTR contained 75 nucleotides while p53 was much less efficiently translated when the mRNA had a relatively long (192 nucleotides or 251 nucleotides) or very short 5'UTR (1 nucleotide).

Identification of RPL26 and Nucleolin as p53 5'UTR Binding Proteins

Since the 5'UTR of p53 mRNA appeared to affect p53 protein levels and given that UTR-binding proteins are involved in the translational regulation of gene expression (Gray et al., Annu. Rev. Cell Dev. Biol. 1998; 14:399-458; Mignone et al., Genome Biol. 2002; 3:REVIEWS0004; Stripecke et al., Mol. Cell. Biol. 1994; 14:5898-5909; Troffa et al., Cancer Cell 2003; 3:145-160), two screens were designed to search for proteins that bind to the 5'UTR of p53 mRNA. A yeast-three hybrid screen (Bernstein et al., Methods 2002; 26:123-141; SenGupta et al., Proc. Natl. Acad. Sci. U.S.A 1996; 93:8496-8501) identified several clones that bind non-specifically to the 5'UTR of p53 mRNA and four clones that appeared to exhibit some specificity relative to binding to the 3'UTR of p53 mRNA. 5×10$^5$ clones were screened to yield 128 primary HIS3-positive clones, 97 of which were also positive for LacZ, 33 of which were selected by 5-FOA sensitivity. Of these 33 clones, 10 contained open reading frames. Binding of proteins expressed by each pACT2 clone to p53 5'UTR was assessed by activating HIS3 in the presence of 15 mM 3-AT. The 3'UTR was used as control bait. Additional information on the binding proteins is described in Table 1.

TABLE 1

| clone | Gene | Accession No. | p53 5'UTR binding | p53 3'UTR binding |
|---|---|---|---|---|
| 1 | CCT5 | NM_012073 | + | + |
| 2 | DKFZP564M182 | NM_015659 | + | + |

TABLE 1-continued

| clone | Gene | Accession No. | p53 5'UTR binding | p53 3'UTR binding |
|---|---|---|---|---|
| 3 | MGC14595 | NM_032334 | + | + |
| 4 | Nucleostemin | NM_014366 | + | − |
| 5 | Ribosomal protein L41 | NM_021104 | + | + |
| 6 | Ribosomal protein L26 | NM_000987 | + | − |
| 7 | Ribosomal protein L5 | NM_000969 | + | + |
| 8 | Ribosomal protein S13 | NM_001017 | + | − |
| 9 | Ribosomal protein S7 | NM_001011 | + | + |
| 10 | Ribosomal protein S3a | NM_001006 | + | − |

The four clones that showed some specificity for binding (Ribosomal protein (RP) S3a, RPS13, RPL26, and nucleostemin) as well as the non-specific clone RPL5, which had previously been reported to stabilize p53 protein (Dai et al., J. Biol. Chem. 2004; 279:44475-44482), were subcloned into Enhanced green fluorescence protein (EGFP)-tagged mammalian expression vectors and tested for their ability to modulate p53 expression levels. Candidates RPS3a, RPS13, RPL26, and nucleostemin (NS) and nonspecific clone RPL5 were transfected into MCF7 cells, and their effects on p53 and actin expression were compared by immunoblotting 24 hours after transfection. A mock transfectant was used as a control. While RPL5 weakly increased p53 expression, only RPL26 overexpression significantly increased p53 protein levels. Thus, subsequent experiments focused on exploring the importance of RPL26 in controlling p53 protein expression.

To verify the binding of RPL26 to the 5'UTR of p53 mRNA, in vitro and cell binding assays were utilized. $^{32}$P-labeled 5'UTR was incubated with His-control protein (−, −) or His-RPL26 (−, +); super-shift was assessed by addition of anti-penta His antibody (+, +). Incubation of recombinant His-tagged RPL26 protein with the $^{32}$P-labeled p53 5'UTR significantly slowed the electrophoretic mobility of the RNA, and the complex was super-shifted by addition of anti-penta His antibody. An RNA pull-down assay was employed using lysates from unirradiated or irradiated MCF7 cells, and the binding of selected proteins to biotinylated p53 5'UTR versus p53 3'UTR was evaluated. Whole cell extracts (WCE) were prepared from MCF7 cells 1 hour after 0 (−) or 10 (+) Gy (IR) and mixed with biotinylated 5'UTR or 3'UTR from p53 mRNA. Input WCE and 5'UTR- and 3'UTR-bound fractions were analyzed by immunoblotting with antibodies to hnRNPU, nucleolin, p53, and RPL26. RPL26 was preferentially precipitated by the 5'UTR after irradiation, but no RPL26 was detected when the 3'UTR was used as bait. The ability of RPL26 to bind to p53 mRNA in living cells was evaluated by immunoprecipitating transfected FLAG-RPL26 from MCF7 cell lysates and examining the immunoprecipitate for the presence of p53 mRNA by RT-PCR using a p53 5'UTR primer. MCF7 cells were transiently transfected with FLAG-mock or FLAG-RPL26 expression vector. One hour following 10 Gy IR, anti-FLAG was used for immunoprecipitation and bound RNA was amplified by PCR of the 5'UTR of p53. PCR products were visualized by ethidium bromide staining. SM: size marker, input: 20% of the RT-PCR product obtained by using RNA from the whole cell extract. The p53 mRNA was detected in the FLAG-RPL26 immunoprecipitate and more p53 mRNA was precipitated in the lysates from irradiated cells.

An RNA pull-down assay was also utilized as a screen for proteins that specifically bind to the 5'UTR of p53 mRNA. Cytoplasmic extracts from MCF7 cells 1 hour after 0 or 10 Gy IR were incubated with biotinylated 3' or 5'UTR of p53 and precipitated with streptavidin beads. Gel was stained by Cypro Ruby. Information of binding proteins is shown in Table 2. Using biotinylated p53 5'UTR and 3'UTR RNAs as bait and mass spectrometry to identify unknown binding proteins, several protein bands were identified as preferentially binding to the 5'UTR, including nucleolin.

TABLE 2

| protein | Accession (gi) |
|---|---|
| Gem-associated protein 5 (Gemin5) | 34921882 |
| HRX | 84394 |
| zinc-finger DNA-binding protein | 1405348 |
| ATP-dependent RNA helicase A (RHA/DDX9) | 3915658 |
| heterogeneous ribonuclear particle protein U (hnRNPU) | 284156 |
| nucleolin | 55956788 |
| transcription intermediary factor 1-beta | 3183181 |
| translation control protein 80 (TCP80) | 5006602 |
| ATP-dependent DNA helicase II, 80 kDa subunit (Ku80) | 125731 |
| ATP-dependent DNA helicase II, 70 kDa subunit (Ku70) | 125729 |
| heat shock cognate protein 54 (HSC54) | 11526573 |
| hepatocellular carcinoma autoantigen | 4883681 |
| synaptotagmin binding, cytoplasmic RNA interacting protein (NSAP) | 23397427 |
| IGF-II mRNA-binding protein 3 (IMP-3) | 4191612 |
| protein kinase, interferon-inducible double stranded RNA dependent (PKR) | 4506103 |
| staufen protein | 4335947 |
| GTP-binding like protein 2 | 9971158 |
| similar to TSH receptor suppressor element-binding protein-1 (TSEP-1) | 51105936 |
| Elongation factor-1-alpha (eEF1A-1) | 55584035 |
| ribonucleoprotein La | 337457 |
| Nuclease sensitive element binding protein 1 (YB-1) | 54040030 |
| tuberin | 3522922 |
| CSDA protein | 14602477 |
| transcription factor NF-AT | 1082855 |
| TAR RNA binding protein 2 isoform a (TRBP) | 19743840 |
| casein kinase 1, gamma 2 | 18088090 |
| ribosomal protein L26 (RPL26) | 4506621 |

Most of the proteins identified in this screen were known interactors with nucleolin as part of large ribonucleocomplexes (Yanagida et al., Proteomics. 2001; 1:1390-1404). The specific interaction of nucleolin with the 5'UTR of p53 mRNA was also observed in an RNA pull-down assay with a western blot readout. However, in contrast to RPL26, there was no detectable change in the binding of nucleolin after IR. As previously suggested (Mosner et al., EMBO Journal 1995; 14:4442-4449), p53 protein was also identified as a p53 5'UTR binding protein. The interaction between nucleolin and p53 mRNA in living cells was confirmed by identifying p53 mRNA in anti-nucleolin immunoprecipitates by RT-PCR using a p53 5'UTR primer. IP-RT-PCR for p53 5'UTR was performed using anti-nucleolin antibody or control mouse IgG. It is noted that these assays do not distinguish whether it is nucleolin or some other protein in the ribonucleocomplex that directly interacts with the p53 mRNA, but subsequent studies (see below) demonstrated that manipulation of nucleolin levels markedly affect p53 protein translation, thus suggesting functional importance for this particular member of the complex.

RPL26 Overexpression Increases p53 Levels, Function and Translation

To explore the functional role of RPL26 in controlling p53 protein levels, RPL26 was overexpressed in the human cell lines MCF7, U2OS, RKO, HCT116, and the mouse cell line BaF3. Levels of various proteins were assessed by immunoblot one hour after 0 or 5 Gy IR in MCF7 cells transfected with increasing amounts of GFP-RPL26. In all cases, transfected RPL26 significantly increased levels of p53 protein. Using MCF7 cells, a dose-dependent relationship between levels of transfected RPL26 and levels of endogenous p53 protein was demonstrated. RPL26 also enhanced the amount of p53 protein induced by IR. The increased p53 led to augmented expression of p53 target genes, including p21 and HDM2. Overexpression of RPL26 had no effect on the expression of several other proteins (actin, ATM, nucleolin, topoisomerase I, eIF4E, and hnRNPU). Kinetic analysis showed that expression of p21 and HDM2 were induced as expected by irradiation and augmented by RPL26 overexpression. Because optimal induction of p53 after IR requires activation of the ATM kinase, it was important to rule out an effect of RPL26 overexpression on ATM activation. Activation of the ATM kinase, as measured by autophosphorylation of Ser 1981 (Bakkenist et al., Nature 2003; 421:499-506), was not affected by RPL26 overexpression in either unirradiated or irradiated cells.

Further support for the concept that RPL26 overexpression was affecting p53 directly rather than through ATM was the observation that RPL26 overexpression did not induce phosphorylation of p53 at Ser 15 in unirradiated cells, despite the presence of abundant p53 protein. Levels of various proteins were assessed by immunoblot at various times after 0 (−) or 5 Gy IR in MCF7 cells transfected with a GFP-mock or a GFP-RPL26 vector. These results suggest that overexpression of RPL26 induces functional p53 accumulation without activation of the DNA damage checkpoint pathway. A luciferase reporter assay was employed to confirm that augmentation of p53 expression by RPL26 correlates with increased p53 transcriptional activity. This assay tested p53 transcriptional activity using a generic p53 consensus target sequence or a p21 promoter sequence in cells co-transfected with a GFP-mock or a GFP-RPL26 vector. Luciferase activity was evaluated three hours after exposure of cells to 0 (−) or 5 Gy IR and the reporter activity shown as firefly luciferase activity relative to Renilla luciferase activity. Overexpression of RPL26 increased the activity of reporters containing either a p53 consensus target sequence (PG13) or the p21CIP1 promoter and augmented the irradiation-induced activity of both promoters.

The increases in p53 protein levels associated with RPL26 overexpression could result from pre-translational, translational, or post-translational effects. To test this, MCF7 cells were transfected with GFP-mock or GFP-RPL26. RT-PCR products were semi-quantitatively evaluated 1 hour after 0 or 5 Gy IR. RPL26 transfection did not change the cellular levels of p53 mRNA, thus suggesting that any changes in p53 protein levels were post-transcriptional. Similarly, RPL26 transfection did not alter the half-life of p53 protein, thus ruling out increased protein half-life as an explanation for the increased p53 protein levels. MCF7 cells were pulse-labeled with [$^{35}$S] methionine for 10 min and p53 was immunoprecipitated at the indicated time points after chasing the label. The densitometric values of the [$^{35}$S]p53 bands on the autoradiograph were represented graphically beneath the autoradiograph with the mock transfectant at time 0 set as 100%. Indeed, assessment of p53 translation by [$^{35}$S]methionine pulse-labeling demonstrated that RPL26 transfection directly increases p53 translation in a dose-dependent manner and augments the irradiation-induced increase in p53 translation. Pulse-labeled p53 was immunoprecipitated from MCF7 cells transfected with increasing amounts of GFP-RPL26 30 minutes after 0 or 5 Gy IR and assessed by autoradiography and immunoblot. Total amounts of GFP-RPL26 were assessed by immunoblot and total [$^{35}$S]methionine incorporation into cellular proteins was assessed by autoradiography. Importantly, RPL26 overexpression did not alter overall cellular translation levels, as shown by similar amounts of newly synthesized (i.e., [$^{35}$S]methionine-labeled) protein in whole cell extracts. The same experiment was performed in the p53-mutant cell line, SW480, to further eliminate any possible contribution of an increase in p53 half-life or total levels to the increased p53 metabolic labeling after IR. Transfection of RPL26 into SW480 cells increased p53 translation, particularly after IR.

Actively translated mRNAs are preferentially associated with polysomes, so the distribution of p53 mRNA on ribosomes was assessed by sucrose gradient centrifugation. RNA from MCF7 cells transfected with a GFP-mock or GFP-RPL26 vector was fractionated by sucrose gradient centrifugation and analyzed by Northern blot (from lightest fraction to heaviest fraction). Fractionated ribosomal RNA was also resolved by agarose gel electrophoresis and visualized with ethidium bromide. Overexpression of RPL26 induced a measurable translocation of p53 mRNA into polysomes, whereas the distribution of actin mRNA was unaffected. Therefore, RPL26 binds to the 5'UTR of p53 mRNA, increases the amount of p53 mRNA in polysomes, and measurably increases p53 translation.

Decreasing Endogenous RPL26 Levels Attenuates p53 Expression and Translation

To explore whether modulation of endogenous RPL26 affects p53 protein levels, cellular RPL26 was down-regulated by introduction of siRNA. A rabbit polyclonal antibody generated against human RPL26 was used to document RPL26 levels. FLAG-mock or FLAG-RPL26 was transiently overexpressed in 293T cells. 24 hours after transfection, cells were harvested and analyzed by immunoblotting. Endogenous RPL26 or FLAG tagged RPL26 was blotted using preimmune serum, anti-FLAG M2 antibody, or the new affinity-purified RPL26 polyclonal antibody. Control siRNA or RPL26 siRNA was transiently transfected in MCF7 cells. 48 hours after transfection, cells were harvested and analyzed by immunoblotting. Endogenous RPL26 was blotted using affinity-purified RPL26 polyclonal antibody.

Levels of various proteins in cells transfected with siRNA against RPL26 were examined to determine RPL26 effects on ATM levels or activation. MCF7 cells were transfected with a control siRNA or siRNA against RPL26 and either irradiated to 5 Gy or unirradiated and harvested at 0, 1, 3, 6, or 9 hours. Protein levels were then assessed by immunoblot. Transfection of MCF7 cells with RPL26 siRNA reduced endogenous RPL26 by over 75% and markedly attenuated p53 induction by IR. This had no measurable effect on ATM levels or activation.

Similarly, reduction of endogenous RPL26 significantly limited increases in p53 translation and protein levels after ultraviolet (UV) irradiation. MCF7 cells transfected with a control siRNA or siRNA against RPL26 were exposed to 0 or 10 J/m2 UV, harvested at 0, 2, an 4 hour intervals after irradiation, and p53 expression was analyzed by immunoblot. p53 translation was then evaluated by [$^{35}$S]methionine pulse-labeling in UV-irradiated MCF7 cells transfected with control siRNA and RPL26 siRNA. Newly synthesized p53 was identified by [$^{35}$S]methionine incorporation shown by autoradiography 2 hours after exposure to 10 J/m2 UV. Immunoblot analysis showed that equal amounts of p53 were immunoprecipitated. The results demonstrated that reduction of RPL26 decreased p53 protein levels after UV irradiation.

To demonstrate that the siRNA was modulating p53 by specifically affecting RPL26 and not some other intracellular target, an RPL26 cDNA was generated that is resistant to the effects of the siRNA. The C-terminal domain of RPL26 was noted to have the stimulatory effects on p53 translation and this domain was used to complement the inhibition of RPL26 by an siRNA that targeted the N-terminal half of the RPL26 RNA. This siRNA-resistant construct reversed the inhibition of p53 induction by IR caused by the siRNA. MCF7 cells were transfected with a control siRNA or siRNA against RPL26 and then transfected with a GFP-mock vector or the GFP-RPL26 deletion mutant plasmid 24 hours after siRNA transfection. 24 hours after plasmid transfection, cells were irradiated and harvested 3 hours after 0 or 5 Gy IR. Protein levels were assessed by immunoblot. Similarly, the siRNA blunted IR-induced increases in p53 translation, and the siRNA-resistant RPL26 construct reversed this inhibition. A GFP-mock vector or the GFP-RPL26 deletion mutant plasmid was transfected into MCF7 cells previously transfected with RPL26 siRNA as described above. Cells were exposed to 0 or 5Gy IR, pulse-labeled (5 minutes) with [$^{35}$S]methionine and newly synthesized p53 was assessed by autoradiography. Total levels of immunoprecipitated p53 and [$^{35}$S]methionine incorporation into total cellular proteins were identified.

Further evidence for an important role for endogenous RPL26 in p53 translation came from examination of the association of p53 mRNA with polysomes in unirradiated versus irradiated cells. As reported by Fu and Benchimol (Fu and Benchimol, EMBO J., 1997, 16(13):4117-25), a relative redistribution of p53 mRNA to the polysome fraction in irradiated cells was observed. Lysates from MCF7 cells transfected with a control siRNA or siRNA against RPL26 were exposed to 0 or 5 Gy IR and RNA extracted 30 minutes later was fractionated by sucrose gradient centrifugation. Fractions were analyzed by Northern blotting to identify p53 and actin mRNA and fractionated ribosomal RNA was resolved by agarose gel electrophoresis and visualized with ethidium bromide. Downregulation of endogenous RPL26 levels by siRNA blunted this radiation-induced redistribution.

RPL26 Effects Depend on the 5'UTR of p53 mRNA and Require a Minimal Region of RPL26

Using the yeast three-hybrid assay, the present inventors mapped the domain of the p53 5'UTR to which RPL26 binds to a region including 5'UTR nucleotides −78 to −1 having the sequence TCGGGCTGGGAGCGTGCTTTCCACGACG-GTGACACGCTTCCCTGGATTG GCAGCCAGACTGC-CTTCCGGGTCACTGCC (SEQ ID NO: 5; FIG. 1A). Yeast was cotransformed with a p53 5'UTR deletion mutant (bait) and RPL26-expressing vector (prey). Next, constructs that had various lengths of p53 5'UTR were transfected into H1299 cells in the presence or absence of RPL26 and the levels of p53 expression were examined. Capped p53 mRNA that represented several 5'UTR-deletion mutants (1, 22, 75, 146, or 192 nucleotides) was cotransfected with firefly luciferase mRNA and a GFP-RPL26 expression vector or a GFP-mock expression vector into H1299 cells and protein levels were assessed by immunoblot. Transfection efficiency, mRNA content, and expression were equilibrated by similarity of luciferase levels. This assay showed that RPL26 cotransfection was able to increase the levels of p53 expression when the p53 5'UTR included at least nucleotides −22 to −1 with the sequence GACTGCCTTCCGGGTCACTGCC (SEQ ID NO: 6; FIG. 1B). No increase in p53 expression was seen in cells transfected with p53 mRNA without its 5'UTR (5'UTR nt length 1). Firefly luciferase mRNA containing an unrelated, vector-derived 5'UTR of 71 nucleotides of sequence GGGCGAATTGGGCCCTCTAGATGCAT-GCTCGAGCGGCCGCCAGTGTGATGGATATC TGCA-GAATTCGCCCT (SEQ ID NO: 7) was cotransfected as an internal control and no effects of RPL26 were seen on firefly luciferase protein levels (FIG. 1B).

Similar results were obtained examining the impact of RPL26 on translation of p53 mRNA using a rabbit reticulocyte in vitro transcription/translation system. Effect of RPL26 on p53 translation was assessed in rabbit reticulocyte lysate containing p53 cDNA's encoding several 5'UTR-deletion mutants (1, 22, 75, 146, or 192 nucleotides), firefly luciferase cDNA, and His-RPL26 or His-control cDNA. Expression of in vitro transcribed/translated p53, firefly luciferase, and His-RPL26 was assessed by immunoblotting. The differences in the exact 5'UTR sequence required in the yeast three-hybrid binding assay versus in the translation regulation assays may reflect differences in the nature of RPL26 binding required for the two different assay readouts. Regardless, both cell-based systems and in vitro systems demonstrate that the p53 5'UTR affects p53 translation/expression levels and that the effect of RPL26 on p53 translation requires the presence of the 5'UTR. As noted in the RNA transfection assays above, these translation assays also demonstrated a negative effect of the longer 5'UTR sequences, suggesting negative regulatory elements in these sequences.

Figure 1D:
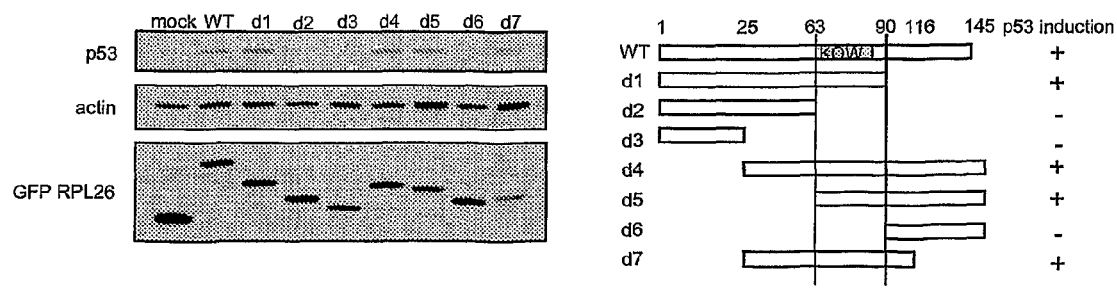

Human RPL26 is composed of 145 amino acids (Genbank Accession No. NP_000978; SEQ ID NO: 16) and contains a motif in its middle region RKDDEVQVVRGHYKGQ-QIGKVVQVYRK (SEQ ID NO: 10) previously referred to as a KOW (Kyrpides-Ouzounis-Woese) motif (Kyrpides et al., Trends Biochem. Sci. 1996; 21:425-426) and a resolvase motif at its carboxy terminus. A series of deletion mutants of RPL26 (i.e., RPL26 fragments corresponding to amino acids 2-89 (d1; SEQ ID NO: 17), 2-62 (d2; SEQ ID NO: 18), 2-45 (d3; SEQ ID NO: 19), 46-145 (d4; SEQ ID NO: 20), 63-145 (d5; SEQ ID NO: 21), 90-145 (d6; SEQ ID NO: 22), and 45-116 (d7; SEQ ID NO: 23); see FIG. 1D) were constructed to determine which part of RPL26 is required to induce p53 expression. These RPL26 deletion mutants were transfected into MCF7 cells and were characterized for their intracellular localization, ability to bind to the p53 5'UTR, and their ability to induce p53 protein (assessed by immunoblot). Mutants d1, d4, d5, and d7 lacking either the carboxy terminal or the amino terminal domains of RPL26 were still capable of increasing p53 protein levels with a minimal overlapping region containing amino acids 63-90 KGQQIGKV-VQVYRKKYVIYIERVQREKA (SEQ ID NO: 11) (overlapping with the KOW motif; FIG. 1D). There was an excellent correlation between the ability of the mutants to bind to the p53 5'UTR and their ability to increase p53 protein levels in cells. The one exception to this, the mutant d2, bound to the 5'UTR but still did not induce p53. These results suggest that a central domain of RPL26 protein is particularly important in this regulatory effect on p53.

RPL26 Affects p53-Dependent Apoptosis and Cell Cycle Arrest

The impact of RPL26 levels on p53 translation and induction prompted the present inventors to investigate its impact on cellular functions that depend on p53. Murine BaF3 cells undergo apoptosis in a p53-dependent manner at early time points after IR when IL-3 is withdrawn (Canman et al., Genes & Dev. 1995; 9:600-611). Apoptosis of BaF3 cells induced by 5 Gy IR was measured in GFP-mock or GFP-RPL26 overexpressing cells, which were cotransfected with mock empty vector, papilloma virus E6 expression vector, or dominant negative p53 expression vector. The percentage of cells undergoing apoptosis was determined by flow cytometric analysis of annexin V-stained cells 3 hours after IR. Cells were grown in the presence or absence of IL-3. Transfection of RPL26 increased the number of BaF3 cells undergoing IR-induced apoptosis, and inhibition of p53 function by co-transfection with vectors expressing either human papilloma virus (HPV) E6 or a dominant-negative mutant p53 protein eliminated this effect. Conversely, down-regulation of RPL26 with siRNA diminished irradiation-induced apoptosis. Apoptosis of BaF3 cells induced by 5 Gy IR was measured in control-siRNA transfected and in RPL26-siRNA transfected cells and the percentage of cells undergoing apoptosis determined as described above. Transfection of RPL26 also increased 5-fluorouracil-dependent cell death in human HCT116 colon cancer cells carrying wild-type p53 (Bunz et al., J. Clin. Invest 1999; 104:263-269), but had no measurable effect in isogenic HCT116 cells lacking p53. Induction of apoptosis of HCT116 parental or HCT116 p53-null cells at various times by 300 µM 5-fluorouracil treatment was measured by annexin V staining. A similar experiment was performed in control-siRNA or RPL26-siRNA transfected cells. Again, transfection of RPL26 siRNA reduced the 5-fluorouracil-induced, p53-dependent apoptosis.

In many cell types and physiologic settings, p53 induction results in G1 cell cycle arrest rather than apoptosis (Kastan et al., Cancer Res 1991; 51:6304-6311; Canman et al., Genes & Dev. 1995; 9:600-611; Michalovitz et al., Cell 1990; 62:671-680). MCF7 cells overexpressing GFP-mock or GFP-RPL26 were cotransfected with mock empty vector, papilloma virus E6 expression vector, or dominant negative p53 expression vector. Cell cycle distribution was determined by a BrdU pulse-label method 24 h after transfection. The G1/S index was obtained from three independent experiments. Overexpression of RPL26 induced a marked G1 arrest that was abrogated when either HPV-E6 or dominant-negative p53 was co-transfected. The p53-dependent effects of RPL26 on cell proliferation were also examined in a colony growth assay. Immortalized ARF−/−p53+/+ or ARF−/−p53−/− mouse embryonic fibroblasts were infected with retroviruses encoding GFP alone or GFP-RPL26. Infection efficiency was more than 95% as determined by GFP expression. Though infection with RPL26 markedly suppressed cell growth in the ARF−/−p53+/+ cells, it had no measurable effect in the ARF−/−p53−/− cells, thus demonstrating that the growth arrest was dependent on p53, but not on ARF.

Nucleolin Also Affects p53 Levels and Translation

The nucleolar protein, nucleolin, was also identified in the screens conducted by the present inventors as a protein that specifically interacted with the p53 5'UTR (Table 2), and it has previously been suggested that RPL26 is a component of the nucleolin-containing ribonucleocomplex (Yanagida et al., Proteomics. 2001; 1:1390-1404). An interaction between RPL26 and nucleolin was confirmed in co-immunoprecipitation assays. RPL26 was immunoprecipitated with anti-FLAG antibody from cell lysate after RNase A treatment of 293T cells that had been transiently transfected with FLAG-mock or FLAG-RPL26 expression vector. One hour after 0 or 10 Gy IR, cells were harvested and immunoprecipitates analyzed by immunoblot for nucleolin and RPL26. The results confirmed that RPL26-and-nucleolin interact. In a similar experiment, control IgG or anti-nucleolin was used for immunoprecipitation. No effect of irradiation on the interaction was observed, though such an effect might not be expected with overexpressed transfected proteins. The effect on p53 protein levels and translation of modulating nucleolin was then explored.

Transient transfection of nucleolin into MCF7 cells reduced p53 protein levels in a dose-dependent manner, but had no effect on p53 mRNA levels. Semi quantitative RT-PCR was performed of RNA extracted one hour after exposing MCF7 cells to 0 or 5 Gy IR. MCF7 cells were transfected with GFP-mock or GFP-nucleolin. p53 and GAPDH PCR products were identified and collected after 20 cycles or 24 cycles of PCR. Levels of p53 and p53 targets were assessed by immunoblot at various times after 5 Gy IR in MCF7 cells stably transfected with a GFP-mock vector and a GFP-nucleolin vector. Levels of [$^{35}$S]methionine-labeled p53 in the same transfected MCF-7 cells 30 minutes after 0 or 5 Gy IR. Total amounts of immunoprecipitated p53 were identified by immunoblot and incorporation of [$^{35}$S]methionine into total cellular protein was identified by autoradiography. Stable transfection of nucleolin into MCF7 cells blunted IR-induction of p53 protein and inhibited the IR-induced increase in p53 translation without measurably affecting overall translation levels.

It was further determined that shRNA against nucleolin induces p53 expression. MCF7 cells transfected with a control shRNA or shRNA against nucleolin were irradiated to 5 Gy or unirradiated and harvested at 1 hr after irradiation, then subjected to Western analysis with antibodies to p53 and nucleolin. Actin was included as a protein loading control. Levels of [$^{35}$S]methionine-labeled p53 were similarly studied in the same transfected MCF-7 cells 30 minutes after 0 or 5 Gy IR. Total amounts of immunoprecipitated p53 were shown by immunoblot and incorporation of [$^{35}$S]methionine into total cellular protein was shown by autoradiography. Endogenous nucleolin levels were reduced ~50% by infection of MCF7 cells with a short hairpin RNA (shRNA) construct for nucleolin. This moderate reduction in nucleolin increased basal and IR-induced p53 protein levels and p53 translation. If nucleolin overexpression suppresses p53 function, then it might be expected to function as an oncogene in a rat embryo fibroblast (REF) transformation assay. Early passage REFs were infected with retroviruses expressing GFP alone, GFP-nucleolin or mutant p53 (R175H) along with oncogenic mutant Ras.-Morphological changes of REF transformed with oncogenic Ras and GFP-mock, mutant p53 (R175H), and GFP-nucleolin were studied, as was colony formation activity in soft agar plates. Control infected REFs retained a flat morphology while cells infected with GFP-nucleolin or mutant p53 lost contact inhibition and showed dramatic morphologic changes. Furthermore, both mutant p53 and nucleolin infection resulted in proliferation and colony formation in soft agar.

Since both RPL26 and nucleolin bind to the 5'UTR of p53, but induce opposing effects on p53 translation, it was further investigated whether the two proteins compete for these effects. Levels of various proteins were assessed by immunoblot in MCF7 cells that had been transiently transfected with nucleolin or varying amounts of GFP-RPL26. Extracts were made 30 min after exposure to 0 or 5 Gy IR. The effects of nucleolin and varying amounts of RPL26 on p53 translation in MCF7 cells were assessed. Enforced expression of nucleolin in MCF7 cells had the expected effect of reducing basal and IR-induced p53 protein levels. Co-transfecting RPL26 into these nucleolin-overexpressing cells reversed the blockade of p53 induction in a dose-dependent manner. Similarly, transfection of RPL26 reversed the nucleolin-mediated inhibition of p53 translation after IR.

Discussion

The data disclosed herein demonstrate that translational control mechanisms are critically important in modulating cellular levels of the p53 tumor suppressor protein after DNA damage. Measurable increases in the translation of p53 mRNA after DNA damage were documented for both wild-type and mutant p53 proteins, although increased translation rates do not result in detectably increased levels of mutant p53 protein because of its already long half-life. The present inventors identified three proteins, RPL26, nucleolin and p53 protein itself, that bind to the 5'UTR of p53 both in vitro and in cells. Increased levels of RPL26 enhance both basal and DNA damaged-induced translation of p53 mRNA in vitro and in cells and enhance cellular functions dependent on p53, such as cell cycle arrest and apoptosis. The effects of RPL26 on p53 translation require the presence of the 5'UTR. Reduction of RPL26 levels by siRNA blunt these p53-dependent responses, thus demonstrating a role for endogenous RPL26 in DNA damage responses. Nucleolin has the opposite effects on p53, with overexpression reducing-basal and DNA damage-induced translation and inhibition of nucleolin enhancing translation.

The sequence of the p53 5'UTR predicts a highly structured stem loop that would be expected to inhibit translation. In fact, both the in vitro and cell-based translation studies disclosed herein suggest a sequence that inhibits translation in the general region where this structure should be present and where RPL26 binds to the 5'UTR and exerts its positive effects. Nucleolin promotes annealing of both RNA and DNA single strand sequences (Thyagarajan et al., Cell Mol. Genet. 1998; 24:263-272; Hanakahi et al., Biochemistry 2000; 39:15493-15499), so its inhibitory effects on p53 translation may reflect its ability to promote the double-strand RNA stem loop structures in the 5'UTR.

Not wishing to be bound by any particular theory, the present inventors hypothesize that, since p53 translation is increased after DNA damage and both RPL26 and nucleolin contribute to the control of p53 translation during this stress response, DNA damage must somehow be signaling to one or both of these proteins. Nucleolin binding to the p53 5'UTR does not change after IR, suggesting the possibility that RPL26, but not nucleolin, is the modulated target after DNA damage. Supporting this possibility, the present inventors found that IR induced a measurable change in the intracellular distribution of RPL26, but not nucleolin, in MCF7 cells, with a relative increase in the amount of RPL26 protein located in the nucleoplasm. Another potential effect of DNA damage on RPL26 could be the introduction of post-translational modifications. Indeed, the present inventors have identified that RPL26 is a phosphoprotein. The other change that occurs in the cells after IR is the increased levels of p53 protein itself. Since p53 protein also appears to be binding to the 5'UTR of p53 mRNA, it is conceivable that its induction and binding also affects the relative interactions of nucleolin, RPL26 and the 5'UTR.

The mechanisms controlling protein translation may not be limited to p53 regulation, but rather may be of general significance in cellular stress responses. Cellular stresses such as hypoxia and high doses of certain types of DNA damaging agents are potent inhibitors of general protein translation in cells (Koumenis et al., Mol. Cell. Biol. 2002; 22:7405-7416; Deng et al., Curr. Biol. 2002; 12:1279-1286). In order to maintain-adequate levels-of selected proteins that help the cell cope with the stress, certain mechanisms must come into play to maintain the translation of these proteins despite the general decrease in protein translation. p53 is certainly one example of a protein whose synthesis must be maintained, even in the face of stresses like hypoxia (Koumenis et al., Mol. Cell. Biol. 2002; 22:7405-7416; Koumenis et al., Mol Cell Biol 2001; 21:1297-1310). Though the present inventors specifically identified RPL26 and nucleolin as modulators of p53 translation in these studies, it has previously been reported that nucleolin binds to at least 40 different mRNAs in response to genotoxic stress and that this binding is an important component of the general cellular response to stress (Yang et al., Nucleic Acids Res. 2002; 30:2251-2260). The RNA binding protein, HuR, binds to the p53 3'UTR and enhances translation efficiency after UV irradiation (Mazan-Mamczarz et al., Proc. Natl. Acad. Sci. U.S.A 2003; 100: 8354-8359) and several ribosomal proteins have been reported to bind to Hdm2 protein and affect p53 protein levels by inhibiting the association of Hdm2 with p53 and increasing the p53 protein half-life (Dai et al., Mol. Cell. Biol. 2004; 24:7654-7668; Dai et al., J. Biol. Chem. 2004; 279:44475-44482; Jin et al., Mol. Cell. Biol. 2004; 24:7669-7680; Lohrum et al., Cancer Cell 2003; 3:577-587; Zhang et al., Mol. Cell. Biol. 2003; 23:8902-8912). Thus, both positive and negative translational control of many different proteins may be part of the highly coordinated response of cells to DNA damage and other cellular stresses.

Though the p53 gene is mutated in many human cancers, there are many other human cancers where p53 function is altered either because of expression of viral proteins that inhibit p53 function or because of alterations in other cellular genes, such as HDM2 or ARF, that interact with p53 (Vogelstein et al., Nature 2000; 408:307-310; Sherr et al., Nature Reviews Molecular Cell Biology 2001; 2:731-737). The properties described here for RPL26 and nucleolin raise the possibility that their dysregulation could contribute to tumorigenesis by alteration of p53 function.

REFERENCES

Ashcroft, M., Kubbutat, M. H. G., and Vousden, K. H. (1999). Regulation of p53 function and stability by phosphorylation. Molecular & Cellular Biology 19, 1751-1758.

Bakkenist, C. J. and Kastan, M. B. (2003). DNA damage activates ATM through intermolecular autophosphorylation and dimer dissociation. Nature 421, 499-506.

Beck-Engeser, G. B., Monach, P. A., Mumberg, D., Yang, F., Wanderling, S., Schreiber, K., Espinosa, R., III, Le Beau, M. M., Meredith, S.C., and Schreiber, H. (2001). Point mutation in essential genes with loss or mutation of the second allele: relevance to the retention of tumor-specific antigens. J. Exp. Med. 194, 285-300.

Bernstein, D.S., Buter, N., Stumpf, C., and Wickens, M. (2002). Analyzing mRNA-protein complexes using a yeast three-hybrid system. Methods 26, 123-141.

Bunz, F., Hwang, P. M., Torrance, C., Waldman, T., Zhang, Y., Dillehay, L., Williams, J., Lengauer, C., Kinzler, K. W., and Vogelstein, B. (1999). Disruption of p53 in human cancer cells alters the responses to therapeutic agents. J. Clin. Invest 104, 263-269.

Busch, H., Lane, M., Dams, H. R., Debakey, M. E., and Muramatsu, M. (1965). Isolation of nucleoli from human tumors. Cancer Res. 25, 225-233.

Canman, C. E., Gilmer, T., Coutts, S., and Kastan, M. B. (1995). Growth factor modulation of p53-mediated growth arrest vs. apoptosis. Genes & Dev. 9, 600-611.

Canman, C. E. and Kastan, M. B. (1998). Small contribution of G1 checkpoint control manipulation to modulation of p53-mediated apoptosis. Oncogene 16, 957-966.

Chu, E., Copur, S. M., Ju, J., Chen, T. M., Khleif, S., Voeller, D. M., Mizunuma, N., Patel, M., Maley, G. F., Maley, F., and Allegra, C. J. (1999). Thymidylate synthase protein and p53 mRNA form an in vivo ribonucleoprotein complex. Mol. Cell. Biol. 19, 1582-1594.

Dai, M. S, and Lu, H. (2004). Inhibition of MDM2-mediated p53 ubiquitination and degradation by ribosomal protein L5. J. Biol. Chem. 279, 44475-44482.

Dai, M. S., Zeng, S. X., Jin, Y., Sun, X. X., David, L., and Lu, H. (2004). Ribosomal protein L23 activates p53 by inhibiting MDM2 function in response to ribosomal perturbation but not to translation inhibition. Mol. Cell. Biol. 24, 7654-7668.

Daniely, Y., Dimitrova, D. D., and Borowiec, J. A. (2002). Stress-dependent nucleolin mobilization mediated by p53-nucleolin complex formation. Mol. Cell. Biol. 22, 6014-6022.

Deng, J., Harding, H. P., Raught, B., Gingras, A. C., Berlanga, J. J., Scheuner, D., Kaufman, R. J., Ron, D., and Sonenberg, N. (2002). Activation of GCN2 in UV-irradiated cells inhibits translation. Curr. Biol. 12, 1279-1286.

Derenzini, M., Sirri, V., Trere, D., and Ochs, R. L. (1995). The quantity of nucleolar proteins nucleolin and protein B23 is related to cell doubling time in human cancer cells. Lab Invest 73, 497-502.

El-Deiry, W. S., Tokino, T., Velculescu, V. E., Levy, D. B., Parsons, R., Trent, M., Lin, D., Mercer, W. E., Kinzler, K. W., and Vogelstein, B. (1993). WAF1, a Potential Mediator of p53 Tumor Suppression. Cell 75, 817-825.

Fang, S., Jensen, J.P., Ludwig, R. L., Vousden, K. H., and Weissman, A. M. (2000). Mdm2 is a RING finger-dependent ubiquitin protein ligase for itself and p53. J Biol Chem 275, 8945-8951.

Fu, L. and Benchimol, S. (1997). Participation of the human p53 3'UTR in translational repression and activation following γ-irradiation. Embo J 16, 4117-4125.

Fu, L., Ma, W L., and Benchimol, S. A translational repressor element resides in the 3' untranslated region of human p53 mRNA. Oncogene 18, 6419-6424. 1999.

Fu, L., Minden, M. D., and Benchimol, S. (1996). Translational regulation of human p53 gene expression. EMBO J. 15, 4392-4401.

Giaccia, A. J. and Kastan, M. B. (1998). The complexity of p53 modulation: emerging patterns from divergent signals. Genes & Development 12, 2973-2983.

Gillet, G., Michel, D., Crisanti, P., Guerin, M., Herault, Y., Pessac, B., Calothy, G., Brun, G., and Volovitch, M. (1993). Serum factors and v-src control two complementary mitogenic pathways in quail neuroretinal cells in culture. Oncogene 8, 565-574.

Gray, N. K. and Wickens, M. (1998). Control of translation initiation in animals. Annu. Rev. Cell Dev. Biol. 14, 399-458.

Hainaut, P., Hernandez, T., Robinson, A., Rodriguez-Tome, P., Flores, T., Hollstein, M., Harris, C. C., and Montesano, R. (1998). IARC Database of p53 gene mutations in human tumors and cell lines: updated compilation, revised formats and new visualisation tools. Nucleic Acids Res. 26, 205-213.

Hammond, E. M., Denko, N. C., Dorie, M. J., Abraham, R. T., and Giaccia, A. J. (2002). Hypoxia links ATR and p53 through replication arrest. Mol Cell Biol. 22, 1834-1843.

Hanakahi, L. A., Bu, Z., and Maizels, N. (2000). The C-terminal domain of nucleolin accelerates nucleic acid annealing. Biochemistry 39, 15493-15499.

Haupt, Y., Maya, R., Kazaz, A., and Oren, M. (1997). Mdm2 promotes the rapid degradation of p53. Nature 387, 296-299.

Honda, R., Tanaka, H., and Yasuda, H. (1997). Oncoprotein MDM2 is a ubiquitin ligase E3 for tumor suppressor p53. FEBS Letters 420, 25-27.

Jin, A., Itahana, K., O'Keefe, K., and Zhang, Y. (2004). Inhibition of HDM2 and activation of p53 by ribosomal protein L23. Mol. Cell. Biol. 24, 7669-7680.

Ju, J., Pedersen-Lane, J., Maley, F., and Chu, E. (1999). Regulation of p53 expression by thymidylate synthase. Proc. Natl. Acad. Sci. U.S.A 96, 3769-3774.

Kamijo, T., Weber, J. D., Zambetti, G., Zindy, F., Roussel, M. F., and Sherr, C. J. (1998). Functional and physical interactions of the ARF tumor suppressor with p53 and Mdm2. Proc. Natl. Acad. Sci. U.S.A 95, 8292-8297.

Kastan, M. B., Onyekwere, O., Sidransky, D., Vogelstein, B., and Craig, R. W. (1991). Participation of p53 protein in the cellular response to DNA damage. Cancer Res 51, 6304-6311.

Kastan, M. B., Zhan, Q., El-Deiry, W. S., Carrier, F., Jacks, T., Walsh, W. V., Plunkett, B. S., Vogelstein, B., and Fornace, A. J., Jr. (1992). A mammalian cell cycle checkpoint pathway utilizing p53 and GADD45 is defective in ataxia-telangiectasia. Cell 71, 587-597.

Kern, S. E., Pietenpol, J. A., Thiagalingam, S., Seymor, A., Kinzler, K. W., and Vogelstein, B. (1992). Oncogenic forms of p53 inhibit p53-regulated gene expression. Science 256, 827-830.

Khosravi, R., Maya, R., Gottlieb, T., Oren, M., Shiloh, Y., and Shkedy, D. (1999). Rapid ATM-dependent phosphorylation of MDM2 precedes p53 accumulation in response to DNA damage. PNAS 96, 14973-14977.

Koumenis, C., Alarcon, R., Siliciano, H. E., Sutphin, P., Hoffman, W., Murphy, M., Derr, J., Taya, Y., Kastan, M., and Giaccia, A. (2001). Regulation of p53 by hypoxia: dissociation of transcriptional repression and apoptosis from p53-dependent transactivation. Mol Cell Biol 21, 1297-1310.

Koumnenis, C., Naczki, C., Koritzinsky, M., Rastani, S., Diehl, A., Sonenberg, N., Koromilas, A., and Wouters, B. G. (2002). Regulation of protein synthesis by hypoxia via activation of the endoplasmic reticulum kinase PERK and phosphorylation of the translation initiation factor eIF2alpha. Mol. Cell. Biol. 22, 7405-7416.

Kubbutat, M. H., Jones, S. N., and Vousden, K. H. (1997). Regulation of p53 stability by Mdm2. Nature 387, 299-303.

Kuerbitz, S. J., Plunkett, B. S., Walsh, W. V., and Kastan, M. B. (1992). Wild-type p53 is a cell cycle checkpoint determinant following irradiation. Proc Natl Acad Sci 89, 7491-7495.

Kyrpides, N. C., Woese, C. R., and Ouzounis, C. A. (1996). KOW: a novel motif linking a bacterial transcription factor with ribosomal proteins. Trends Biochem. Sci. 21, 425-426.

Lohrum, M. A., Ludwig, R. L., Kubbutat, M. H., Hanlon, M., and Vousden, K. H. (2003). Regulation of HDM2 activity by the ribosomal protein L11. Cancer Cell 3, 577-587.

Maki, C. G. and Howley, P. M. (1997). Ubiquitination of p53 and p21 is differentially affected by ionizing and UV radiation. Mol. Cell. Biol. 17, 355-363.

Malkin, D., Li, F. P., Strong, L. C., Fraumeni, J. F., Jr., Nelson, C. E., Kim, D. H., Kassel, J., Gryka, M. A., Bischoff, F. Z., Tainsky, M. A., et al. (1990). Germ line p53 mutations in a familial syndrome of breast cancer, sarcomas, and other neoplasms. Science 250, 1233-1238.

Maltzman, W. and Czyzyk, L. (1984). UV irradiation stimulates levels of p53 cellular tumor antigen in nontransformed mouse cells. Molec and Cell Biol 4(9), 1689-1694.

Maya, R., Balass, M., Kim, S.-T., Shkedy, D., Leal, J.-F. M., Shifman, O., Moas, M., Buschmann, T., Ronai, Z., Shiloh, Y., Kastan, M. B., Katzir, E., and Oren, M. (2001). ATM-dependent phosphorylation of Mdm2 on serine 395: role in p53 activation by DNA damage. Genes & Development 15, 1067-1077.

Mayo, L. D., Turchi, J. J., and Berberich, S. J. (1997). Mdm-2 Phosphorylation by DNA-dependent Protein Kinase Prevents Interaction with p53. Cancer Research 57, 5013-5016.

Mazan-Mamczarz, K., Galban, S., Lopez, d. S., I, Martindale, J. L., Atasoy, U., Keene, J. D., and Gorospe, M. (2003). RNA-binding protein HuR enhances p53 translation in response to ultraviolet light irradiation. Proc. Natl. Acad. Sci. U.S. A 100, 8354-8359.

Michalovitz, D., Halevy, O., and Oren, M. (1990). Conditional inhibition of transformation and of cell proliferation by a temperature-sensitive mutant of p53. Cell 62, 671-680.

Mignone, F., Gissi, C., Liuni, S., and Pesole, G. (2002). Untranslated regions of mRNAs. Genome Biol. 3, REVIEWS0004.

Momand, J., Zambetti, G. P., Olson, D. C., George, D. L., and Levine, A. J. (1992). The mdm-2 oncogene product forms a complex with the p53 protein and inhibits p53-mediated transactivation. Cell 69, 1237-1245.

Mosner, J., Mummenbrauer, T., Bauer, C., Sczakiel, G., Grosse, F., and Deppert, W. (1995). Negative Feedback regulation of wild-type p53 biosynthesis. The EMBO Journal 14, 4442-4449.

Ohira, M., Morohashi, A., Inuzuka, H., Shishikura, T., Kawamoto, T., Kageyama, H., Nakamura, Y., Isogai, E., Takayasu, H., Sakiyama, S., Suzuki, Y., Sugano, S., Goto, T., Sato, S., and Nakagawara, A. (2003). Expression profiling and characterization of 4200 genes cloned from primary neuroblastomas: identification of 305 genes differentially expressed between favorable and unfavorable subsets. Oncogene 22, 5525-5536.

Oliner, J. D., Pietenpol, J. A., Thiagalingam, S., Gyuris, J., Kinzler, K. W., and Vogelstein, B. (1993). Oncoprotein mdm2 conceals the activation domain of tumor suppressor p53. Nature 362, 857-860.

Palmero, I., Pantoja, C., and Serrano, M. (1999). p19ARF links the tumor suppressor p53 to Ras. Nature 395, 127.

Pomerantz, J., Schreiber-Agus, N., Liegeois, N. J., Silverman, A., Alland, L., Chin, L., Potes, J., Chen, K., Orlow, I., Lee, H. W., Cordon-Cardo, C., and DePinho, R. A. (1998). The Ink4a tumor suppressor gene product, p19Arf, interacts with MDM2 and neutralizes MDM2's inhibition of p53. Cell 92, 713-723.

Price, B. D. and Calderwood, S. K. (1993). Increased sequence-specific p53-DNA binding activity after DNA damage is attenuated by phorbol esters. Oncogene 8, 3055-3062.

Roussel, P. and Hernandez-Verdun, D. (1994). Identification of Ag-NOR proteins, markers of proliferation related to ribosomal gene activity. Exp. Cell Res. 214, 465-472.

Rubbi, C. P. and Milner, J. (2003). Disruption of the nucleolus mediates stabilization of p53 in response to DNA damage and other stresses. EMBO J. 22, 6068-6077.

SenGupta, D. J., Zhang, B., Kraemer, B., Pochart, P., Fields, S., and Wickens, M. (1996). A three-hybrid system to detect RNA-protein interactions in vivo. Proc. Natl. Acad. Sci. U.S.A 93, 8496-8501.

Sherr, C. J. (2001). The INK4a/ARF network in tumour suppression. Nature Reviews Molecular Cell Biology 2, 731-737.

Sherr, C. J. and Weber, J. D. (2000). The ARF/p53 pathway. Curr. Opin. Genet. Dev. 10, 94-99.

Shieh, S.-Y., Ikeda, M., Taya, Y., and Prives, C. (1997). DNA Damage-Induced Phosphorylation of p53 Alleviates Inhibition by MDM2. Cell 91, 325-334.

Stott, F. J., Bates, S., James, M. C., McConnell, B. B., Starborg, M., Brookes, S., Palmero, I., Ryan, K., Hara, E., Vousden, K. H., and Peters, G. (1998). The alternative product from the human CDKN2A locus, p14(ARF), participates in a regulatory feedback loop with p53 and MDM2. EMBO J. 17, 5001-5014.

Stripecke, R., Oliveira, C. C., McCarthy, J. E., and Hentze, M. W. (1994). Proteins binding to 5' untranslated region sites: a general mechanism for translational regulation of mRNAs in human and yeast cells. Mol. Cell. Biol. 14, 5898-5909.

Sugimoto, M., Kuo, M. L., Roussel, M. F., and Sherr, C. J. (2003). Nucleolar Arf tumor suppressor inhibits ribosomal RNA processing. Mol. Cell. 11, 415-424.

Thyagarajan, B., Lundberg, R., Rafferty, M., and Campbell, C. (1998). Nucleolin promotes homologous DNA pairing in vitro. Somat. Cell Mol. Genet. 24, 263-272.

Tibbetts, R. S., Brumbaugh, K. M., Williams, J. M., Sarkaria, J. N., Cliby, W. A., Shieh, S. Y., Taya, Y., Prives, C., and Abraham, R.T. (1999). A role for ATR in the DNA damage-induced phosphorylation of p53. Genes & Development 13, 152-157.

Trotta, R., Vignudelli, T., Candini, O., Intine, R. V., Pecorari, L., Guerzoni, C., Santilli, G., Byrom, M. W., Goldoni, S., Ford, L. P., Caligiuri, M. A., Maraia, R. J., Perrotti, D., and Calabretta, B. (2003). BCR/ABL activates mdm2 mRNA translation via the La antigen. Cancer Cell 3, 145-160.

Tuck, S. P. and Crawford, L. (1989). Characterization of the human p53 gene promoter. Mol. Cell. Biol. 9, 2163-2172.

Vogelstein, B., Lane, D., and Levine, A. J. (2000). Surfing the p53 network. Nature 408, 307-310.

Vousden, K. H. and Lu, X. (2002). Live or let die: the cell's response to p53. Nat Rev Cancer 2, 594-604.

Whitfield, M. L., Zheng, L. X., Baldwin, A., Ohta, T., Hurt, M. M., and Marzluff, W. F. (2000). Stem-loop binding protein, the protein that binds the 3' end of histone mRNA, is cell cycle regulated by both translational and posttranslational mechanisms. Mol. Cell. Biol. 20, 4188-4198.

Wright, J. A., Keegan, K. S., Herendeen, D. R., Bentley, N. J., Carr, A. M., Hoekstra, M. F., and Concannon, P. (1998). Protein kinase mutants of human ATR increase sensitivity to UV and ionizing radiation and abrogate cell cycle checkpoint control. Pro Natl Acad Sci USA 95, 7445-7450.

Yanagida, M., Shimamoto, A., Nishikawa, K., Furuichi, Y., Isobe, T., and Takahashi, N. (2001). Isolation and proteomic characterization of the major proteins of the nucleolin-binding ribonucleoprotein complexes. Proteomics. 1, 1390-1404.

Yang, C., Maiguel, D. A., and Carrier, F. (2002). Identification of nucleolin and nucleophosmin as genotoxic stress-responsive RNA-binding proteins. Nucleic Acids Res. 30, 2251-2260.

Zhang, Y., Wolf, G. W., Bhat, K., Jin, A., Allio, T., Burkhart, W. A., and Xiong, Y. (2003). Ribosomal protein L11 negatively regulates oncoprotein MDM2 and mediates a p53-dependent ribosomal-stress checkpoint pathway. Mol. Cell. Biol. 23, 8902-8912.

Zuker, M. (2003). Mfold web server for nucleic acid folding and hybridization prediction. Nucleic Acids Res. 31, 3406-3415.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed as new and desired to be protected by Letters Patent of the United States is:

1. A method for decreasing induction of the p53 tumor suppressor protein in a cell, which method comprises administering to the cell a nucleic acid-based molecule which competes with Ribosomal Protein L26 (RPL26) for interaction with a 5'-untranslated region (5'UTR) of p53 mRNA, and wherein said competition for the interaction of RPL26 with the 5'UTR of p53 mRNA is effective for decreasing induction of p53 tumor suppressor protein.

2. A method for decreasing the level of the p53 tumor suppressor protein in a cell comprising administering to the cell a short interfering RNA (siRNA) molecule having the sequence CCGAAAGGAUGAUGAAGUUUU (SEQ ID NO: 8).

3. A method for preventing negative effects of a cellular stress in a mammal, which method comprises decreasing induction of the p53 tumor suppressor protein in the cells of the mammal which are affected by the cellular stress by administering to said cells a nucleic acid-based molecule which competes with Ribosomal Protein L26 (RPL26) for interaction with a 5'-untranslated region (5'UTR) of p53 mRNA.

4. The method of claim 1, wherein the nucleic acid-based molecule is an oligonucleotide corresponding to a fragment of the 5'UTR of p53 mRNA, which oligonucleotide can compete with RPL26 for interaction with the 5'UTR of p53 mRNA.

5. The method of claim 4, wherein the 5'UTR of p53 mRNA consists of nucleotides (nt) −78 to −1.

6. The method of claim 5, wherein the 5'UTR of p53 mRNA has the sequence TCGGGCTGGGAGCGTGCTTTCCACGACGGTGACACGCTTCCCTGGATTGGCAGCCA GACTGCCTTCCGGGTCACTGCC (SEQ ID NO: 5).

7. The method of claim 4, wherein the 5'UTR of p53 mRNA consists of nucleotides (nt) −22 to −1.

8. The method of claim 7, wherein the 5'UTR of p53 mRNA has the sequence GACTGCCTTCCGGGTCACTGCC (SEQ ID NO: 6).

9. The method of claim 3, wherein the nucleic acid-based molecule is an oligonucleotide corresponding to a fragment of the 5'UTR of p53 mRNA, which oligonucleotide can compete with RPL26 for interaction with the 5'UTR of p53 mRNA.

10. The method of claim 9, wherein the 5'UTR of p53 mRNA consists of nucleotides (nt) −78 to −1.

11. The method of claim 10, wherein the 5'UTR of p53 mRNA has the sequence TCGGGCTGGGAGCGTGCTTTCCACGACGGTGACACGCTTCCCTGGATTGGCAGCCA GACTGCCTTCCGGGTCACTGCC (SEQ ID NO: 5).

12. The method of claim 9, wherein the 5'UTR of p53 mRNA consists of nucleotides (nt) −22 to −1.

13. The method of claim 12, wherein the 5'UTR of p53 mRNA has the sequence GACTGCCTTCCGGGTCACTGCC (SEQ ID NO: 6).

* * * * *

SEQUENCE LISTING

```
<160> NUMBER OF SEQ ID NOS: 41

<210> SEQ ID NO 1
<211> LENGTH: 139
<212> TYPE: DNA
<213> ORGANISM: Homo sapiens

<400> SEQUENCE: 1
aaaagtctag agccaccgtc cagggagcag gtagctgctg ggctccgggg acactttgcg      60
ttcgggctgg gagcgtgctt tccacgacgg tgacacgctt ccctggattg gcagccagac     120
tgccttccgg gtcactgcc                                                  139

<210> SEQ ID NO 2
<211> LENGTH: 75
<212> TYPE: DNA
<213> ORGANISM: Homo sapiens

<400> SEQUENCE: 2
ggctgggagc gtgctttcca cgacggtgac acgcttccct ggattggcag ccagactgcc      60
ttccgggtca ctgcc                                                       75

<210> SEQ ID NO 3
<211> LENGTH: 190
<212> TYPE: DNA
<213> ORGANISM: Homo sapiens

<400> SEQUENCE: 3
gttttcccct cccatgtgct caagactggc gctaaaagtt ttgagcttct caaaagtcta      60
gagccaccgt ccagggagca ggtagctgct gggctccggg gacactttgc gttcgggctg     120
ggagcgtgct ttccacgacg gtgacacgct tccctggatt ggcagccaga ctgccttccg     180
ggtcactgcc                                                            190

<210> SEQ ID NO 4
<211> LENGTH: 190
<212> TYPE: DNA
<213> ORGANISM: Homo sapiens

<400> SEQUENCE: 4
gttttcccct cccatgtgct caagactggc gctaaaagtt ttgagcttct caaaagtcta      60
gagccaccgt ccagggagca ggtagctgct gggctccggg gacactttgc gttcgggctg     120
ggagcgtgct ttccacgacg gtgacacgct tccctggatt ggcagccaga ctgccttccg     180
ggtcactgcc                                                            190
```

-continued

<210> SEQ ID NO 5
<211> LENGTH: 78
<212> TYPE: DNA
<213> ORGANISM: Homo sapiens

<400> SEQUENCE: 5
tcgggctggg agcgtgcttt ccacgacggt gacacgcttc cctggattgg cagccagact    60
gccttccggg tcactgcc                                                  78

<210> SEQ ID NO 6
<211> LENGTH: 22
<212> TYPE: DNA
<213> ORGANISM: Homo sapiens

<400> SEQUENCE: 6
gactgccttc cgggtcactg cc                                             22

<210> SEQ ID NO 7
<211> LENGTH: 71
<212> TYPE: DNA
<213> ORGANISM: artificial
<220> FEATURE:
<223> OTHER INFORMATION: vector-derived 5'UTR (synthetic sequence)

<400> SEQUENCE: 7
gggcgaattg ggccctctag atgcatgctc gagcggccgc cagtgtgatg gatatctgca    60
gaattcgccc t                                                         71

<210> SEQ ID NO 8
<211> LENGTH: 21
<212> TYPE: RNA
<213> ORGANISM: artificial
<220> FEATURE:
<223> OTHER INFORMATION: RPL26-specific siRNA (synthetic sequence)

<400> SEQUENCE: 8
ccgaaaggau gaugaaguuu u                                              21

<210> SEQ ID NO 9
<211> LENGTH: 19
<212> TYPE: DNA
<213> ORGANISM: artificial
<220> FEATURE:
<223> OTHER INFORMATION: nucleolin-specific shRNA (synthetic sequence)

<400> SEQUENCE: 9
agagcgagat gcgagaaca                                                 19

<210> SEQ ID NO 10
<211> LENGTH: 27
<212> TYPE: PRT
<213> ORGANISM: Homo sapiens

<400> SEQUENCE: 10

Arg Lys Asp Asp Glu Val Gln Val Val Arg Gly His Tyr Lys Gly Gln
1               5                   10                  15

Gln Ile Gly Lys Val Val Gln Val Tyr Arg Lys
            20                  25

<210> SEQ ID NO 11
<211> LENGTH: 28
<212> TYPE: PRT
<213> ORGANISM: Homo sapiens -continued

<400> SEQUENCE: 11

Lys Gly Gln Gln Ile Gly Lys Val Val Gln Val Tyr Arg Lys Lys Tyr
1               5                   10                  15

Val Ile Tyr Ile Glu Arg Val Gln Arg Glu Lys Ala
            20                  25

<210> SEQ ID NO 12
<211> LENGTH: 251
<212> TYPE: DNA
<213> ORGANISM: Homo sapiens

<400> SEQUENCE: 12
acttgtcatg gcgactgtcc agctttgtgc caggagcctc gcaggggttg atgggattgg     60
ggttttcccc tcccatgtgc tcaagactgg cgctaaaagt tttgagcttc tcaaaagtct    120
agagccaccg tccagggagc aggtagctgc tgggctccgg ggacactttg cgttcgggct    180
gggagcgtgc tttccacgac ggtgacacgc ttccctggat tggcagccag actgccttcc    240
gggtcactgc c                                                        251

<210> SEQ ID NO 13
<211> LENGTH: 193
<212> TYPE: DNA
<213> ORGANISM: Homo sapiens

<400> SEQUENCE: 13
ggttttcccc tcccatgtgc tcaagactgg cgctaaaagt tttgagcttc tcaaaagtct     60
agagccaccg tccagggagc aggtagctgc tgggctccgg ggacactttg cgttcgggct    120
gggagcgtgc tttccacgac ggtgacacgc ttccctggat tggcagccag actgccttcc    180
gggtcactgc cat                                                      193

<210> SEQ ID NO 14
<211> LENGTH: 148
<212> TYPE: DNA
<213> ORGANISM: Homo sapiens

<400> SEQUENCE: 14
ttcatgccac catggccagc caacttttgc atgttttgta gagatggggt ctcacagtgt     60
tgcccaggct ggtctcaaac tcctgggctc aggcgatcca cctgtctcag cctcccagag    120
tgctgggatt acaattgtga gccaccac                                      148

<210> SEQ ID NO 15
<211> LENGTH: 21
<212> TYPE: DNA
<213> ORGANISM: artificial
<220> FEATURE:
<223> OTHER INFORMATION: control shRNA (synthetic sequence)

<400> SEQUENCE: 15
aatcagacgt ggaccagaag a                                              21

<210> SEQ ID NO 16
<211> LENGTH: 145
<212> TYPE: PRT
<213> ORGANISM: Homo sapiens

<400> SEQUENCE: 16

Met Lys Phe Asn Pro Phe Val Thr Ser Asp Arg Ser Lys Asn Arg Lys
1               5                   10                  15

```
Arg His Phe Asn Ala Pro Ser His Ile Arg Arg Lys Ile Met Ser Ser
            20                  25                  30

Pro Leu Ser Lys Glu Leu Arg Gln Lys Tyr Asn Val Arg Ser Met Pro
            35                  40                  45

Ile Arg Lys Asp Asp Glu Val Gln Val Val Arg Gly His Tyr Lys Gly
 50                  55                  60

Gln Gln Ile Gly Lys Val Val Gln Val Tyr Arg Lys Lys Tyr Val Ile
 65                  70                  75                  80

Tyr Ile Glu Arg Val Gln Arg Glu Lys Ala Asn Gly Thr Thr Val His
                 85                  90                  95

Val Gly Ile His Pro Ser Lys Val Val Ile Thr Arg Leu Lys Leu Asp
                100                 105                 110

Lys Asp Arg Lys Lys Ile Leu Glu Arg Lys Ala Lys Ser Arg Gln Val
            115                 120                 125

Gly Lys Glu Lys Gly Lys Tyr Lys Glu Glu Thr Ile Glu Lys Met Gln
    130                 135                 140

Glu
145

<210> SEQ ID NO 17
<211> LENGTH: 88
<212> TYPE: PRT
<213> ORGANISM: Homo sapiens

<400> SEQUENCE: 17

Lys Phe Asn Pro Phe Val Thr Ser Asp Arg Ser Lys Asn Arg Lys Arg
 1               5                  10                  15

His Phe Asn Ala Pro Ser His Ile Arg Arg Lys Ile Met Ser Ser Pro
            20                  25                  30

Leu Ser Lys Glu Leu Arg Gln Lys Tyr Asn Val Arg Ser Met Pro Ile
            35                  40                  45

Arg Lys Asp Asp Glu Val Gln Val Val Arg Gly His Tyr Lys Gly Gln
 50                  55                  60

Gln Ile Gly Lys Val Val Gln Val Tyr Arg Lys Lys Tyr Val Ile Tyr
 65                  70                  75                  80

Ile Glu Arg Val Gln Arg Glu Lys
                 85

<210> SEQ ID NO 18
<211> LENGTH: 61
<212> TYPE: PRT
<213> ORGANISM: Homo sapiens

<400> SEQUENCE: 18

Lys Phe Asn Pro Phe Val Thr Ser Asp Arg Ser Lys Asn Arg Lys Arg
 1               5                  10                  15

His Phe Asn Ala Pro Ser His Ile Arg Arg Lys Ile Met Ser Ser Pro
            20                  25                  30

Leu Ser Lys Glu Leu Arg Gln Lys Tyr Asn Val Arg Ser Met Pro Ile
            35                  40                  45

Arg Lys Asp Asp Glu Val Gln Val Val Arg Gly His Tyr
 50                  55                  60

<210> SEQ ID NO 19
<211> LENGTH: 44
<212> TYPE: PRT
<213> ORGANISM: Homo sapiens
```

```
<400> SEQUENCE: 19

Lys Phe Asn Pro Phe Val Thr Ser Asp Arg Ser Lys Asn Arg Lys Arg
1               5                   10                  15

His Phe Asn Ala Pro Ser His Ile Arg Arg Lys Ile Met Ser Ser Pro
            20                  25                  30

Leu Ser Lys Glu Leu Arg Gln Lys Tyr Asn Val Arg
        35                  40

<210> SEQ ID NO 20
<211> LENGTH: 100
<212> TYPE: PRT
<213> ORGANISM: Homo sapiens

<400> SEQUENCE: 20

Ser Met Pro Ile Arg Lys Asp Asp Glu Val Gln Val Val Arg Gly His
1               5                   10                  15

Tyr Lys Gly Gln Gln Ile Gly Lys Val Val Gln Val Tyr Arg Lys Lys
            20                  25                  30

Tyr Val Ile Tyr Ile Glu Arg Val Gln Arg Glu Lys Ala Asn Gly Thr
        35                  40                  45

Thr Val His Val Gly Ile His Pro Ser Lys Val Val Ile Thr Arg Leu
    50                  55                  60

Lys Leu Asp Lys Asp Arg Lys Lys Ile Leu Glu Arg Lys Ala Lys Ser
65                  70                  75                  80

Arg Gln Val Gly Lys Glu Lys Gly Lys Tyr Lys Glu Glu Thr Ile Glu
                85                  90                  95

Lys Met Gln Glu
            100

<210> SEQ ID NO 21
<211> LENGTH: 83
<212> TYPE: PRT
<213> ORGANISM: Homo sapiens

<400> SEQUENCE: 21

Lys Gly Gln Gln Ile Gly Lys Val Val Gln Val Tyr Arg Lys Lys Tyr
1               5                   10                  15

Val Ile Tyr Ile Glu Arg Val Gln Arg Glu Lys Ala Asn Gly Thr Thr
            20                  25                  30

Val His Val Gly Ile His Pro Ser Lys Val Val Ile Thr Arg Leu Lys
        35                  40                  45

Leu Asp Lys Asp Arg Lys Lys Ile Leu Glu Arg Lys Ala Lys Ser Arg
    50                  55                  60

Gln Val Gly Lys Glu Lys Gly Lys Tyr Lys Glu Glu Thr Ile Glu Lys
65                  70                  75                  80

Met Gln Glu

<210> SEQ ID NO 22
<211> LENGTH: 56
<212> TYPE: PRT
<213> ORGANISM: Homo sapiens

<400> SEQUENCE: 22

Ala Asn Gly Thr Thr Val His Val Gly Ile His Pro Ser Lys Val Val
1               5                   10                  15

Ile Thr Arg Leu Lys Leu Asp Lys Asp Arg Lys Lys Ile Leu Glu Arg
            20                  25                  30
```

```
Lys Ala Lys Ser Arg Gln Val Gly Lys Glu Lys Gly Lys Tyr Lys Glu
        35                  40                  45
Glu Thr Ile Glu Lys Met Gln Glu
        50                  55

<210> SEQ ID NO 23
<211> LENGTH: 72
<212> TYPE: PRT
<213> ORGANISM: Homo sapiens

<400> SEQUENCE: 23

Arg Ser Met Pro Ile Arg Lys Asp Asp Glu Val Gln Val Val Arg Gly
1               5                   10                  15
His Tyr Lys Gly Gln Gln Ile Gly Lys Val Val Gln Val Tyr Arg Lys
                20                  25                  30
Lys Tyr Val Ile Tyr Ile Glu Arg Val Gln Arg Glu Lys Ala Asn Gly
                35                  40                  45
Thr Thr Val His Val Gly Ile His Pro Ser Lys Val Val Ile Thr Arg
        50                  55                  60
Leu Lys Leu Asp Lys Asp Arg Lys
65                  70

<210> SEQ ID NO 24
<211> LENGTH: 710
<212> TYPE: PRT
<213> ORGANISM: Homo sapiens

<400> SEQUENCE: 24

Met Val Lys Leu Ala Lys Ala Gly Lys Asn Gln Gly Asp Pro Lys Lys
1               5                   10                  15
Met Ala Pro Pro Lys Glu Val Glu Glu Asp Ser Glu Asp Glu Glu
                20                  25                  30
Met Ser Glu Asp Glu Glu Asp Ser Ser Gly Glu Glu Val Val Ile
        35                  40                  45
Pro Gln Lys Lys Gly Lys Lys Ala Ala Ala Thr Ser Ala Lys Lys Val
        50                  55                  60
Val Val Ser Pro Thr Lys Lys Val Ala Val Ala Thr Pro Ala Lys Lys
65                  70                  75                  80
Ala Ala Val Thr Pro Gly Lys Lys Ala Ala Ala Thr Pro Ala Lys Lys
                85                  90                  95
Thr Val Thr Pro Ala Lys Ala Val Thr Thr Pro Gly Lys Lys Gly Ala
                100                 105                 110
Thr Pro Gly Lys Ala Leu Val Ala Thr Pro Gly Lys Lys Gly Ala Ala
                115                 120                 125
Ile Pro Ala Lys Gly Ala Lys Asn Gly Lys Asn Ala Lys Lys Glu Asp
        130                 135                 140
Ser Asp Glu Glu Glu Asp Asp Ser Glu Glu Asp Glu Glu Asp Asp
145                 150                 155                 160
Glu Asp Glu Asp Glu Asp Glu Asp Glu Ile Glu Pro Ala Ala Met Lys
                165                 170                 175
Ala Ala Ala Ala Ala Pro Ala Ser Glu Asp Glu Asp Asp Glu Asp Asp
        180                 185                 190
Glu Asp Asp Glu Asp Asp Asp Asp Glu Asp Asp Ser Glu Glu
        195                 200                 205
Glu Ala Met Glu Thr Thr Pro Ala Lys Gly Lys Lys Ala Ala Lys Val
        210                 215                 220
```

```
Val Pro Val Lys Ala Lys Asn Val Ala Glu Asp Glu Asp Glu Glu Glu
225                 230                 235                 240

Asp Asp Glu Asp Glu Asp Asp Asp Asp Glu Asp Asp Glu Asp
            245                 250                 255

Asp Asp Glu Asp Asp Glu Glu Glu Glu Glu Glu Glu Glu Pro
            260                 265                 270

Val Lys Glu Ala Pro Gly Lys Arg Lys Lys Glu Met Ala Lys Gln Lys
                275                 280                 285

Ala Ala Pro Glu Ala Lys Lys Gln Lys Val Glu Gly Thr Glu Pro Thr
290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
            355                 360                 365

Leu Lys Val Phe Gly Asn Glu Ile Lys Leu Glu Lys Pro Lys Gly Lys
370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Lys Thr Phe Glu Glu
            435                 440                 445

Lys Gln Gly Thr Glu Ile Asp Gly Arg Ser Ile Ser Leu Tyr Tyr Thr
                450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Gly Val Phe Glu Lys Ala Thr Phe Ile
            500                 505                 510

Lys Val Pro Gln Asn Gln Asn Gly Lys Ser Lys Gly Tyr Ala Phe Ile
            515                 520                 525

Glu Phe Ala Ser Phe Glu Asp Ala Lys Glu Ala Leu Asn Ser Cys Asn
            530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
            595                 600                 605

Ser Lys Gly Phe Gly Phe Val Asp Phe Asn Ser Glu Glu Asp Ala Lys
            610                 615                 620

Ala Ala Lys Glu Ala Met Glu Asp Gly Glu Ile Asp Gly Asn Lys Val
625                 630                 635                 640
```

```
Thr Leu Asp Trp Ala Lys Pro Lys Gly Glu Gly Gly Phe Gly Gly Arg
                645                 650                 655
Gly Gly Gly Arg Gly Gly Phe Gly Gly Arg Gly Gly Arg Gly Gly
        660                 665                 670
Arg Gly Gly Phe Gly Gly Arg Gly Arg Gly Gly Phe Gly Gly Arg Gly
            675                 680                 685
Gly Phe Arg Gly Gly Arg Gly Gly Gly Asp His Lys Pro Gln Gly
        690                 695                 700
Lys Lys Thr Lys Phe Glu
705                 710

<210> SEQ ID NO 25
<211> LENGTH: 393
<212> TYPE: PRT
<213> ORGANISM: Homo sapiens

<400> SEQUENCE: 25

Met Glu Glu Pro Gln Ser Asp Pro Ser Val Glu Pro Pro Leu Ser Gln
1               5                   10                  15
Glu Thr Phe Ser Asp Leu Trp Lys Leu Leu Pro Glu Asn Asn Val Leu
            20                  25                  30
Ser Pro Leu Pro Ser Gln Ala Met Asp Asp Leu Met Leu Ser Pro Asp
        35                  40                  45
Asp Ile Glu Gln Trp Phe Thr Glu Asp Pro Gly Pro Asp Glu Ala Pro
    50                  55                  60
Arg Met Pro Glu Ala Ala Pro Arg Val Ala Pro Ala Pro Ala Ala Pro
65                  70                  75                  80
Thr Pro Ala Ala Pro Ala Pro Ala Pro Ser Trp Pro Leu Ser Ser Ser
                85                  90                  95
Val Pro Ser Gln Lys Thr Tyr Gln Gly Ser Tyr Gly Phe Arg Leu Gly
            100                 105                 110
Phe Leu His Ser Gly Thr Ala Lys Ser Val Thr Cys Thr Tyr Ser Pro
        115                 120                 125
Ala Leu Asn Lys Met Phe Cys Gln Leu Ala Lys Thr Cys Pro Val Gln
    130                 135                 140
Leu Trp Val Asp Ser Thr Pro Pro Pro Gly Thr Arg Val Arg Ala Met
145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
        195                 200                 205
Arg Asn Thr Phe Arg His Ser Val Val Val Pro Tyr Glu Pro Pro Glu
    210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
            260                 265                 270
Arg Val Cys Ala Cys Pro Gly Arg Asp Arg Arg Thr Glu Glu Glu Asn
        275                 280                 285
Leu Arg Lys Lys Gly Glu Pro His His Glu Leu Pro Pro Gly Ser Thr
    290                 295                 300
```

```
Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 26
<211> LENGTH: 18
<212> TYPE: PRT
<213> ORGANISM: Homo sapiens

<400> SEQUENCE: 26

```
Ser Lys Asn Arg Lys Arg His Phe Asn Ala Pro Ser His Ile Arg Arg
1               5                   10                  15

Lys Ile
```

<210> SEQ ID NO 27
<211> LENGTH: 17
<212> TYPE: PRT
<213> ORGANISM: Homo sapiens

<400> SEQUENCE: 27

```
Arg Gln Val Gly Lys Glu Lys Gly Lys Tyr Lys Glu Glu Thr Ile Glu
1               5                   10                  15

Lys
```

<210> SEQ ID NO 28
<211> LENGTH: 32
<212> TYPE: DNA
<213> ORGANISM: artificial
<220> FEATURE:
<223> OTHER INFORMATION: primer

<400> SEQUENCE: 28
tcagatctcg agaagtttaa tcccttgtg ac                                    32

<210> SEQ ID NO 29
<211> LENGTH: 36
<212> TYPE: DNA
<213> ORGANISM: artificial
<220> FEATURE:
<223> OTHER INFORMATION: primer

<400> SEQUENCE: 29
agcagaattc ttactttcc cgctgcaccc gttcaa                                36

<210> SEQ ID NO 30
<211> LENGTH: 32
<212> TYPE: DNA
<213> ORGANISM: artificial
<220> FEATURE:
<223> OTHER INFORMATION: primer

<400> SEQUENCE: 30
tcagatctcg agaagtttaa tcccttttgtg ac                        32

<210> SEQ ID NO 31
<211> LENGTH: 31
<212> TYPE: DNA
<213> ORGANISM: artificial
<220> FEATURE:
<223> OTHER INFORMATION: primer

<400> SEQUENCE: 31
agcagaattc ttaatagtgt ccacgtacaa c                          31

<210> SEQ ID NO 32
<211> LENGTH: 32
<212> TYPE: DNA
<213> ORGANISM: artificial
<220> FEATURE:
<223> OTHER INFORMATION: primer

<400> SEQUENCE: 32
tcagatctcg agaagtttaa tcccttttgtg ac                        32

<210> SEQ ID NO 33
<211> LENGTH: 37
<212> TYPE: DNA
<213> ORGANISM: artificial
<220> FEATURE:
<223> OTHER INFORMATION: primer

<400> SEQUENCE: 33
agcagaattc ttatcgcacg ttgtacttct gtctcag                    37

<210> SEQ ID NO 34
<211> LENGTH: 24
<212> TYPE: DNA
<213> ORGANISM: artificial
<220> FEATURE:
<223> OTHER INFORMATION: primer

<400> SEQUENCE: 34
gtgcgatcca tgcccatccg aaag                                  24

<210> SEQ ID NO 35
<211> LENGTH: 25
<212> TYPE: DNA
<213> ORGANISM: artificial
<220> FEATURE:
<223> OTHER INFORMATION: primer

<400> SEQUENCE: 35
tcccgcttcg tcgagatctg agtac                                 25

<210> SEQ ID NO 36
<211> LENGTH: 30
<212> TYPE: DNA
<213> ORGANISM: artificial
<220> FEATURE:
<223> OTHER INFORMATION: primer

<400> SEQUENCE: 36
tcagatctcg agaaaggtca gcaaattggc                            30

<210> SEQ ID NO 37
<211> LENGTH: 28
<212> TYPE: DNA
<213> ORGANISM: artificial

```
<220> FEATURE:
<223> OTHER INFORMATION: primer

<400> SEQUENCE: 37
agcagaattc ttattcctgc atcttctc                                          28

<210> SEQ ID NO 38
<211> LENGTH: 30
<212> TYPE: DNA
<213> ORGANISM: artificial
<220> FEATURE:
<223> OTHER INFORMATION: primer

<400> SEQUENCE: 38
tcagatctcg aggctaatgg cacaactgtc                                        30

<210> SEQ ID NO 39
<211> LENGTH: 28
<212> TYPE: DNA
<213> ORGANISM: artificial
<220> FEATURE:
<223> OTHER INFORMATION: primer

<400> SEQUENCE: 39
agcagaattc ttattcctgc atcttctc                                          28

<210> SEQ ID NO 40
<211> LENGTH: 33
<212> TYPE: DNA
<213> ORGANISM: artificial
<220> FEATURE:
<223> OTHER INFORMATION: primer

<400> SEQUENCE: 40
tcagatctcg agcgatccat gcccatccga aag                                    33

<210> SEQ ID NO 41
<211> LENGTH: 31
<212> TYPE: DNA
<213> ORGANISM: artificial
<220> FEATURE:
<223> OTHER INFORMATION: primer

<400> SEQUENCE: 41
agcagaattc ttatttgcgg tctttgtcca g                                      31
```